(12) United States Patent
Williams et al.

(10) Patent No.: US 11,878,003 B2
(45) Date of Patent: Jan. 23, 2024

(54) COMPOSITION COMPRISING ORGANOSELENIUM COMPOUND FOR TREATMENT OF SKELETAL MUSCLE ATROPHY

(71) Applicant: Gwangju Institute of Science and Technology, Gwangju (KR)

(72) Inventors: Darren Reece Williams, Gwangju (KR); Da-Woon Jung, Gwangju (KR); Ji-Hyung Lee, Yongin-si (KR); Hyun-Jun Kim, Jeonju-si (KR); Seon-Wook Kim, Incheon (KR)

(73) Assignee: GWANGJU INSTITUTE OF SCIENCE AND TECHNOLOGY, Gwangju (KR)

( * ) Notice: Subject to any disclaimer, the term of this patent is extended or adjusted under 35 U.S.C. 154(b) by 95 days.

(21) Appl. No.: 17/448,755

(22) Filed: Sep. 24, 2021

(65) Prior Publication Data
US 2023/0210818 A1    Jul. 6, 2023

(51) Int. Cl.
*A61K 31/41*    (2006.01)
*A61P 21/06*    (2006.01)
*A23L 33/10*    (2016.01)

(52) U.S. Cl.
CPC .............. *A61K 31/41* (2013.01); *A23L 33/10* (2016.08); *A61P 21/06* (2018.01)

(58) Field of Classification Search
CPC ................................ A61K 31/41; A61P 21/06
See application file for complete search history.

(56) References Cited

FOREIGN PATENT DOCUMENTS

KR    10-2016-0137864 A    12/2016

*Primary Examiner* — Kamal A Saeed
(74) *Attorney, Agent, or Firm* — Knobbe, Martens, Olson & Bear, LLP

(57) ABSTRACT

This application relates to a composition for preventing, treating, and improving skeletal muscle atrophy, the composition including an organoselenium compound. The composition recovered the thickness of muscle fiber reduced by dexamethasone treatment. In addition, the treatment of mice in a muscle loss model showed that the composition had an effect of reducing damaged muscle and of restoring muscle mass. Therefore, it is expected that the composition can be effectively used for the treatment, prevention, or improvement of muscle atrophy.

8 Claims, 77 Drawing Sheets
Specification includes a Sequence Listing.

Control

Dexamethasone

Vehicle 100 mM MI

SEQUENCE LISTING

```
<160> NUMBER OF SEQ ID NOS: 16

<210> SEQ ID NO 1
<211> LENGTH: 21
<212> TYPE: DNA
<213> ORGANISM: Artificial Sequence
<220> FEATURE:
<223> OTHER INFORMATION: forward primer of Myf5

<400> SEQUENCE: 1
agctgggcag aatacgtgct t                                        21

<210> SEQ ID NO 2
<211> LENGTH: 22
<212> TYPE: DNA
<213> ORGANISM: Artificial Sequence
<220> FEATURE:
<223> OTHER INFORMATION: reverse primer of Myf5

<400> SEQUENCE: 2
agaacaggca gaggagaatc ca                                       22

<210> SEQ ID NO 3
<211> LENGTH: 21
<212> TYPE: DNA
<213> ORGANISM: Artificial Sequence
<220> FEATURE:
<223> OTHER INFORMATION: forward primer of Pax7

<400> SEQUENCE: 3
ccctttcaaa gaccaaatgc a                                        21

<210> SEQ ID NO 4
<211> LENGTH: 20
<212> TYPE: DNA
<213> ORGANISM: Artificial Sequence
<220> FEATURE:
<223> OTHER INFORMATION: reverse primer of Pax7

<400> SEQUENCE: 4
ccctcacggg cagatcatta                                          20

<210> SEQ ID NO 5
<211> LENGTH: 20
<212> TYPE: DNA
<213> ORGANISM: Artificial Sequence
<220> FEATURE:
<223> OTHER INFORMATION: forward primer of Myog

<400> SEQUENCE: 5
agcgcaggct caagaaagtg                                          20
```

<210> SEQ ID NO 6
<211> LENGTH: 19
<212> TYPE: DNA
<213> ORGANISM: Artificial Sequence
<220> FEATURE:
<223> OTHER INFORMATION: reverse primer of Myog

<400> SEQUENCE: 6
ccgcctctgt agcggagat                                              19

<210> SEQ ID NO 7
<211> LENGTH: 20
<212> TYPE: DNA
<213> ORGANISM: Artificial Sequence
<220> FEATURE:
<223> OTHER INFORMATION: forward primer of Gapdh

<400> SEQUENCE: 7
ctccactcac ggcaaattca                                             20

<210> SEQ ID NO 8
<211> LENGTH: 20
<212> TYPE: DNA
<213> ORGANISM: Artificial Sequence
<220> FEATURE:
<223> OTHER INFORMATION: reverse primer of Gapdh

<400> SEQUENCE: 8
gcctcacccc atttgatgtt                                             20

<210> SEQ ID NO 9
<211> LENGTH: 23
<212> TYPE: DNA
<213> ORGANISM: Artificial Sequence
<220> FEATURE:
<223> OTHER INFORMATION: forward primer of Myh2

<400> SEQUENCE: 9
gatcaccacg aacccatatg att                                         23

<210> SEQ ID NO 10
<211> LENGTH: 23
<212> TYPE: DNA
<213> ORGANISM: Artificial Sequence
<220> FEATURE:
<223> OTHER INFORMATION: Reverse primer of Myh2

<400> SEQUENCE: 10
ttcatgttcc cataatgcat cac                                         23

<210> SEQ ID NO 11
<211> LENGTH: 22
<212> TYPE: DNA
<213> ORGANISM: Artificial Sequence
<220> FEATURE:
<223> OTHER INFORMATION: forward primer of Foxo3

<400> SEQUENCE: 11
tggagtccat catccgtagt ga                                          22

<210> SEQ ID NO 12
<211> LENGTH: 23
<212> TYPE: DNA
<213> ORGANISM: Artificial Sequence
<220> FEATURE:
<223> OTHER INFORMATION: reverse primer of Foxo3

```
<400> SEQUENCE: 12
ctggtaccca gctttgagat gag                                              23

<210> SEQ ID NO 13
<211> LENGTH: 22
<212> TYPE: DNA
<213> ORGANISM: Artificial Sequence
<220> FEATURE:
<223> OTHER INFORMATION: Forward primer of Impa1

<400> SEQUENCE: 13
agctgtttca attggcttcc tt                                               22

<210> SEQ ID NO 14
<211> LENGTH: 23
<212> TYPE: DNA
<213> ORGANISM: Artificial Sequence
<220> FEATURE:
<223> OTHER INFORMATION: reverse primer of Impa1

<400> SEQUENCE: 14
gccggtgtac atcttatctt cca                                              23

<210> SEQ ID NO 15
<211> LENGTH: 20
<212> TYPE: DNA
<213> ORGANISM: Artificial Sequence
<220> FEATURE:
<223> OTHER INFORMATION: forward primer of Impa2

<400> SEQUENCE: 15
tccccactgt ggcagttagc                                                  20

<210> SEQ ID NO 16
<211> LENGTH: 18
<212> TYPE: DNA
<213> ORGANISM: Artificial Sequence
<220> FEATURE:
<223> OTHER INFORMATION: reverse primer of Impa2

<400> SEQUENCE: 16
ccctcctgcc ggtgtaca                                                    18
```

COMPOSITION COMPRISING ORGANOSELENIUM COMPOUND FOR TREATMENT OF SKELETAL MUSCLE ATROPHY

INCORPORATION BY REFERENCE OF MATERIAL IN ASCII TEXT FILE

This application incorporates by reference the Sequence Listing contained in the following ASCII text file being submitted concurrently herewith: File Name: Sequence_Listing_ISU019-001AUS.txt; created Sep. 8, 2021, 3,575 bytes in size.

BACKGROUND

Field

The present disclosure relates to a composition for preventing, treating, or improving skeletal muscle atrophy, the composition including an organoselenium compound.

Description of the Related Technology

A disease in which a gradual decrease in the whole-body muscle occurs is called muscle atrophy, and the causes thereof include metabolic disorders, hormonal imbalance, and aging. Muscle atrophy is classified into skeletal muscle atrophy and spinal muscular atrophy. The number of patients suffering skeletal muscle atrophy is rapidly increasing due to population aging and rapid changes in dietary habits, and it is emerging as a serious social problem.

SUMMARY

An objective of the present disclosure is to provide a pharmaceutical composition for preventing or treating skeletal muscle atrophy, the composition including an organoselenium compound as an active ingredient.

Another objective of the present disclosure is to provide a food composition for preventing or improving skeletal muscle atrophy, the composition including an organoselenium compound as an active ingredient.

To achieve the objectives of the present disclosure, the present disclosure provides a pharmaceutical composition for preventing or treating skeletal muscle atrophy, the composition including a compound represented by Formula 1 shown below, a stereoisomer thereof, or a pharmaceutically approved salt thereof, as an active ingredient.

[Formula 1]

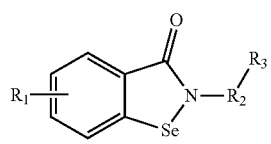

In Formula 1, $R_1$ is selected from the group consisting of hydrogen, halogen, $C_1$-$C_4$ alkyl, $C_1$-$C_4$ alkoxy, $C_1$-$C_4$ hydroxyalkyl, $C_1$-$C_4$ cyanoalkyl, $C_1$-$C_4$ haloalkyl, hydroxy, cyano, and halogen, $R_2$ is $C_1$-$C_4$ alkyl or a single bond, and $R_3$ is $C_5$-$C_7$ aryl or heteroaryl, wherein at least one hydrogen atom (H) of the aryl the heteroaryl may be substituted with $C_1$-$C_4$ alkyl, $C_1$-$C_4$ alkoxy, $C_1$-$C_4$ haloalkyl, $C_1$-$C_4$ hydroxyalkyl, $C_1$-$C_4$ cyanoalkyl, hydroxy, cyano, or halogen.

In addition, the present disclosure provides a food composition for preventing or improving skeletal muscle atrophy, the composition including a compound represented by Formula 1 shown below, a stereoisomer, or a salt thereof, as an active ingredient.

[Formula 1]

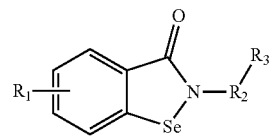

In Formula 1, $R_1$ is selected from the group consisting of hydrogen, halogen, $C_1$-$C_4$ alkyl, $C_1$-$C_4$ alkoxy, $C_1$-$C_4$ hydroxyalkyl, $C_1$-$C_4$ cyanoalkyl, $C_1$-$C_4$ haloalkyl, hydroxy, cyano, and halogen, $R_2$ is $C_1$-$C_4$ alkyl or a single bond, and $R_3$ is $C_5$-$C_7$ aryl or heteroaryl, {wherein at least one hydrogen atom (H) of the aryl or heteroaryl can be substituted with $C_1$-$C_4$ alkyl, $C_1$-$C_4$ alkoxy, $C_1$-$C_4$ haloalkyl, $C_1$-$C_4$ hydroxyalkyl, $C_1$-$C_4$ cyanoalkyl, hydroxy, cyano, or halogen}. In one embodiment of the present disclosure, $R_1$ may be hydrogen or $C_1$-$C_4$ alkyl, $R_2$ may be a single bond, and $R_3$ may be $C_6$ aryl or heteroaryl {wherein at least one hydrogen atom (H) of the aryl or heteroaryl may be substituted with $C_1$-$C_4$ alkyl}.

In one embodiment of the present disclosure, $R_1$ may be hydrogen or $C_1$-$C_4$ alkyl, $R_2$ may be a single bond, and $R_3$ may be phenyl, {wherein at least one hydrogen atom (H) of the phenyl may be substituted with $C_1$-$C_4$ alkyl}.

In one embodiment of the present disclosure, the compound of Formula 1 may be a compound represented by Formula 2 shown below.

[Formula 2]

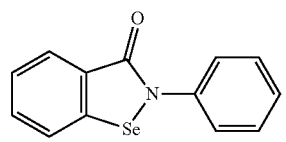

In one embodiment of the present disclosure, the skeletal muscle atrophy may be sarcopenia.

The results of in vitro experiments showed that the compound of the present disclosure recovered the thickness of muscle myotubes reduced by dexamethasone treatment, and the results of treatment of mice in a muscle loss model showed that the compound had an effect of reducing damaged muscle and of restoring muscle mass and function. Therefore, it is expected that the composition of the present disclosure can be effectively used for the treatment, prevention, or improvement of muscle atrophy.

BRIEF DESCRIPTION OF THE DRAWINGS

The above and other objectives, features, and other advantages of the present disclosure will be more clearly understood from the following detailed description taken in conjunction with the accompanying drawings, in which.

DETAILED DESCRIPTION

Figure 1A:
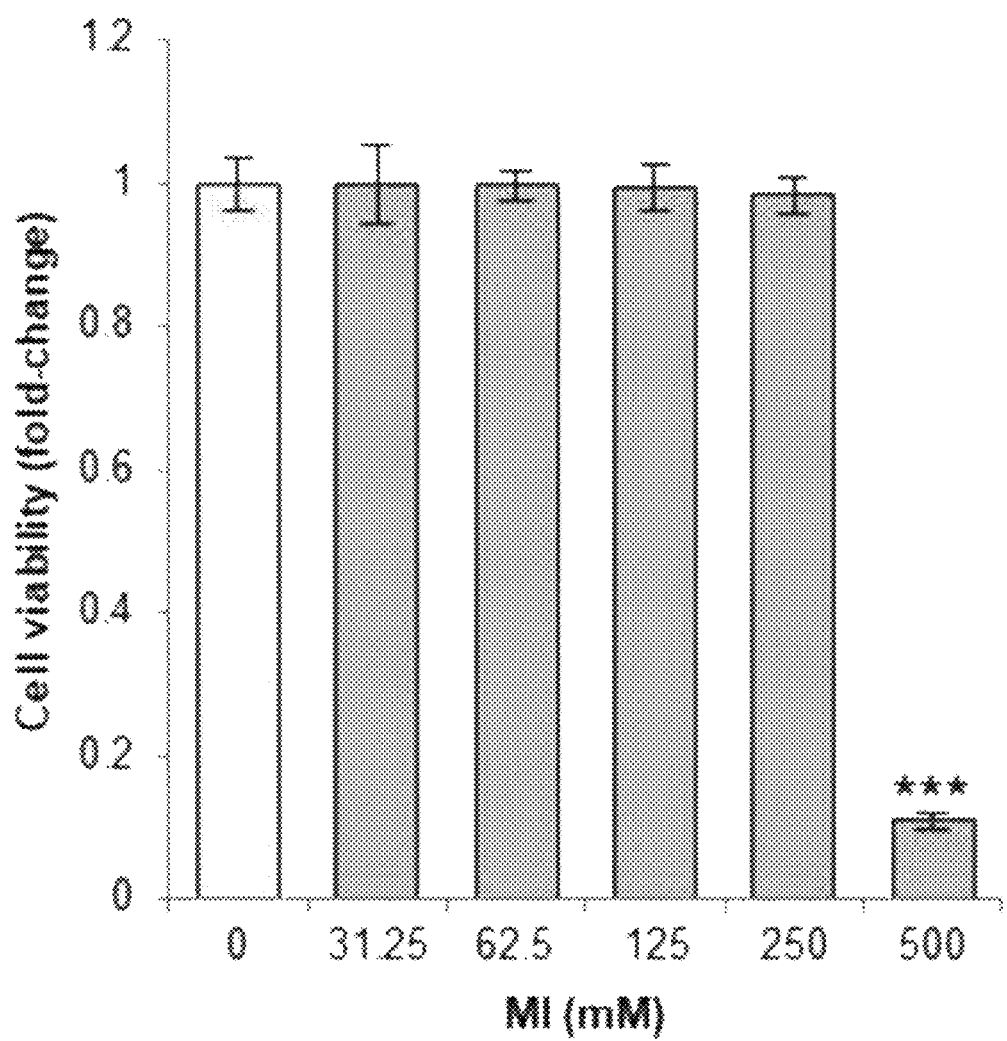
FIG. 1A shows the result of an MTT assessment of the cultures treated with myo-inositol for 48 hours after 96-hour incubation in differentiation culture media (DM; i.e., DMEM supplemented with 2% horse serum (HS) and 1% penicillin and streptomycin (PenStrep))
Figure 1B:
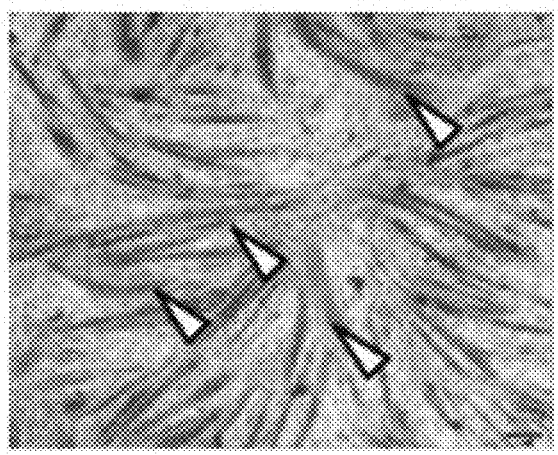
FIG. 1B is a micrograph of H&E-stained C2C12 myoblast cultures treated with 10 μM dexamethasone alone or a combination of 10 μM dexamethasone and 100 mM myo-inositol after 72 hours of incubation with DM (scale bar=100 μm)
Figure 1B:
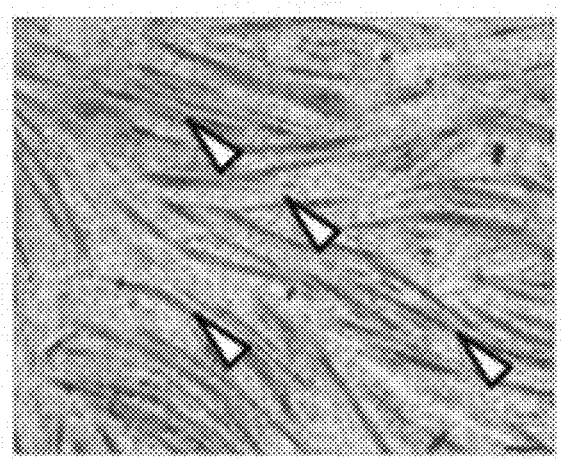
Figure 1B:
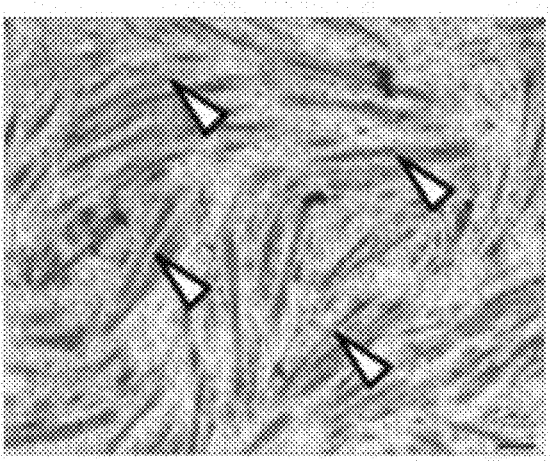
Figure 1C:
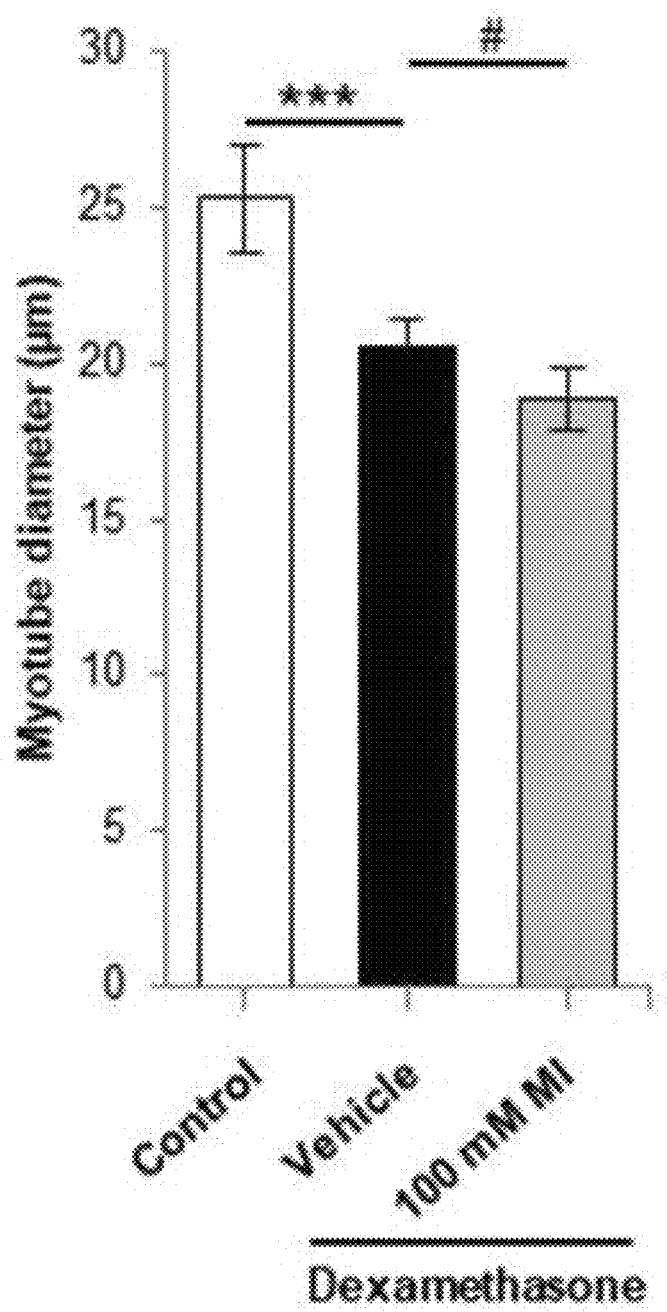
FIG. 1C shows the average myotube diameter of the cultures treated with dexamethasone and myo-inositol (***=p<0.001, #=p<0.05)
Figure 1D:
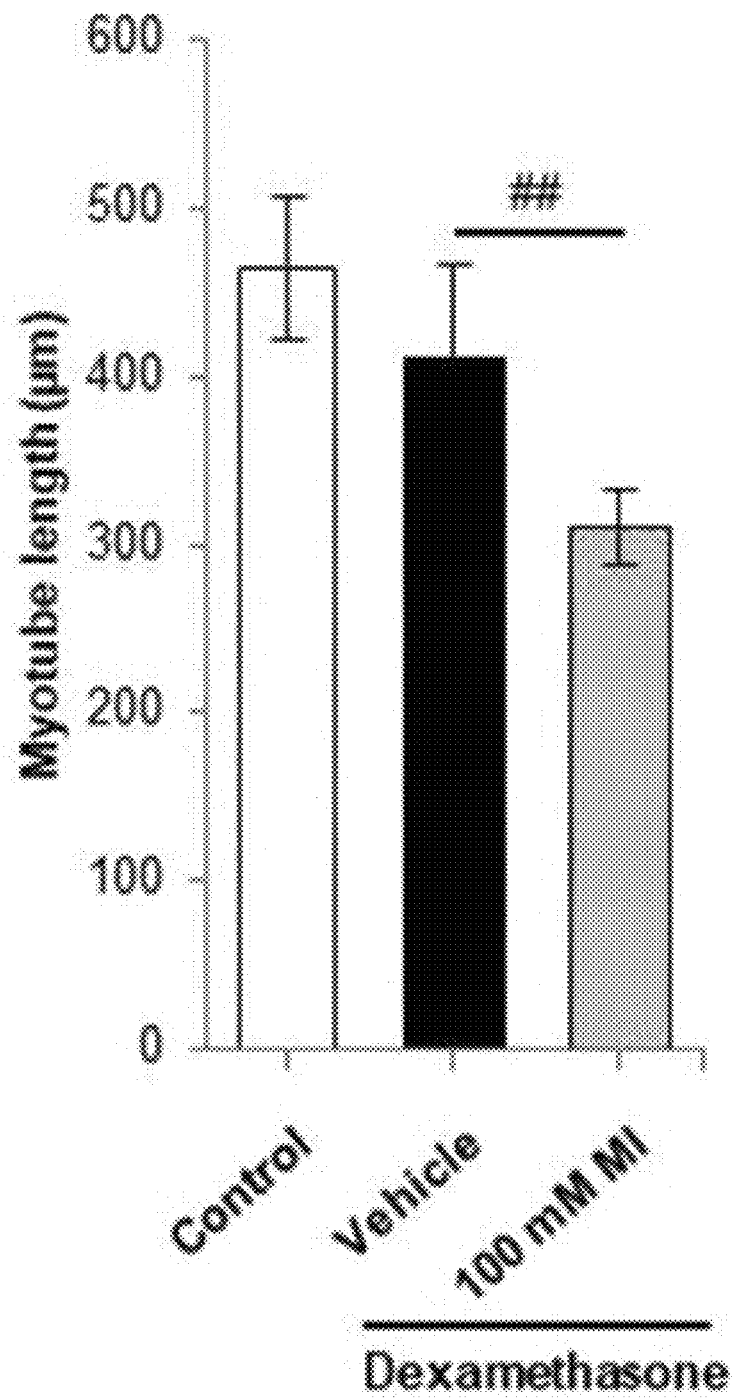
FIG. 1D shows the average myotube length of the cultures co-treated with dexamethasone and myo-inositol (##=p<0.01)
Figure 1E:
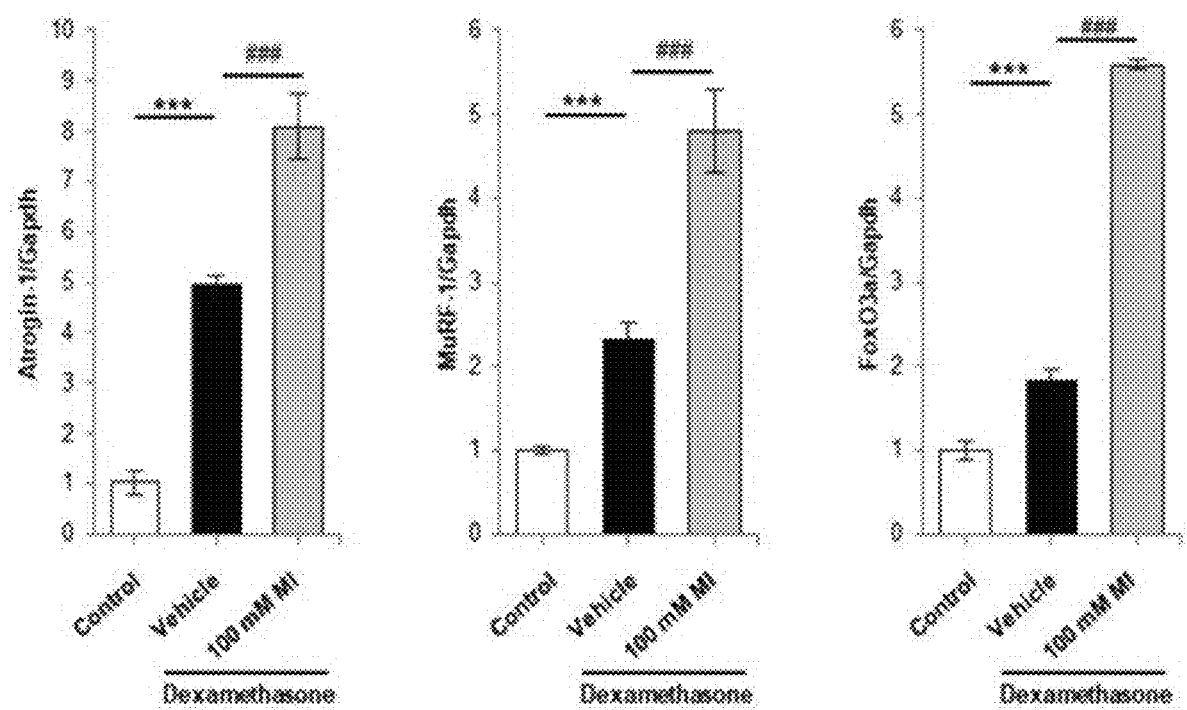
FIG. 1E shows the result of qPCR analysis on Atrogin-1 expression, MuRF-1 expression, and FoxO3a expression (***=p<###=p<0.001)

Representative types of skeletal muscle atrophy include sarcopenia and disease-related muscle wasting. When patients suffer from the disease, a gradual loss in muscle function and muscle mass occurs because the normal muscle regeneration cannot be performed after muscle function reduction. At present, only symptomatic therapy and exercise therapy are available for the disease, and there are no other effective treatments. In particular, although sarcopenia was given an FDA disease code in 2016, there is still no effective drug for the treatment of sarcopenia. Therefore, a discovery for drugs for the treatment of sarcopenia is urgently needed.

An objective of the present disclosure is to provide a pharmaceutical composition for preventing or treating skeletal muscle atrophy, the composition including a compound represented by Formula 1 as an active ingredient.

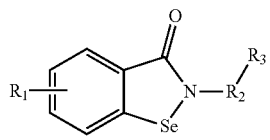

[Formula 1]

In Formula 1, $R_1$ is selected from the group consisting of hydrogen, halogen, $C_1$-$C_4$ alkyl, $C_1$-$C_4$ alkoxy, $C_1$-$C_4$ hydroxyalkyl, $C_1$-$C_4$ cyanoalkyl, $C_1$-$C_4$ haloalkyl, hydroxy, cyano, and halogen, $R_2$ is $C_1$-$C_4$ alkyl or a single bond, and $R_3$ is $C_5$-$C_7$ aryl or heteroaryl, wherein at least one hydrogen atom (H) of the aryl or heteroaryl may be substituted with $C_1$-$C_4$ alkyl, $C_1$-$C_4$ alkoxy, $C_1$-$C_4$ haloalkyl, $C_1$-$C_4$ hydroxyalkyl, $C_1$-$C_4$ cyanoalkyl, hydroxy, cyano, or halogen.

In one embodiment of the present disclosure, $R_1$ may be hydrogen or $C_1$-$C_4$ alkyl, $R_2$ may be a single bond, and $R_3$ may be $C_6$ aryl or heteroaryl {wherein at least one hydrogen atom (H) of the aryl or heteroaryl may be substituted with $C_1$-$C_4$ alkyl}.

In one embodiment of the present disclosure, $R_1$ may be hydrogen or $C_1$-$C_4$ alkyl, $R_2$ may be a single bond, and $R_3$ may be phenyl, {wherein at least one hydrogen atom (H) of the phenyl may be substituted with $C_1$-$C_4$ alkyl}.

In one embodiment of the present disclosure the compound of Formula 1 may be a compound represented by Formula 2 shown below.

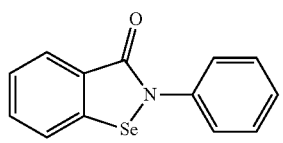

[Formula 2]

The compound represented by Formula 2 is ebselen, and although it has been approved by the FDA to have antifungal efficacy, the treatment effect on muscle atrophy is not known yet.

In the present disclosure, L-690,330 is [1-(4-hydroxyphenoxy)-1-phosphonoethyl]phosphonic acid and has a structure as shown in Formula 3 below, and L-690,330 or a salt thereof has an effect of preventing, improving, or treating skeletal muscle atrophy.

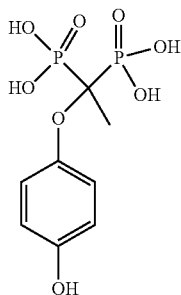

[Formula 3]

Throughout the specification, when defining the compound of Formula 1, the concepts defined as follows are used. The following definitions also apply to terms used individually or as part of a larger group throughout this specification, unless specifically indicated otherwise.

The term "alkyl", when used alone or in combination with heteroalkyl, means a straight-chain, branched-chain or cyclic hydrocarbon radical, wherein each carbon atom can be substituted with one or more groups selected from among cyano, hydroxy, alkoxy, oxo, halogen, carbonyl, sulfonyl, cyanyl, and the like.

The term "alkoxy" refers to —O-alkyl, wherein the term "alkyl" is as defined above.

The term "heteroalkyl" refers to an alkyl containing at least one hetero atom selected from among N, O, and S.

The term "aryl" refers to an aromatic group, including phenyl, naphthyl, and the like, and may be optionally substituted with one or more alkyl, alkoxy, halogen, hydroxy, carbonyl, sulfonyl, cyanyl, and the like.

The term "heteroaryl" refers to a 5- to 7-membered aromatic monocyclic ring, 8- to 12-membered bicyclic ring, or 11- to 14-membered tricyclic ring, wherein: the 5- to 7-membered aromatic monocyclic ring contains one or more, for example, 1 to 4, or in some embodiments, 1 to 3, heteroatoms selected from among N, O, and S, and contains carbon atoms as the remaining ring atoms; the 8- to 12-membered bicyclic ring contains one or more, for example 1 to 4, or, in some embodiments, 1 to 3, heteroatoms selected from among N, O, and S and contains carbon atoms as the remaining ring atoms, in which at least one ring is an aromatic ring and at least one heteroatom is present in the aromatic ring; and the 11- to 14-membered tricyclic ring contains one or more, for example 1 to 4, or in some embodiments 1 to 3, heteroatoms selected from among N, O, and S and contains carbon atoms as the remaining ring atoms, in which at least one ring is an aromatic ring and at least one heteroatom is present in the aromatic ring. Examples of the heteroaryl group include pyridyl, pyrazinyl, 2,4-pyrimidinyl, 3,5-pyrimidinyl, 2,4-imidazolyl, isoxazolyl, oxazolyl, triazolyl, thiadiazolyl, tetrazolyl, thienyl, benzothienyl, furyl, benzofuryl, benzoimidazolyl, indolyl, indolinyl, pyrrolyl, thiophenyl, pyridizinyl, triazolyl, quinolinyl, pyrazolyl, pyrrolopyridinyl, pyrazolopyridinyl, benzoxazolyl, and benzothiazolyl.

Examples of the heteroaryl group further include zolyl and but are not limited thereto.

The term "heterocycloalkyl" refers to a saturated or partially saturated or aromatic form that contains 1 to 4 heteroatoms selected from among N, O, S and which may optionally be fused with benzo or cyclo alkyl. Examples of suitable heterocycloalkyl include, but are not limited to, piperidinyl, piperazinyl, tetrahydrofuranyl, pyrrolidinyl, pyranyl, and the like.

The term "halo(gen)" refers to a substituent selected from among fluoro, chloro, bromo, and iodo.

In the present disclosure, the expression that $R_2$ is a single bond means that a nitrogen atom and $R_3$ are directly joined.

In addition, terms and abbreviations used herein have their original meanings unless otherwise defined.

On the other hand, the compounds according to the present disclosure may have asymmetric carbon atoms and may exist as R or S isomers, racemates, diastereomeric mixtures, and individual diastereomers, and all these isomers and mixtures fall within the scope of the present disclosure. That is, when asymmetric carbon atoms are included in the structure of Formula 1, it should be understood that all stereoisomers are included unless the direction is otherwise described.

In the present disclosure, the term "skeletal muscle atrophy" refers to diseases that cause the loss of skeletal muscle mass and muscle weakness due to extrinsic factors such as metabolic disorders, hormonal imbalance, and aging, unlike spinal muscle atrophy which causes muscle weakness due to functional impairment of motor neurons.

In the present disclosure, the expression "a thing is pharmaceutically acceptable" means that it is physiologically acceptable, and that it does not normally cause allergic reactions such as gastrointestinal disorders, dizziness, or similar reactions when administered to humans, and that the ordinarily skilled in the art can commonly use it for manufacture of pharmaceutical formulations.

In the present disclosure, a pharmaceutically acceptable salt refers to a salt prepared from a non-toxic metal salt or organic base.

As used herein, the term "salt" may be an acid addition salt formed from a pharmaceutically acceptable free acid. The acid addition salts include: salts of inorganic acids such as hydrochloric acid, nitric acid, phosphoric acid, sulfuric acid, hydrobromic acid, hydroiodic acid, nitrous acid, and phosphorous acid, include aliphatic; mono- and di-carboxylates; phenyl-substituted alkanoates; hydroxy alkanoates; alkanedioates; and salts obtained from non-toxic organic acids such as aromatic acids, aliphatic sulfonic acids, and aromatic sulfonic acids. Examples of the pharmaceutically non-toxic salts include sulfate, pyrosulfate, bisulfate, sulfide, bisulfide, nitrate, phosphate, monohydrogen phosphate, dihydrogen phosphate, methaphosphate, pyrophosphate chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, butyne-1,4-dionate, hexane-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzene sulfonate, xylenesulfonate, phenylacetate, phenylpropionate, phenylbutyrate, citrate, lactate, β-hydroxybutyrate, glycolate, malate, tartrate, methanesulfonate, propanesulfonate, naphthalene-1-sulfonate, naphthalene-2-sulfonate, or mandelate, but are not limited thereto.

The acid addition salt according to the present disclosure may be prepared by a general method. For example, the acid addition salt may be prepared by dissolving the compound represented by Formula 1 in a large amount of an acidic aqueous solution and precipitating a salt with a water-miscible organic solvent such as methanol, ethanol, acetone, or acetonitrile. Alternatively, the acid addition salt may be prepared by evaporating the solvent or excess acid from the mixture, and then drying the mixture or by suction-filtering the precipitated salt.

In addition, a pharmaceutically acceptable metal salt may be prepared using a base. An alkaline metal or alkaline earth metal salt may be prepared, for example, by dissolving the compound in an excessive alkaline metal hydroxide or alkaline earth metal hydroxide solution, filtering non-soluble compound salt, and evaporating and drying the filtrate. In this case, as the metal salt, it is pharmaceutically suitable to prepare a sodium, potassium, or calcium salt. In addition, a silver salt may be obtained by reacting the alkaline metal or alkaline earth metal salt with a suitable anionic salt (for example, silver nitrate).

As used herein, the term "prophylaxis" or "prevention" refers to any action that suppresses the progress of skeletal muscular dystrophy or delays the onset of skeletal muscle atrophy by administration of the pharmaceutical composition according to the present disclosure.

As used herein, the term "treatment" refers to any action in which the symptoms of skeletal muscle atrophy are improved or beneficially changed by administration of the pharmaceutical composition according to the present disclosure.

The pharmaceutical composition according to the present disclosure includes the compound represented by Formula 1 as an active ingredient and may include a pharmaceutically acceptable carrier. The pharmaceutically acceptable carrier is a carrier commonly used in formulations, and examples thereof include, but are not limited to, saline, sterile water, Ringer's solution, buffered saline, cyclodextrin, dextrose solution, maltodextrin solution, glycerol, ethanol, liposome, and the like. If necessary, other conventional additives such as antioxidants and buffers may be added thereto if necessary. In addition, diluents, dispersants, surfactants, binders, lubricants and the like may be additionally added to make the composition of the present disclosure as injectable formulations such as an aqueous solution, suspension, and emulsion, or make the composition of the present disclosure as pills, capsules, granules, or tablets. Regarding suitable pharmaceutically acceptable carriers and formulations, formulations can be preferably made according to each component using the method disclosed in Remington's literature. The pharmaceutical composition of the present disclosure is not particularly limited in formulations but may be preferably formulated as injections or oral medications.

The pharmaceutical composition of the present disclosure may be administered orally or administered parenterally (for example, intravenously or subcutaneously) as desired, and the dosage may vary depending on the patient's condition and weight, the severity of disease, drug form, the route and time of administration, and may be appropriately selected by those skilled in the art.

The composition according to the present disclosure is administered in a pharmaceutically effective dosage. In the present disclosure, the pharmaceutically effective dosage means an amount that is sufficient to treat a disease with a reasonable benefit/risk ratio applicable to medical treatment, and the effective dosage depends on various factors including the type and severity of a disease, drug activity on the disease, patient's sensitivity to drug, administration time, administration route, excretion rate, treatment period, and co-used drugs and other factors well known in the medical field. The composition according to the present disclosure may be administered as an individual therapeutic agent or administered in combination with other therapeutic agents. When administered in combination, the composition and other therapeutic agents may be administered sequentially or simultaneously. The composition may be administered as a single dose or multiple doses. In consideration of all of the above factors, it is important to administer a dosage that can obtain the maximum efficacy with a minimum amount without side effects, and the dose can be easily determined by those skilled in the art.

Specifically, the effective amount of the composition according to the present disclosure may vary depending on the age, sex, and weight of the patient and may be increased or decreased depending on the administration route, the severity of the disease, and the sex, weight, age, and the like of the patient.

The present disclosure provides a food composition for preventing or improving skeletal muscle atrophy, the composition including a compound represented by Formula 1 shown below, a stereoisomer, or a salt thereof, as an active ingredient.

[Formula 1]

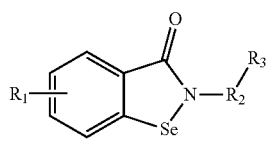

In Formula 1, $R_1$ is selected from the group consisting of hydrogen, halogen, $C_1$-$C_4$ alkyl, $C_1$-$C_4$ alkoxy, $C_1$-$C_4$ hydroxyalkyl, $C_1$-$C_4$ cyanoalkyl, $C_1$-$C_4$ haloalkyl, hydroxy, cyano, and halogen, $R_2$ is $C_1$-$C_4$ alkyl or a single bond, and $R_3$ is $C_5$-$C_7$ aryl or heteroaryl, wherein at least one hydrogen atom (H) of the aryl or heteroaryl may be substituted with $C_1$-$C_4$ alkyl, $C_1$-$C_4$ alkoxy, $C_1$-$C_4$ haloalkyl, $C_1$-$C_4$ hydroxyalkyl, $C_1$-$C_4$ cyanoalkyl, hydroxy, cyano, or halogen.

The description of the compound of Formula 1, the salt, and the like are the same as described above.

The food composition includes a health functional food composition.

As used herein, the term "improvement" refers to any action that reduces at least one parameter related to a condition to be treated, for example, the degree of a symptom.

In the food composition of the present disclosure, the active ingredient may be added to food as it is or may be used together with other food or food ingredients. That is, the active ingredient may be appropriately used according to a conventional method. The mixing ratio of the active ingredient may be appropriately determined depending on the purpose of its use (for prevention or improvement). In general, for the production of food or beverage, the composition of the present disclosure is added in an amount of 15% by weight or less, preferably 10% by weight or less, based on the amount of the raw material. However, in the case of long-term ingestion for health and hygiene or health control, the amount may be less than or equal to the above range.

The health functional food composition of the present disclosure is not particularly limited in other ingredients except for the active ingredient being included as an essential ingredient in the indicated ratio described above, and may contain various flavoring agents or natural carbohydrates as additional ingredients as in conventional beverages. Examples of the natural carbohydrate include: monosaccharides such as glucose, fructose and the like; disaccharides such as maltose, sucrose, and the like; and polysaccharides such as conventional sugars (for example, dextrin and cyclodextrin) and sugar alcohols such as xylitol, sorbitol, and erythritol. Aside from those ingredients, as flavoring agents, natural flavoring agents (taumatin, *stevia* extract (for example, rebaudioside A, glycyrrhizin, etc.) and synthetic flavoring agents (saccharin, aspartame, etc.) may be advantageously used. The ratio of the natural carbohydrate may be appropriately determined by those skilled in the art.

Aside from the ingredients described above, the health functional food composition of the present disclosure may include various nutrients, vitamins, minerals (electrolytes), flavoring agents including synthetic flavoring agents and natural flavoring agents, coloring agents, taste and flavor enhancers (cheese, chocolate, etc.), pectic acid and salts thereof, alginic acid and salts thereof, organic acids, protective colloidal thickeners, pH adjusters, stabilizers, preservatives, glycerin, alcohols, carbonation agents used in carbonated beverages, and the like. These components may be used solely or in combination. The proportion of these additives may also be appropriately selected by those skilled in the art.

The present disclosure provides a method for preventing or treating skeletal muscle atrophy, the method including a step of administering to a subject a pharmaceutical composition including a compound represented by Formula 1.

The term "subject" used in the present disclosure refers to an animal and may be a mammal capable of exhibiting beneficial effects when treated with the composition of the present disclosure. Preferred examples of the subject may include primates such as humans. In addition, examples of the subject may include all subjects exhibiting symptoms of muscle atrophy or at risk of muscle atrophy.

The present disclosure provides a use of a pharmaceutical composition containing a compound represented by Formula 1 as an active ingredient, the use being to prevent or treat skeletal muscle atrophy.

The descriptions related to the compound, composition, treatment method, and therapeutic use may be applied in the same manner as long as they do not contradict each other.

Hereinbelow, examples will be described to aid in understanding the present disclosure. However, the examples described below are provided only to facilitate the understanding of the present disclosure and thus the details in the examples should not be construed to limit the scope of the present disclosure.

Example 1: Raw Material and Test Method

Example 1-1: Reagent

Dexamethasone and L-690,330 were purchased from Santa Cruz Biotechnology, and ebselen was purchased from Tokyo Chemical Industry Co. Ltd. (in Japan). MitoTracker Red CMX-Ros was purchased from Invitrogen (in USA), and LiCl was purchased from Sigma-Aldrich. 6-Bromoindirubin-3-oxime (BIO) was provided by Professor Yong-Chul Kim from Gwangju Institute of Science and Technology (in Korea), and myo-inositol was purchased from MP Biomedicals. Puromycin was purchased from Abcam, and glycerol was purchased from Wako Chemicals. Antibodies were purchased against myosin heavy chain 2 (sc-53095, Santa Cruz Biotechnology, USA; dilution=1:1000), forkhead box 0-3 (Fox03a) (12829S, Cell Signaling Technology, USA; immunoblotting dilution=1:1000, immunocytochemistry dilution=1:400), glyceraldehyde 3-phosphate dehydrogenase (GAPDH) (sc-365062, Santa Cruz Biotechnology; dilution=1:1000), IMPase 1 (ab202131, Abcam; dilution=1:1000), and puromycin (MABE343, Millipore, USA; dilution)=1:25000).

Example 1-2: Cell Cultivation $C_2C_{12}$ mouse skeletal muscle progenitor cells (myoblasts) were grown in a growth medium including Dulbecco's Modified Eagle's Medium (DMEM) supplemented with 10% fetal bovine serum (FBS), 50 units/mL if penicillin, and 50 mg/mL of streptomycin (PenStrep).

Then, the myoblasts were treated with a differentiation medium (DMEM supplemented with 2% horse serum and PenStrep) for 72 hours so that the myoblasts were induced to differentiate into myotubes.

Example 1-3: Differentiation of Myoblast and Treatment of Myotube $C_2C_{12}$ myoblasts were seeded onto 6-well plates in a growth medium (GM). After reaching confluence, the cultures were treated with DM for 72 hours, and myotube atrophy was induced with DM containing 10 μM dexamethasone for 24 hours in the presence or absence of the drug of interest. Myotubes were visualized using hematoxylin and eosin staining according to a previously published protocol, and imaged with an optical microscope (Olympus CKX41, Japan). A myotube distribution was calculated by dividing the number of myotubes in each group by the total number of myotubes per image.

Example 1-4: MTT Assay

Cell proliferation was evaluated through MTT (3-(4,5-dimethylthiazol-2-yl)-2,5-diphenyltetrazolium bromide) assay as described above. Myoblasts were seeded 3 times into 96-well plates at a density of 2×10 3 cells per well. A compound to be tested was added, followed by 48 hours of incubation, the medium was changed to an MTT solution (0.5 mg/mL, final concentration), and the plate was incubated in an incubator at 37° C., 5%, $CO_2$ conditions. After 60 minutes of incubation, 50 μL of DMSO was added. Optical density in each well was measured at 570 nm using a microplate reader (VersaMax, Molecular Devices, USA). For myotube analysis, myoblasts were differentiated for 96 hours, the medium was supplemented with the compound of interest, 48 hours of incubation was additionally performed, and the cultures were assayed.

Example 1-5: INPase Activity Assay

IMPase activity in cells and tissues was measured using a myo-inositol assay kit (Megazyme, Ireland) according to the manufacturer's instructions. The cell supernatant was sonicated in PBS for 90 seconds with a 30-second on and 15-second off cycle (Vibra-Cell, USA) as described above, and then centrifuged at 13,000×g for 15 minutes as described above. Thus, the supernatant was prepared.

Example 1-6: siRNA-Mediated Gene Knockdown siRNA-mediated knockdown of gene expression was performed in a 6-well plate format (Thermo Fischer Scientific, Waltham, USA) according to the manufacturer's protocol. Lipofectamine 3000 formulation (Thermo Fisher Scientific, Waltham, USA) was used in the transfection step.

Example 1-7: Real-time Quantitative PCR

The transcription level of the gene was measured using a StepOnePlus Real Time PCR System (manufactured by Applied Biosystems, UK). cDNA was reverse transcribed from total RNA using an AccuPower RT PreMix (manufactured by Bioneer, USA). Real-time PCR was performed by modifying the manufacturer's instructions as follows.

PCR was performed three times using a total of 20 μL of 2×Power SYBR Green PCR Master Mix containing 200 nM of specific primers and 1 μL of cDNA. 10 minutes of incubation was performed at 95° C. prior to PCR amplification. The amplification consisted of 40 cycles of denaturation (for 15 seconds at 95° C.), annealing (for 1 minute at 60° C.), and extension (for 20 seconds at 72° C.). Extension and fluorescence detection were performed at 72° C. after each cycle. After the final cycle, melting point analysis was performed using continuous fluorescence detection on samples at a temperature in a range of 60° C. to 95° C. Specific cDNA samples were included in each run and used as a reference for comparison between runs. Expression levels of GAPDH were used for normalization and expression levels of all other genes were calculated. Details of the primer are shown in Table 1 below.

TABLE 1

| Gene | Accession number | Direction | Sequence |
| --- | --- | --- | --- |
| Mus musculus myogenic factor 5 (Myf5) | NM_008656 | Forward | AGCTGGGCAGAATACGTGCTT (SEQ ID NO: 1) |
| | | Reverse | AGAACAGGCAGAGGAGAATCCA (SEQ ID NO: 2) |
| Mus musculus paired box 7 (Pax7) | NM_011039 | Forward | CCCTTTCAAAGACCAAATGCA (SEQ ID NO: 3) |
| | | Reverse | CCCTCACGGGCAGATCATTA (SEQ ID NO: 4) |
| Mus musculus myogenin (Myog) | NM_031189 | Forward | AGCGCAGGCTCAAGAAAGTG (SEQ ID NO: 5) |
| | | Reverse | CCGCCTCTGTAGCGGAGAT (SEQ ID NO: 6) |
| Mus musculus glyceraldehyde-3-phosphate dehydrogenase (Gapdh) | NM_001289726 | Forward | CTCCACTCACGGCAAATTCA (SEQ ID NO: 7) |
| | | Reverse | GCCTCACCCCATTTGATGTT (SEQ ID NO: 8) |
| Mus musculus myosin, heavy polypeptide 2, skeletal muscle, adult (Myh2) | NM_001039545 | Forward | GATCACCACGAACCCATATGATT (SEQ ID NO: 9) |
| | | Reverse | TTCATGTTCCCATAATGCATCAC (SEQ ID NO: 10) |
| Mus musculus forkhead box O3 (Foxo3) | NM_019740 | Forward | TGGAGTCCATCATCCGTAGTGA (SEQ ID NO: 11) |
| | | Reverse | CTGGTACCCAGCTTTGAGATGAG (SEQ ID NO: 12) |
| Mus musculus inositol (myo) -1 (or 4) - monophosphatase 1 (Impa1) | NM_018864 | Forward | AGCTGTTTCAATTGGCTTCCTT (SEQ ID NO: 13) |
| | | Reverse | GCCGGTGTACATCTTATCTTCCA (SEQ ID NO: 14) |
| Mus musculus inositol (myo) -1 (or 4) - monophosphatase 2 (Impa2) | NM_053261 | Forward | TCCCCACTGTGGCAGTTAGC (SEQ ID NO: 15) |
| | | Reverse | CCCTCCTGCCGGTGTACA (SEQ ID NO: 16) |

Example 1-8: MitoTracker Red CMX-Ros Staining of Early Myotubes

In differentiation cultures, myotubes were visualized by treatment with 50 nM MitoTracker Red CMX-Ros and 1 mM DAPI in a differentiation medium at 37° C. for 30 minutes and imaged using a fluorescence microscope (Leica DMI3000B, Germany) as described above.

Example 1-9: Morphological Analysis of Myotubes

To evaluate myotube formation and atrophy, five microscopic fields of H&E-stained or MitoTracker Red CMX-Ros-stained cultures were randomly captured, and multinuclear myotube formation and diameters were calculated. Myotubes were designated as multinucleated cells containing three or more nuclei, and the diameters of myotubes were calculated using ImageJ 1.48 software (National Institutes of Health, Bethesda, MD, USA).

Example 1-10: Western Blot

Protein concentrations in cell lysates were quantified using a Bradford reagent (Bio-Rad, USA, CA). After electrophoresis, the separated proteins were transferred to PVDF membranes, blocked with 5% nonfat dry milk in TBST (0.02% Tween 20 in TBS) and 5% bovine serum albumin in TBST (0.02% Tween 20 in TBS), followed by overnight incubation with a primary antibody at 4° C.

A secondary antibody was used in a dilution ratio of 1:10000 and incubated for 35 minutes at room temperature. Densitometry analysis of gel bands was performed using ImageJ 1.48 software (National Institutes of Health).

Example 1-11: Immunocytochemistry

Myoblasts were differentiated into myotubes in 6 well plates. The myotubes were then immunostained for FoxO3a (Cell Signaling Technology, dilution of 1:400). Alexa Fluor 488 goat anti-mouse IgG was used as a secondary antibody (manufactured by Invitrogen). Nuclei were stained using DAPI solution (1 μM dissolved in third distilled water). Staining was visualized by fluorescence microscopy (Leica DMI3000 B).

Example 1-12: In Vitro SUnSET Assay of Protein Synthesis

Surface sensing translation (SUnSET) assay was performed as described above. Briefly, 1 μg/mL puromycin was added to the culture and the harvest was lysed after 10 minutes. For immunoblotting, the myotube extract was treated with anti-puromycin 12D10 antibody (MABE343; Millipore).

Example 1-13: Animal Testing

The study was conducted according to the Guideline for Laboratory Animal Research for the Care and Use of Laboratory Animals and was approved by the Gwangju Science and Technology Animal Care and Use Committee (Study Approval No. GIST-2019-042).

Mice were supplied by Damool Science, Korea.

Example 1-14: Skeletal Muscle Atrophy Dexamethasone Model 13-week-old male $C_{57}BL/6J$ mice were treated with drugs as follows:
1) Injection of vehicle (4% hydroxypropyl-β-cyclodextrin) alone;
2) 15 mg/kg of dexamethasone dissolved in vehicle;
3) 15 mg/kg of dexamethasone and 1 mg/kg of ebselen; and
4) Injection of 15 mg/kg dexamethasone and 3 mg/kg ebselen (n=5 per group).

The muscle condition was evaluated after intraperitoneal injection daily for 14 days with the same drug as above.

Example 1-15: Skeletal Muscle Degenerative Glycerol Model

The glycerol infusion protocol was used to induce muscle degeneration. Male C57BL/6J mice were anesthetized with PBS containing ketamine (22 mg/kg; Yuhan, Republic of Korea) and xylazine (10 mg/kg; Bayer, Republic of Korea), 100 μL glycerol (50% vol/vol) was injected into unilateral gastrocnemius muscle and splenic muscle.

The mice were treated with vehicle (0.5% methyl cellulose) or with vehicle+ebselen (30 mg/kg) via oral gavage every 24 hours (n=6 per group). A muscle fatigue test was performed after 5 days.

Example 1-16: Muscle Fatigue Test

Muscle fatigue was measured using a known protocol (Chiu, et al.). In summary, mice were trained prior to initiating the fatigue task using an accelerated Rotarod (Ugo Basile, Italy). Mice were trained with a Rotarod at a constant speed of 13 rpm for 15 minutes. After 15-minute recovery, mice were placed on a Rotarod adapted to accelerate to 13 to 25 rpm within 3 minutes, for 15 minutes. After 24 hours, the muscle fatigue test was performed with a ramping rate of 13 to 25 rpm within 3 minutes and held at 25 rpm for 30 minutes. For each mouse, a delay time falling from the Rotarod was measured. Mice being tiered were classified as falling 4 times within 1 minute and the test was stopped.

Example 1-17: Grip Strength Test

A grip strength of each mouse was recorded using a BIO-GS3 (Bioseb, USA). To measure the grip strength, mice were placed on a metal grid to grip the metal grid with four paws and were gently pulled back until the mice were unable to continue holding the grid. Muscle strength was expressed using the maximum value obtained from three trials at 1-minute intervals.

Example 1-18: Evaluation of Muscle Endurance through Limb Suspension Test

Mice were placed in the center of a grid, and it was made sure that the grid was gripped by the limbs of the mice. Next, the grid was turned over and hung at a height of 50 cm above a baseline, and the hanging time was measured up to 10 minutes.

Example 1-19: Muscle Sampling and Histological Analysis

Before sacrificing the mice, the mice were anesthetized by intraperitoneal injection of PBS containing ketamine (22 mg/kg; Yuhan Corporation, Korea) and xylazine (10 mg/kg; Bayer, Korea). After sacrificing the mice, the gastrocnemius and splenic muscles of the glycerol injury model were dissected and weighed. For histological analysis, the muscles were incubated overnight with 4% paraformaldehyde at 4° C., fixed, and embedded in paraffin. 5-μm muscle sections were obtained and was stained with H&E using a kit according to the manufacturer's instructions (Merck & Co., USA). Damaged areas and cross-sectional areas were measured using ImageJ 1.48 software (National Institutes of Health).

In the case of the dexamethasone-induced atrophy model, the quadriceps, gastrocnemius and splenic muscles were dissected and weighed. The quadriceps were stained with H&E according to the same protocol used for the glycerol test and used for histological analysis.

Example 1-20: Human Skeletal Myoblast Culture and Experiment

Human skeletal myoblasts were purchased from Thermo-Fisher Scientific. Myoblasts were thawed in a water bath, washed with mL DM, and centrifuged at 180 g for 5 minutes at room temperature. Next, myoblasts were resuspended in DM and seeded in a 12-well plate at a density of 4.8×10 4 cells/well. After 72 hours, the myoblasts were treated with a compound for 24 hours. The myotube diameter was measured by optical microscopy analysis of DIC captured images (Olympus CKX41).

Example 1-21: Statistics

Student's t-test was used to determine the statistical significance of the results of FIGS. 1 to 6 and 9 (Microsoft Excel 2016). Two-way ANOVA was used to confirm the statistical significance of the results of FIGS. 7 and 8 (ANOVA was performed using Data Analysis Tool for Microsoft Excel 2013). Here, p values less than 0.05 were considered statistically significant. Unless otherwise noted, the experiment was performed three times, and error bars are standard deviations.

Example 2: Confirmation of Myotube Atrophy Effect by Myo-inositol

MTT assay was performed to evaluate the effect of myo-inositol on muscle cell viability. Differentiated C2C12 murine myotube cultures were observed while increasing the concentration of Myo-inositol for 48 hours. It was observed that myo-inositol concentrations below 250 mM did not significantly affect cell viability. However, at a concentration of 500 mM, significant cytotoxicity was observed (see FIG. 1A). Based on these data, 100 mM myo-inositol addition was used to study myotube atrophy and myogenesis because it was within the range of cytotoxic concentrations and was significantly lower than the observed cytotoxic concentrations.

To evaluate the effect of myo-inositol on myotube atrophy, differentiated $C_2C_{12}$ cultures were treated with dexamethasone as described above (FIG. 1B). As a result, the treatment with myo-inositol+dexamethasone significantly reduced the average myotube diameter (see FIG. 1C), and also significantly reduced the myotube length (see FIG. 1D), compared to the case of treatment with dexamethasone alone.

Increased skeletal muscle atrophy was associated with increased expression of E3 ubiquitin ligase, atrogin-1 (F-box only protein 32/MAFbx) and MuRF-1 (TRIM63). It is regulated by the fork head box 03 (Fox03a) which is a master transcription factor and is upregulated when muscular atrophy occurs. It was confirmed that dexamethasone treatment increased the expression of atrogin-1, MuRF-1 and Fox03a in myotubes, and myo-inositol treatment further increased the effect of dexamethasone treatment on the expression of atrogin-1, MuRF-1 and Fox03a (see FIG. 1E).

Example 3: Confirmation of Effect of Myo-inositol on Myogenesis Progression and Myotube Morphology Myo-inositol is produced by IMPase which is an enzyme and is expressed in two isoforms, IMPase-1 and IMPase-2. IMPase-1 and -2 were observed to be down-regulated during myoblast differentiation (see FIG. 2A).

The effect of an excessive myo-inositol concentration was evaluated by inducing $C_2C_{12}$ myoblasts to enter myogenesis in DM supplemented with myo-inositol. As a result, it was confirmed that myo-inositol reduced the number of immature myotubes (see FIGS. 2B and 2C).

Myogenesis is associated with down-regulation of Pax7 which is a transcription factor and MyF5 which is a myogenic factor 5 and up-regulation of myogenin (MyoG/myogenic factor 4), a motor protein, and myosin heavy chain II (Myh2). Myo-inositol increased the expression of Pax7 and Myf5 and reduced the expression of MyoG and Myh2 in myoblasts cultured in a differentiation medium (see FIG. 2D).

Figure 2A:
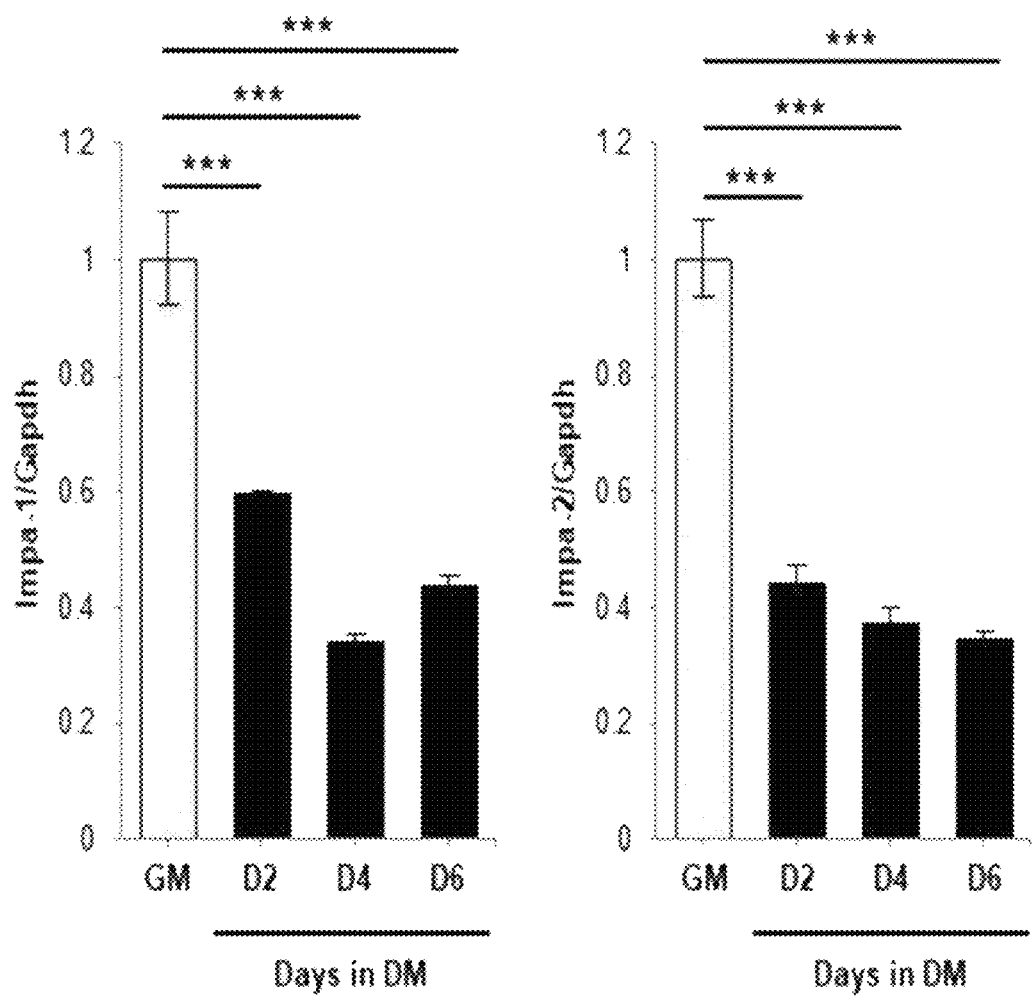
FIG. 2A shows the result of qPCR analysis on IMPase1 expression and IMPase2 expression (***=p<0.01)
Figure 2B:
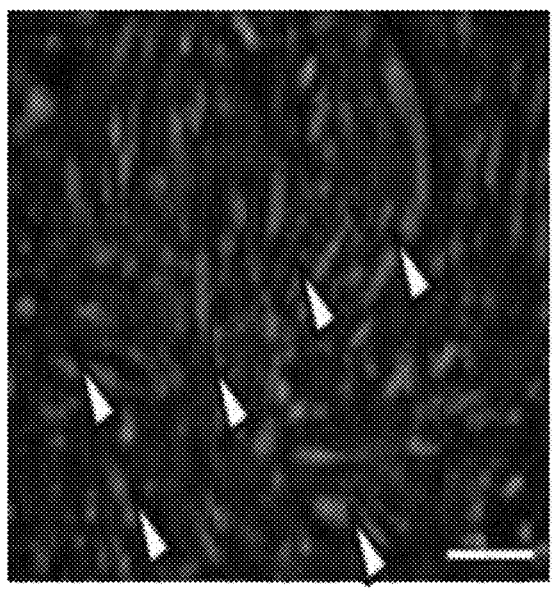
FIG. 2B is a micrograph of MitoTracker Red CMX-Ros-stained myoblast C2C12 cultures after 48 hours of incubation with DM or with 100 mM myo-inositol-added DM (scale bar=100 μm)
Figure 2B:
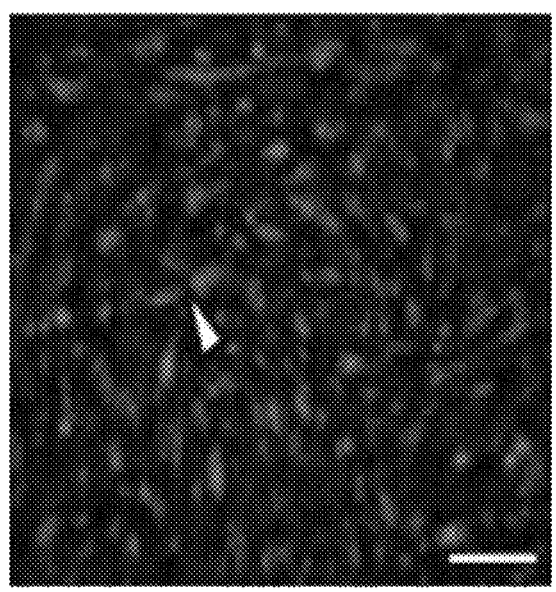
Figure 2C:
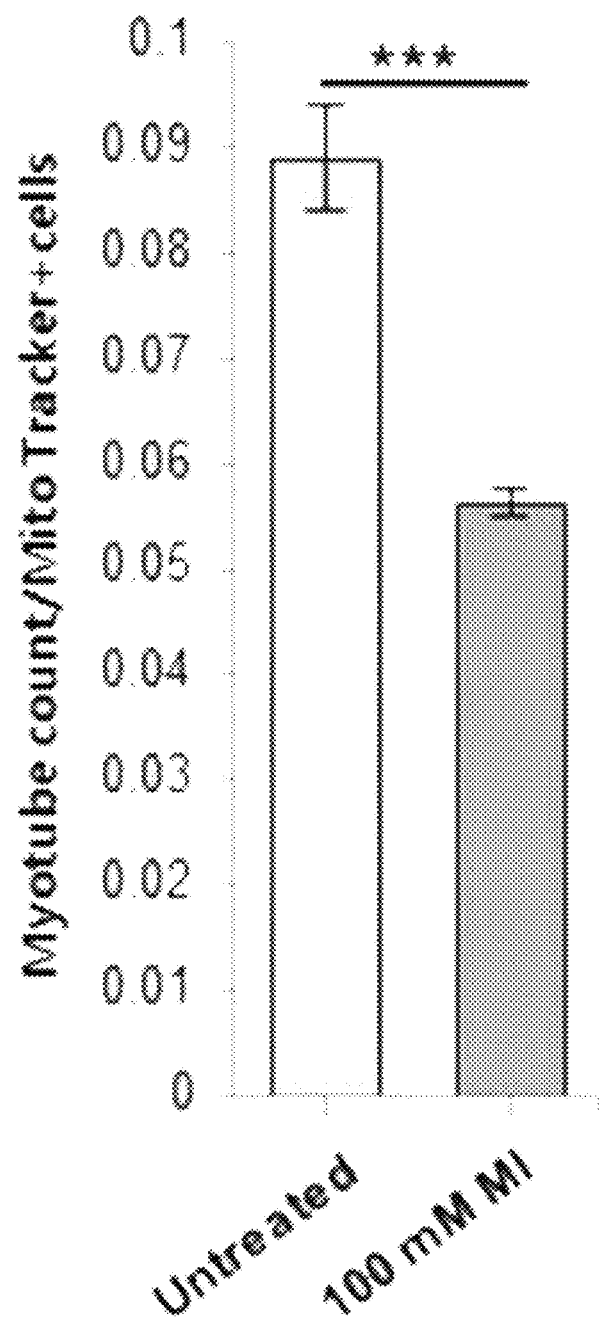
FIG. 2C shows a relative fusion index in myo-inositol-treated cultures (***=p<0.001).
Figure 2D:
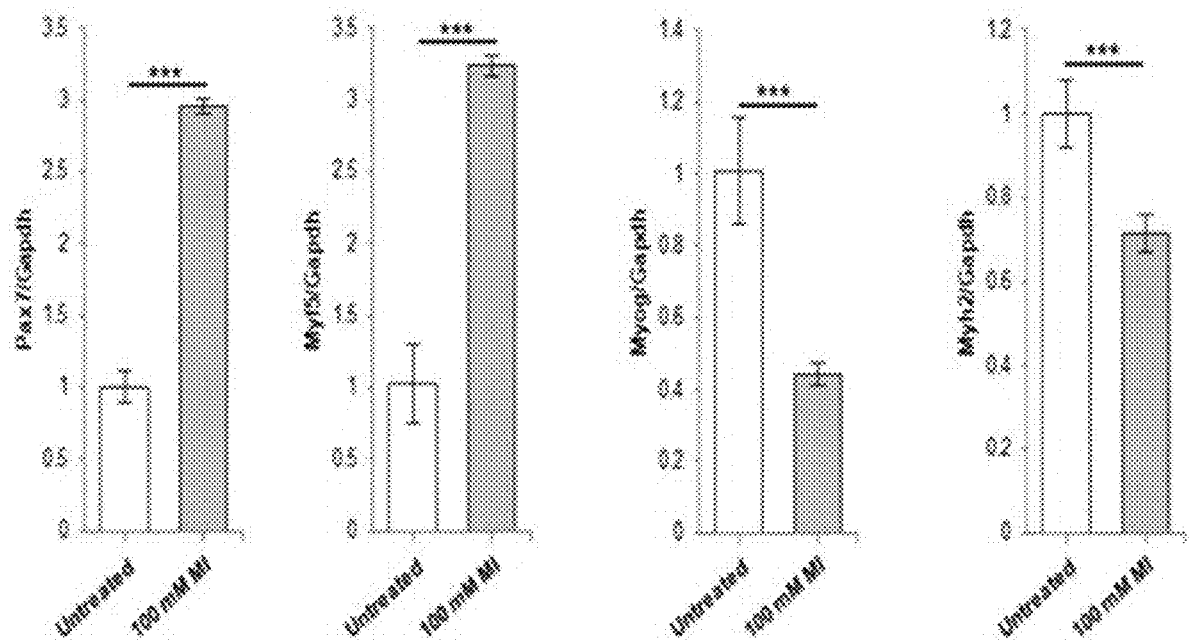
FIG. 2D shows the result of qPCR analysis of Pax7, Myf5, MyoG, and Myh2 in C2C12 cultures incubated for 25 hours in DM or 100 mM myo-inositol-added DM (***=p<0.001)
Figure 2E:
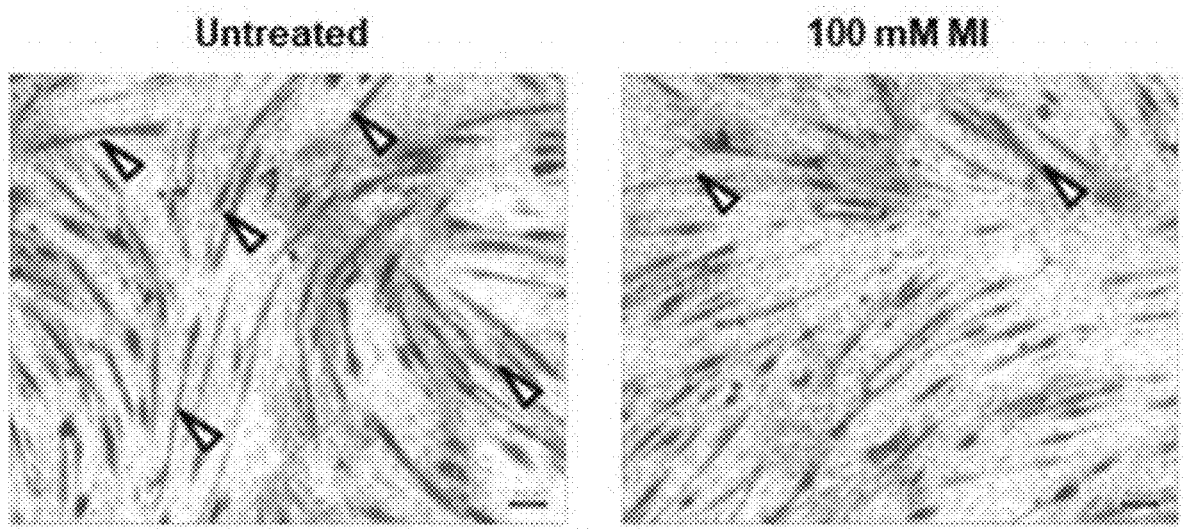
FIG. 2E is a micrograph of H&E-stained C2C12 cultures after 96 hours of incubation with DM and 24 hours of treatment with 100 nM myo-inositol, in which dark-stained myotubes are indicated using white arrows (scale bar=100 μm)
Figure 2F:
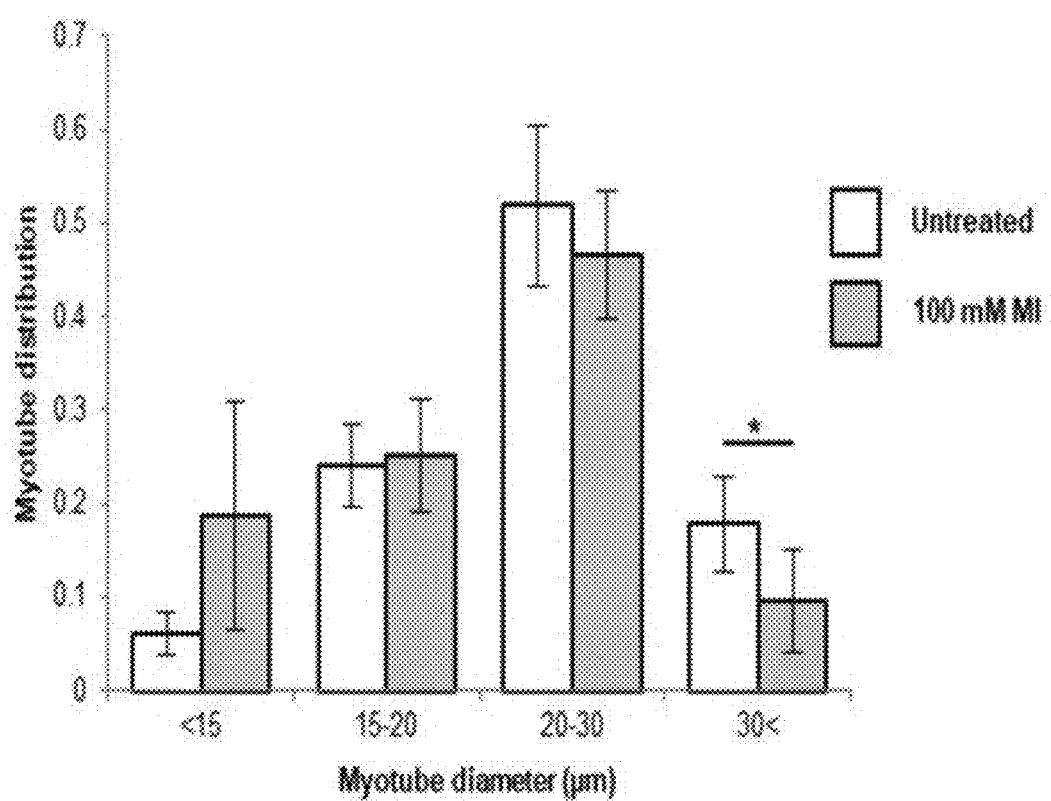
FIG. 2F shows the distribution of myotube diameters in MI-treated cultures (*=p<0.05)
Figure 2G:
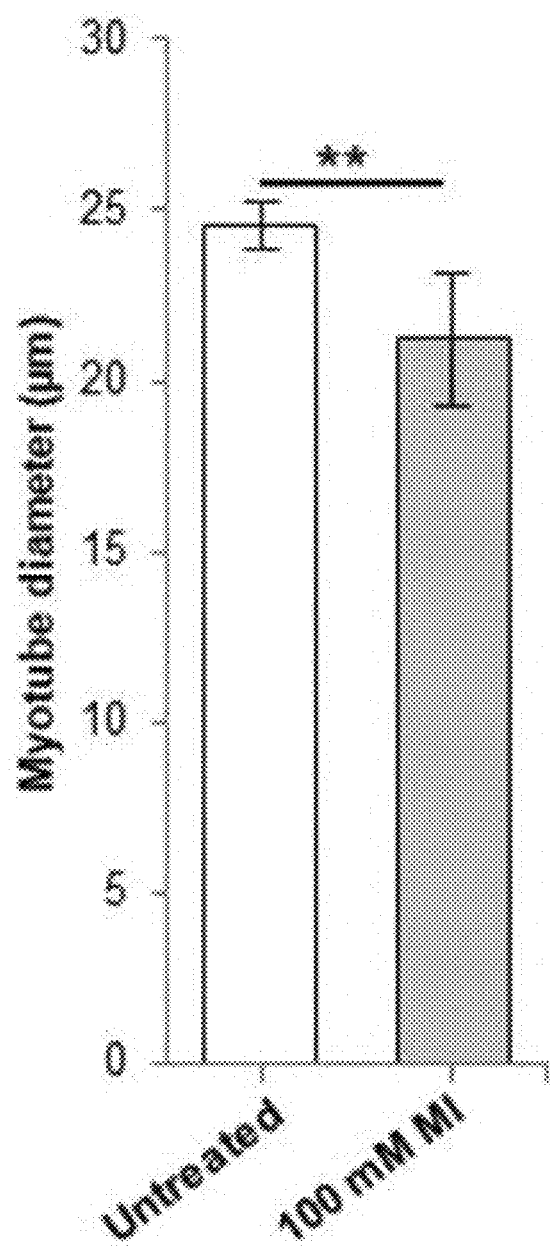
FIG. 2G shows the average myotube diameter in the cultures treated with and myo-inositol (*=p<0.01)
Figure 2H:
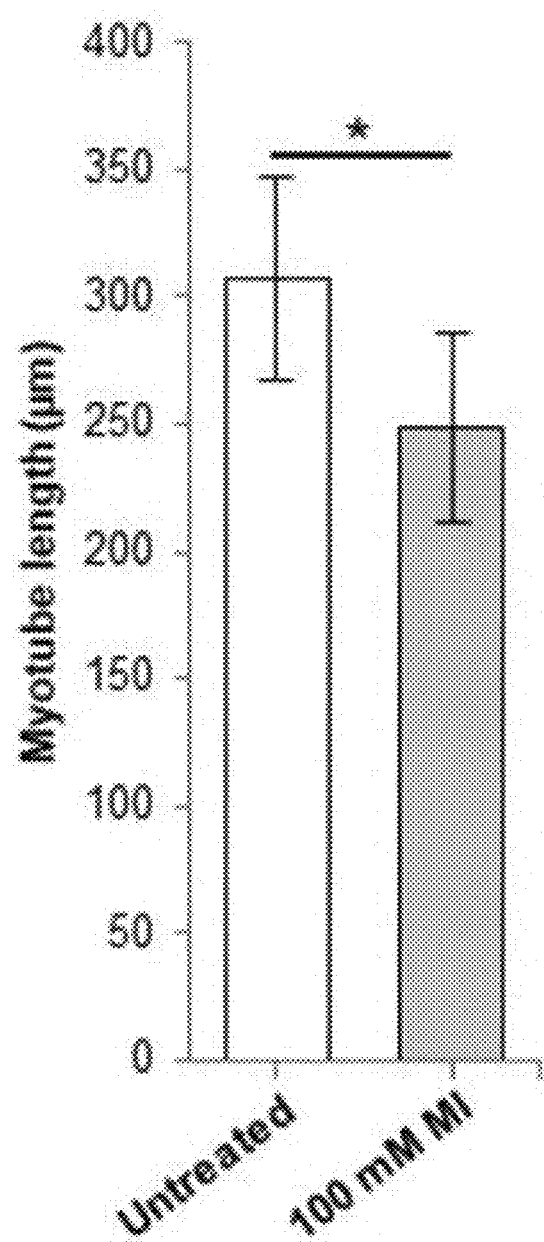
FIG. 2H shows the average myotube length of in the cultures treated with myo-inositol (*=p<0.05)

The effect of myo-inositol on myotube morphology was investigated with H&E-stained C2C12 differentiated cultures (see FIG. 2E). Microscopic analysis showed that treatment with 100 mM myo-inositol for 48 hours induced shortened and narrower myotubes but had no explicit effect on undifferentiated myoblasts. The myo-inositol treatment resulted in reduction in the proportion of larger myotubes which are over 30 μm in diameter (see FIG. 2F). In addition, the average myotube diameter and the average myotube length were decreased by the treatment with 100 mM myo-inositol (see FIGS. 2G and 2H).

Example 4: Confirmation of Effect of IMPase-1 Gene Knockdown on Myotube Atrophy Measurement of IMPase activity in myotubes undergoing atrophy showed that the activity was significantly increased after dexamethasone treatment (see FIG. 3A).

The role of IMPase in muscle atrophy was investigated through gene knockdown of IMPase-1. Western blot and qPCR assay showed that IMPase-1 siRNA treatment reduced IMPase-1 expression in C2C12 myoblasts (see FIGS. 3B and 3C). In addition, IMPase-1 siRNA prevented dexamethasone from reducing the average diameter of myotubes and increased the proportion of larger diameter myotubes (see FIGS. 3D and 3F).

Figure 3A:
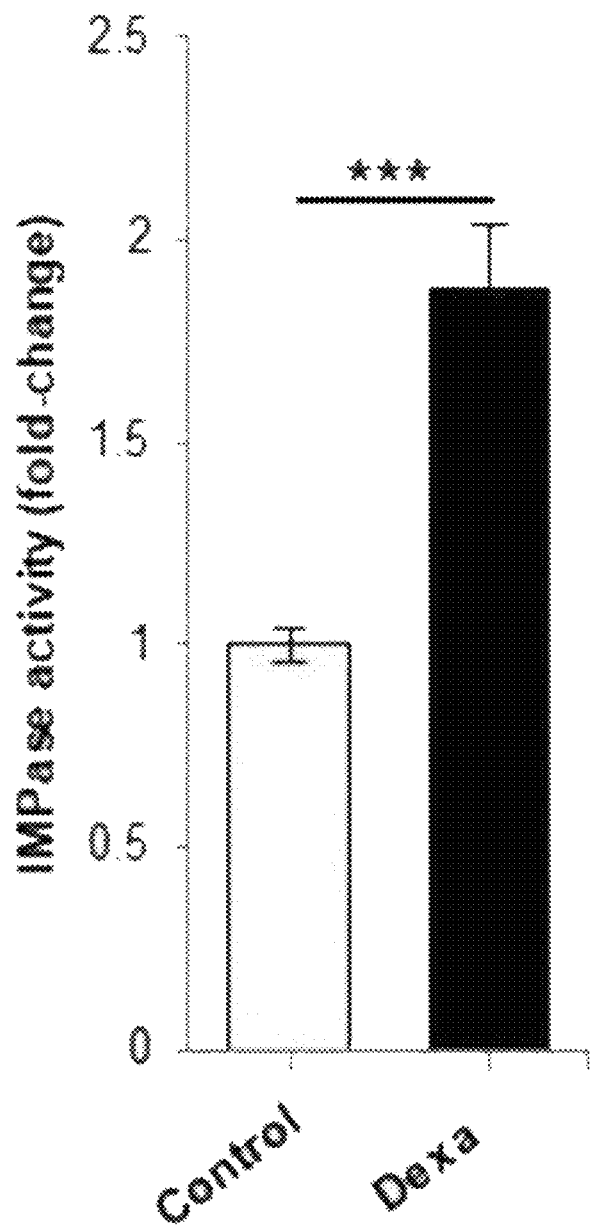
FIG. 3A shows inositol monophosphatase (hereinafter, abbreviated as IMPase) activity in C2C12 myoblasts (control) that are cultured in DM for 72 hours (control) or in C2C12 myoblasts (vehicle) that are incubated in DM for 72 hours and then treated with 10 μM dexamethasone for 24 hours (***=p<0.001)
Figure 3B:
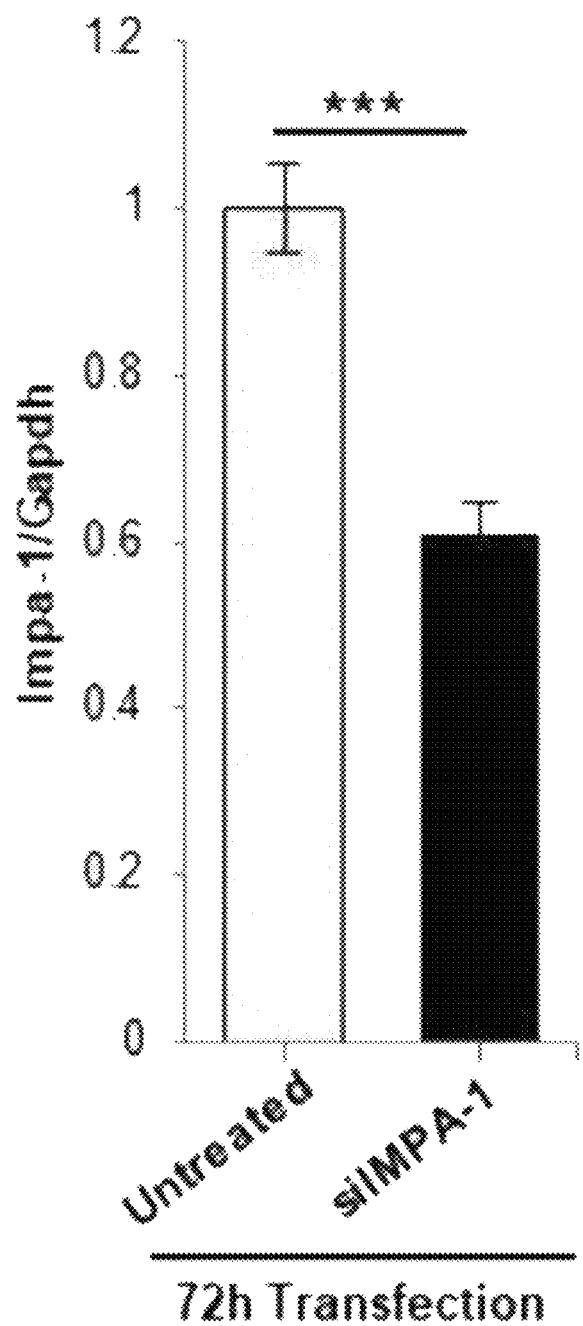
FIGS. 3B and 3C show that the gene knockdown of Impa-1 caused by siRNA is confirmed through a qPCR analysis and a Western blot test (***=p<0.001)
Figure 3C:
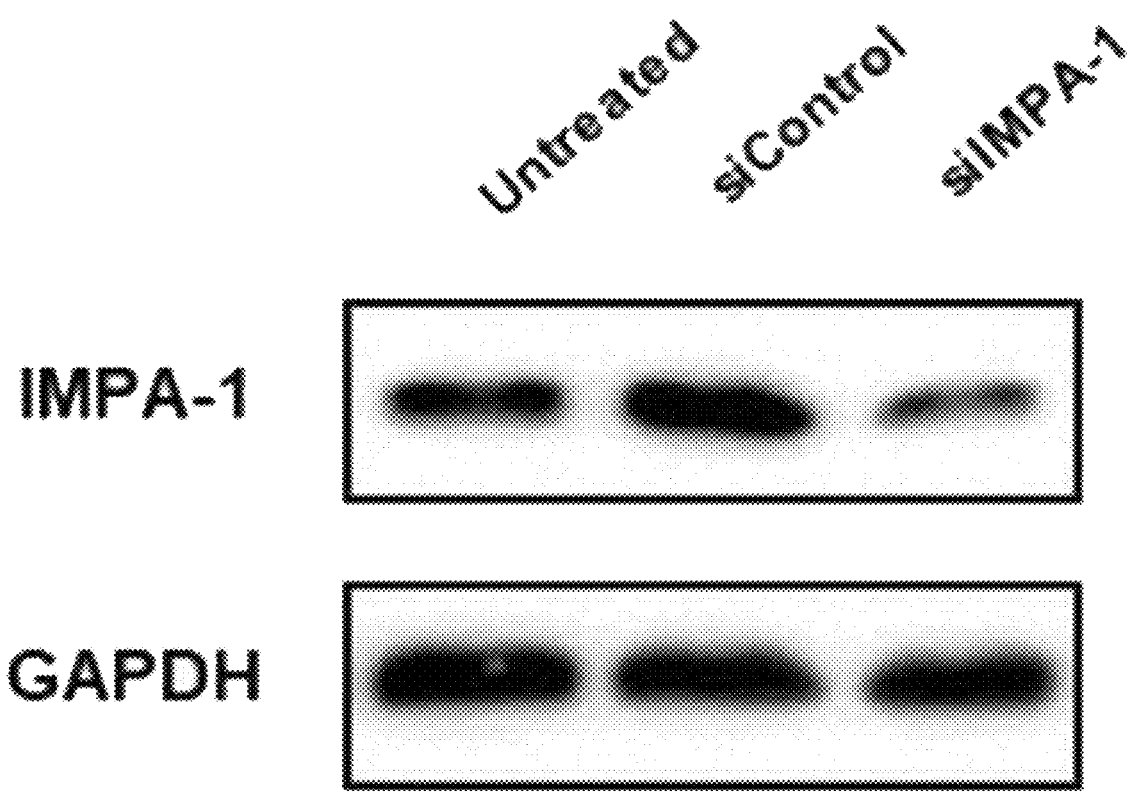
Figure 3D:
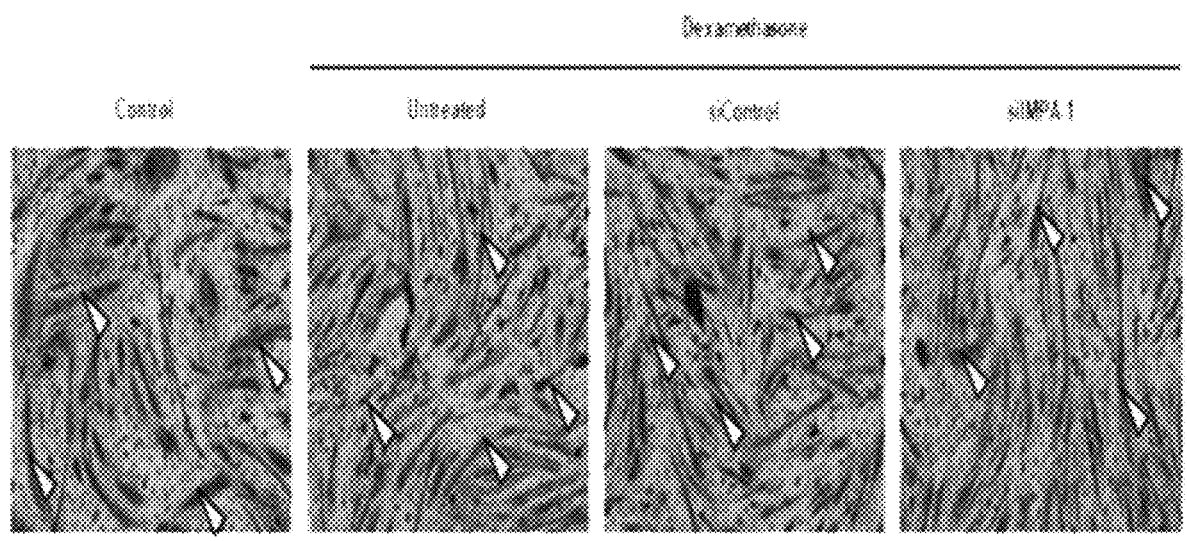
FIG. 3D shows micrographs of H&E-stained C2C12 myoblast cultures after treatment in different conditions (scale bar=100 μm)
Figure 3E:
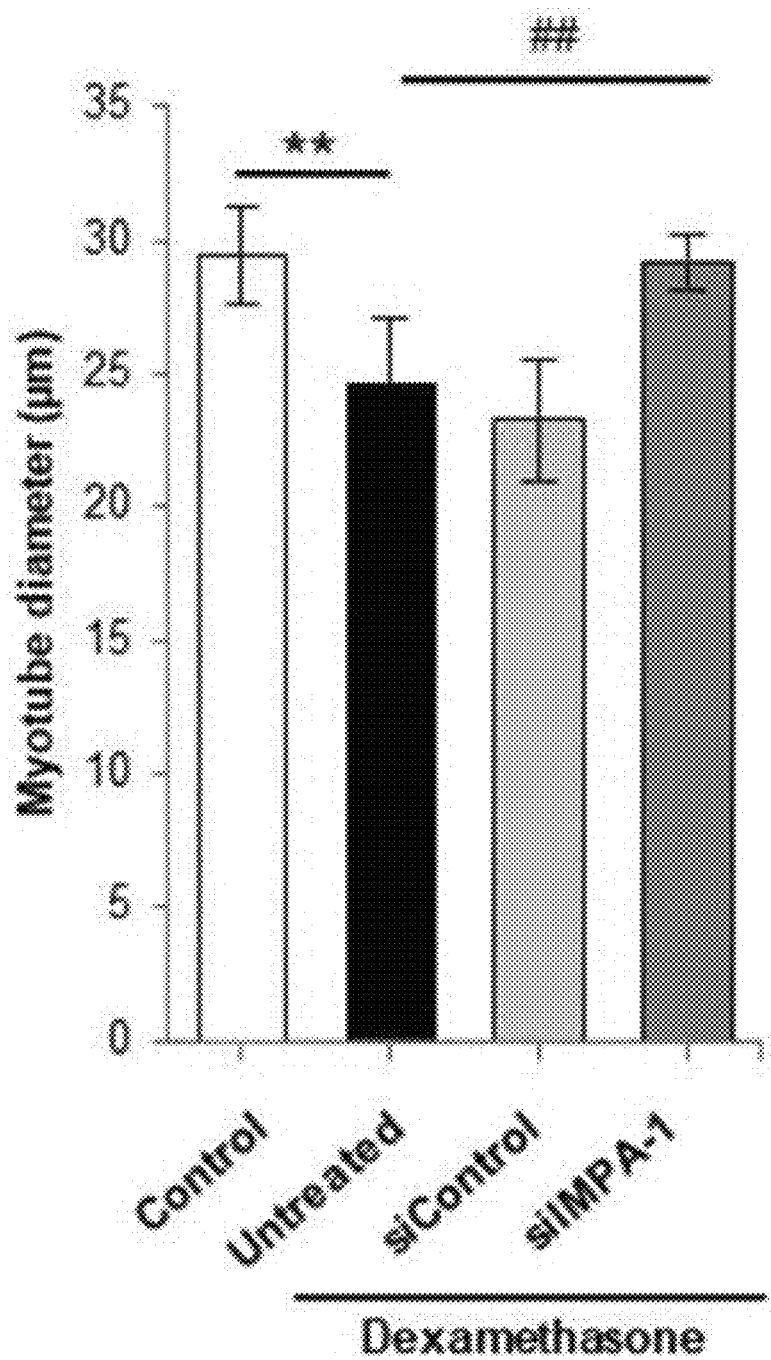
FIG. 3E shows the result of comparison in average myotube diameter before and after siRNA treatment (**=p<0.01)
Figure 3F:
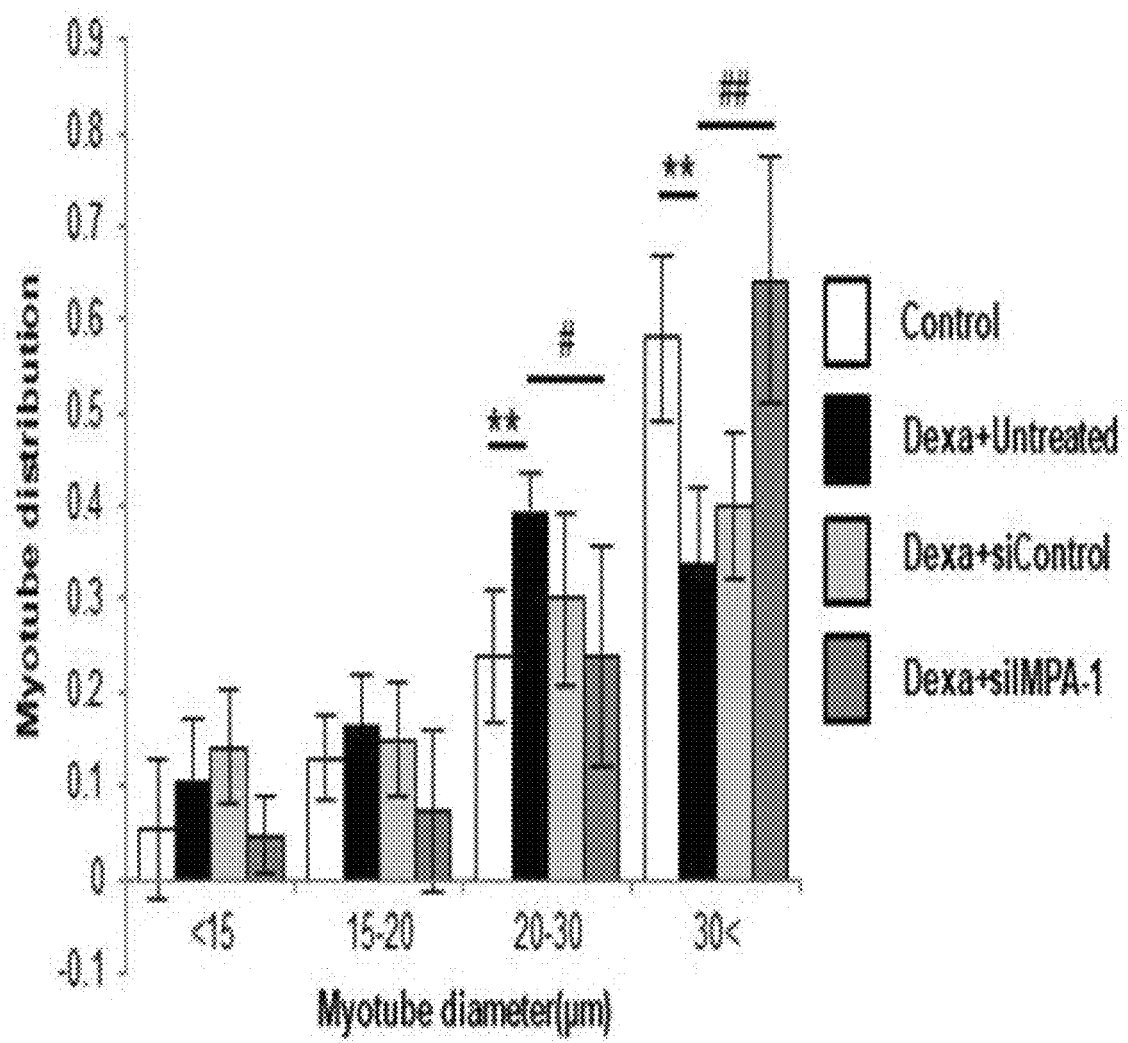
FIG. 3F shows a distribution of myotube diameters resulting from siRNA treatment (##=p<0.01, =p<0.01, *=p<0.001)
Figure 3G:
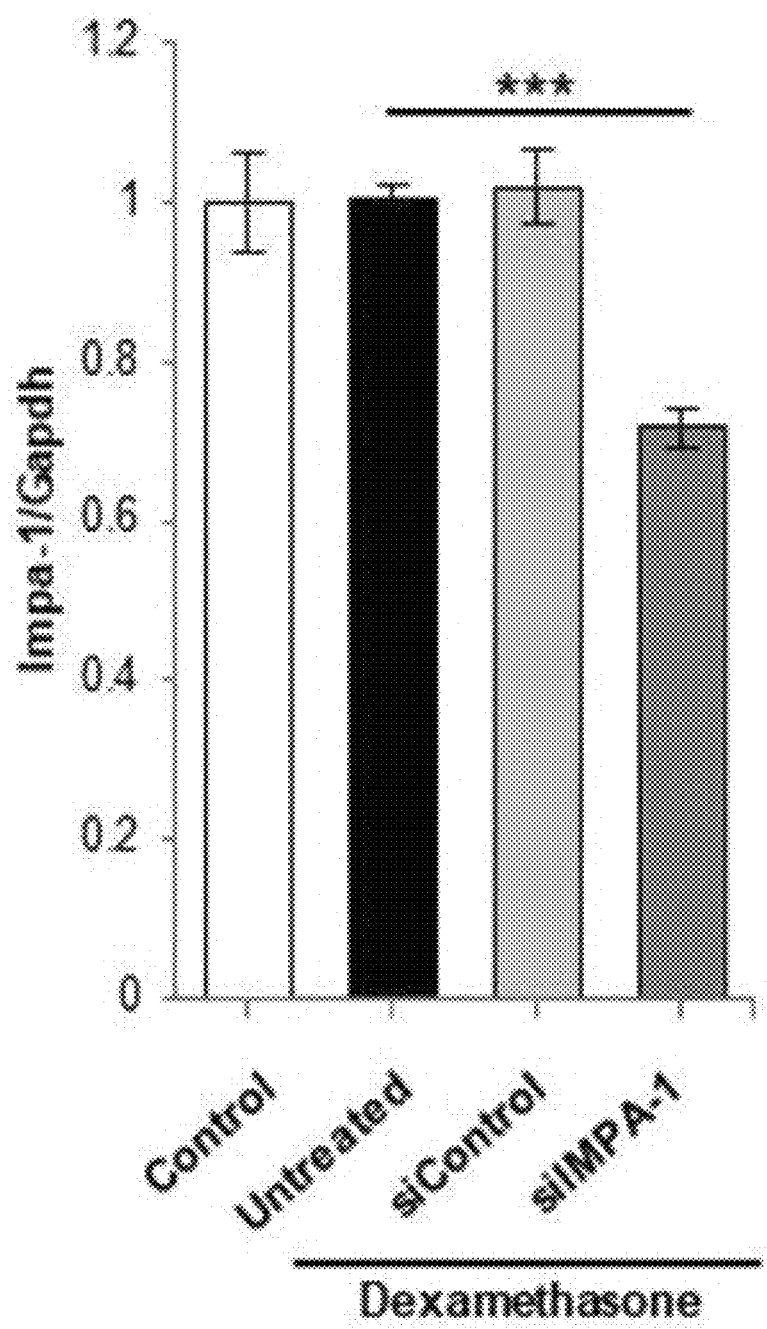
FIG. 3G shows the result of qPCR analysis of Impa-1 in siRNA-treated myotubes (***=p<0.001)

The gene knockdown of IMPase-1, which is attributable to siRNA treatment, was confirmed through the qPCR assay (see FIG. 3G).

Example 5: Confirmation of Effect of IMPase Inhibitor on Myogenesis and Myotube To determine the effect of IMPase-targeting compounds on myogenesis, ebselen, L-690,330 and LiCl were used. First, the viability of myoblasts and myotubes was evaluated to determine appropriate treatment concentrations.

Figure 4A:
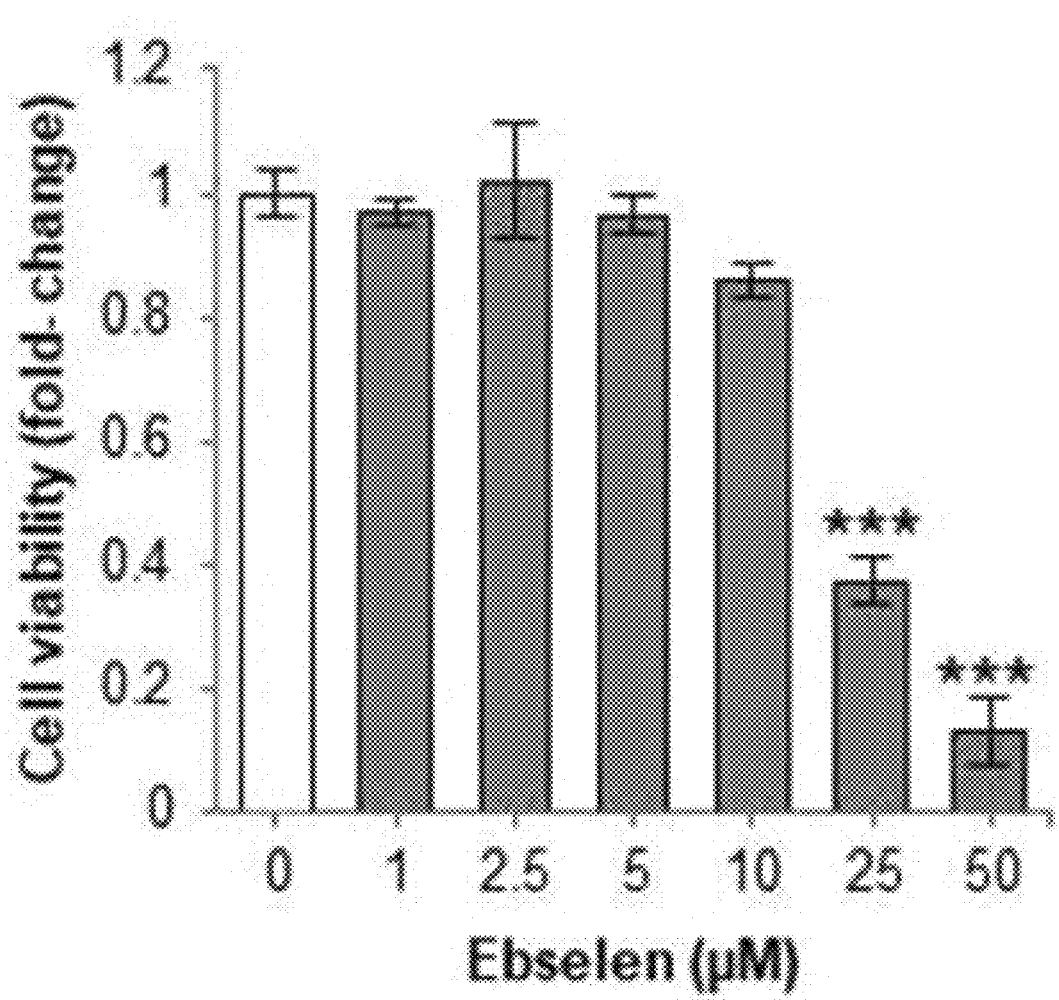
FIGS. 4A to 4F show the results of an MTT assessment with increasing concentrations of ebselen, LiCl, and L-690,330 ($IC_{50}$=22.42 μM when myoblasts are treated with ebselen, and $IC_{50}$=19.93 mM when myoblasts are treated with LiCl) (=p<0.01 and *=p<0.001)
Figure 4B:
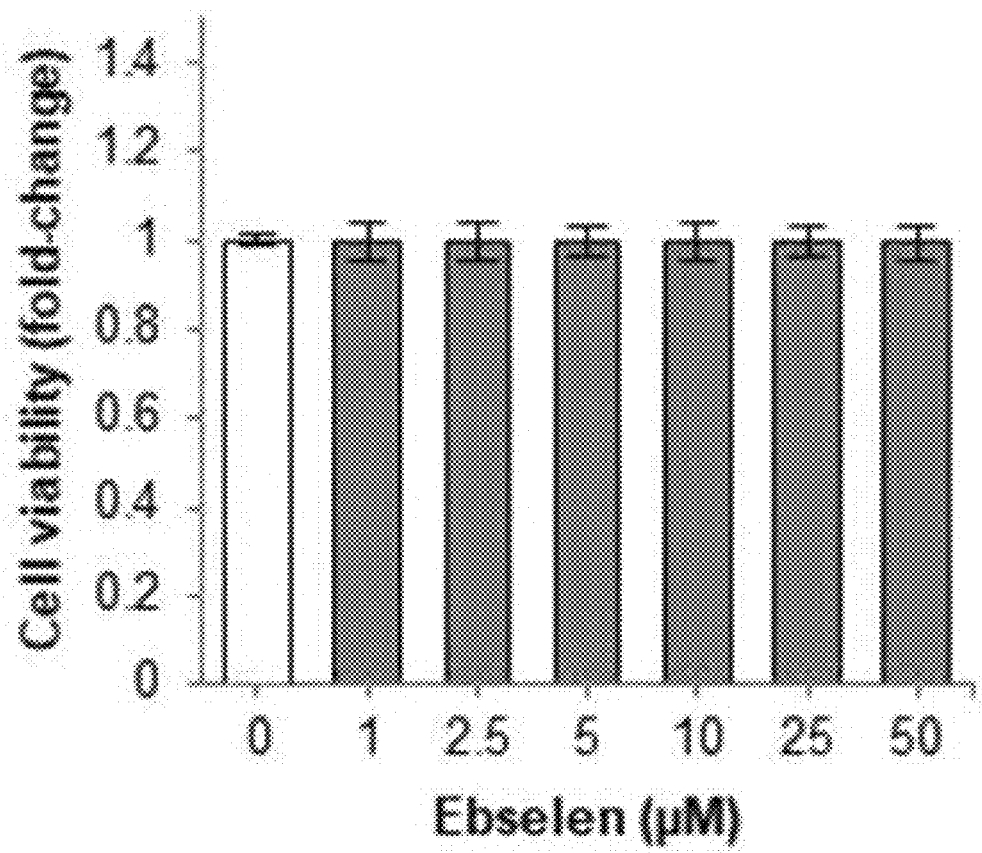
Figure 4C:
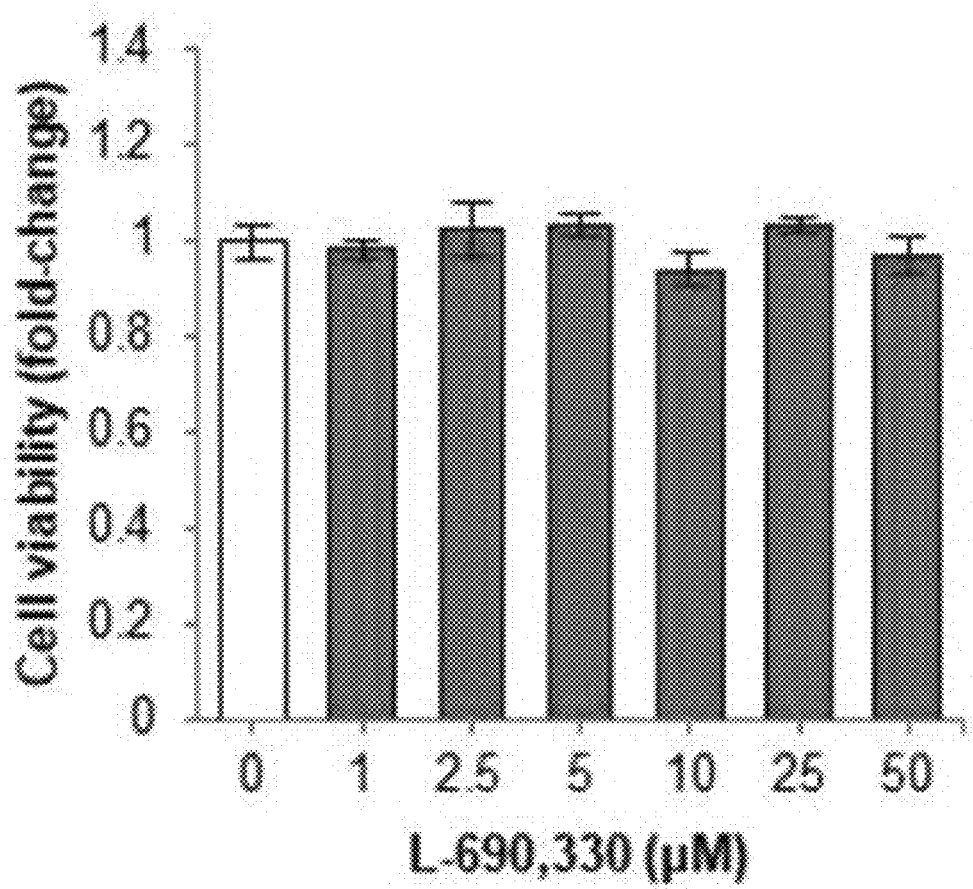
Figure 4D:
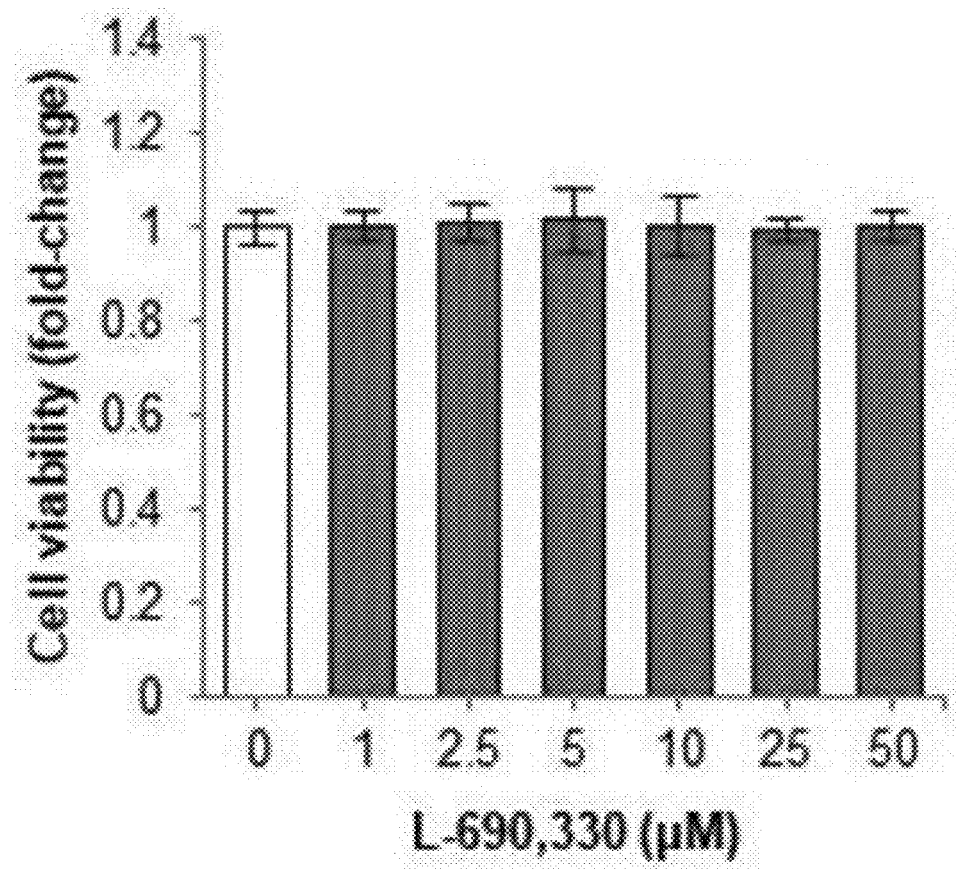
Figure 4E:
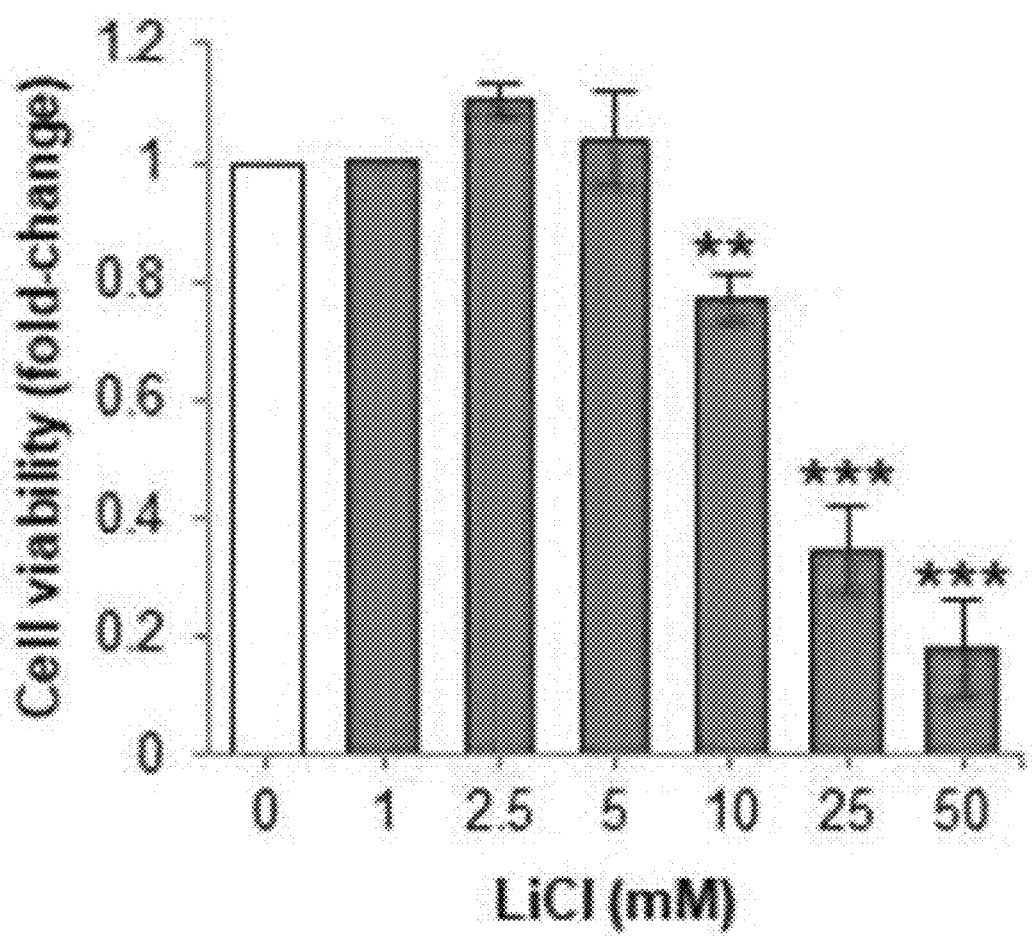
Figure 4F:
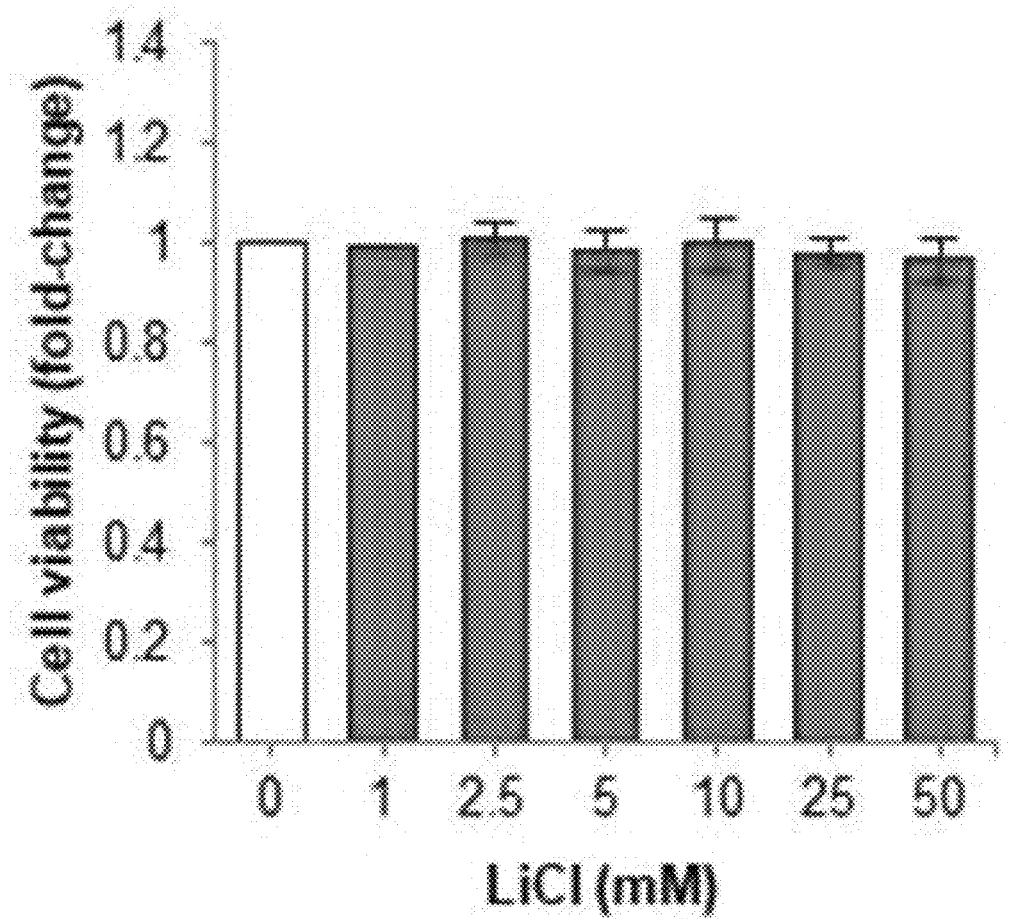
Figure 4G:
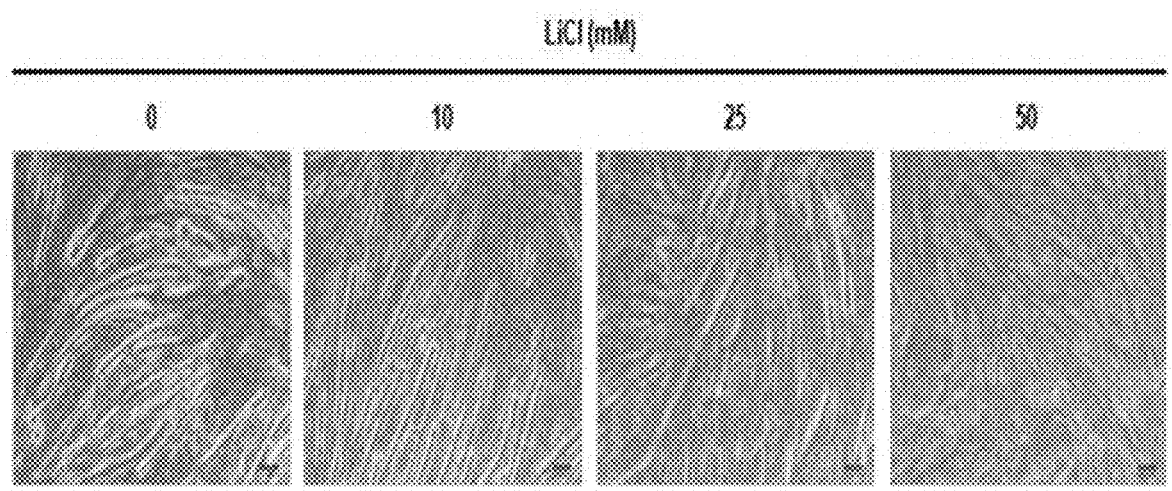
FIG. 4G shows phase contrast micrographs of C2C12 myotubes treated with 10, 25, or 50 mM LiCl for 72 hours (scale bar=100 μm)

When treated with ebselen, cytotoxicity was not observed in myoblasts under a condition in which the concentration of ebselen was 10 μM or lower, cytotoxicity was not observed in myotubes under a condition in which the concentration of ebselen was 50 µM or lower (see FIGS. 4A and 4B). When treated with L-690,330, cytotoxicity was not observed in myoblasts and myotubes at concentrations of up to 50 µM (see FIGS. 4C and 4D). When treated with LiCl, cytotoxicity was not observed in myoblasts at concentration of up to 5 mM (see FIG. 4E). In addition, MTT assay showed that LiCl at concentrations of 50 mM or lower had no cytotoxicity in myotube cultures (see FIG. 4F). However, a microscopic observation showed that the number of observable myotubes was reduced after treatment with 50 mM LiCl (see FIGS. 4F and 4G). Therefore, 10 µM ebselen, 50 µM L-690,330, and 5 mM LiCl were selected as treatment concentrations for C2C12 cells.

Figure 4H:
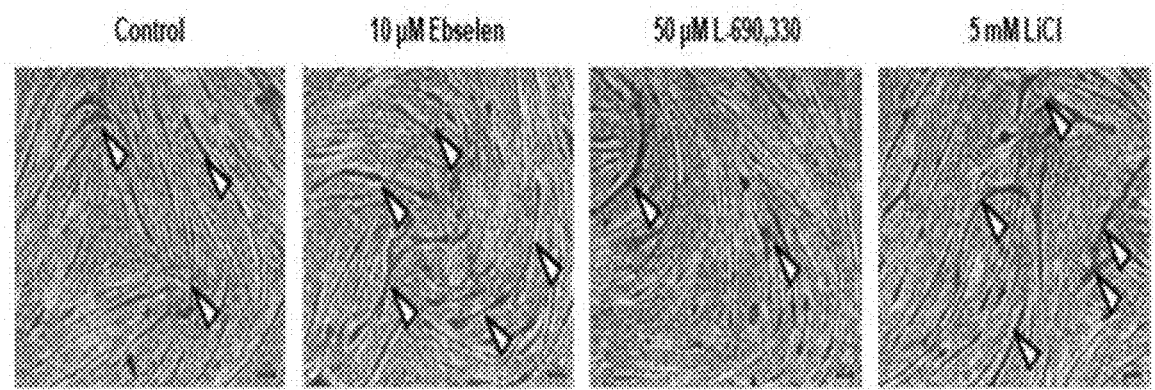
FIG. 4H shows micrographs of H&E-stained C2C12 myoblast cultures treated with 10 μM ebselen, 5 mM LiCl, or 50 μM L-690,330 for 24 hours after incubation with DM for 96 hours.
Figure 4I:
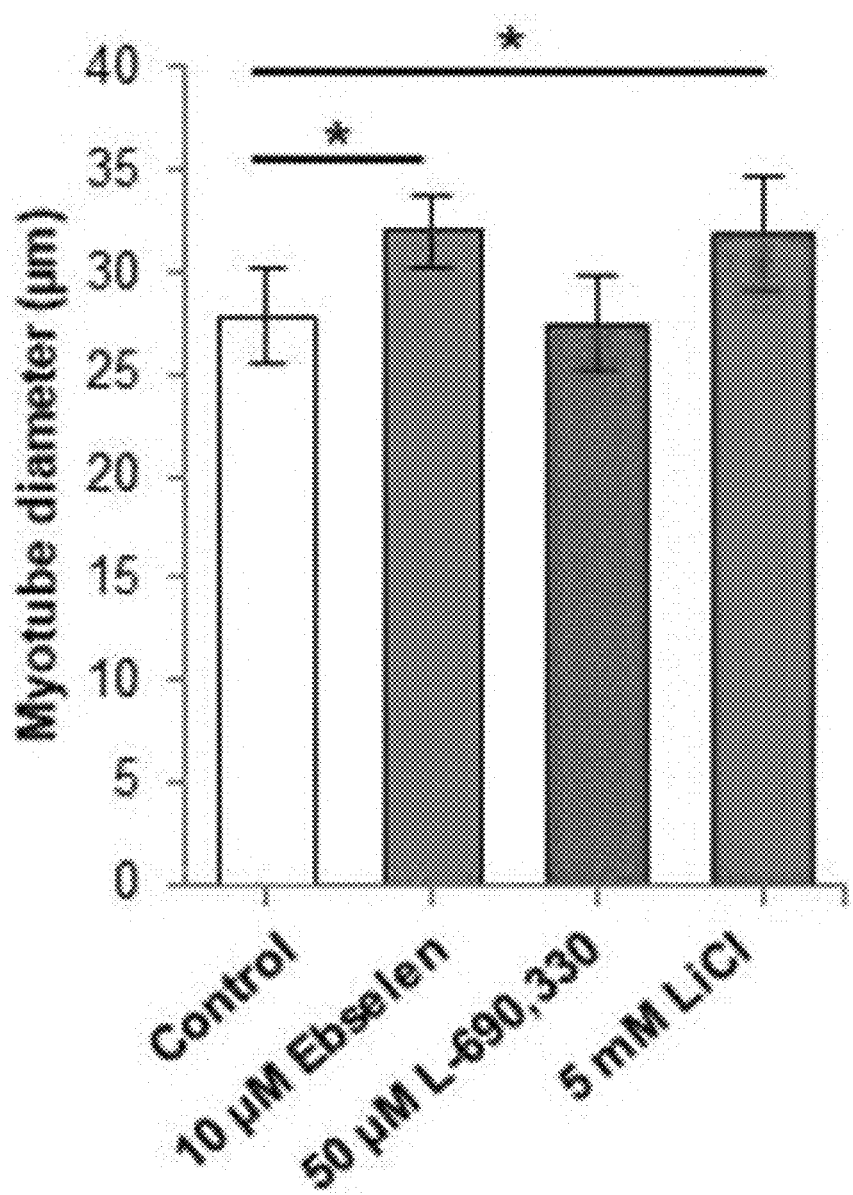
FIG. 4I is a graph showing the average myotube diameters in the cultures treated with ebselen, L-690,330, and LiCl and, L-690 330 (*=p<0.05)
Figure 4J:
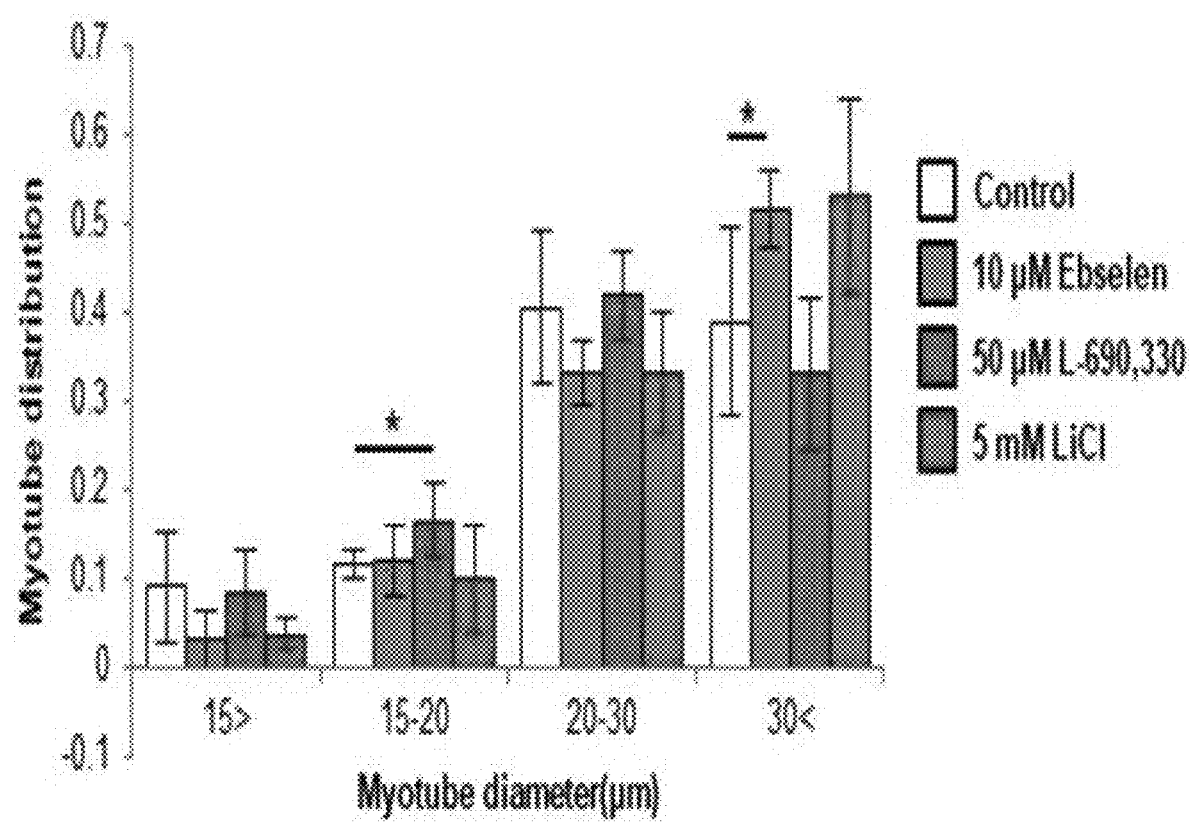
FIG. 4J is a graph showing a distribution of myotube diameters in MI-treated cultures (*=p<0.05)
Figure 4K:
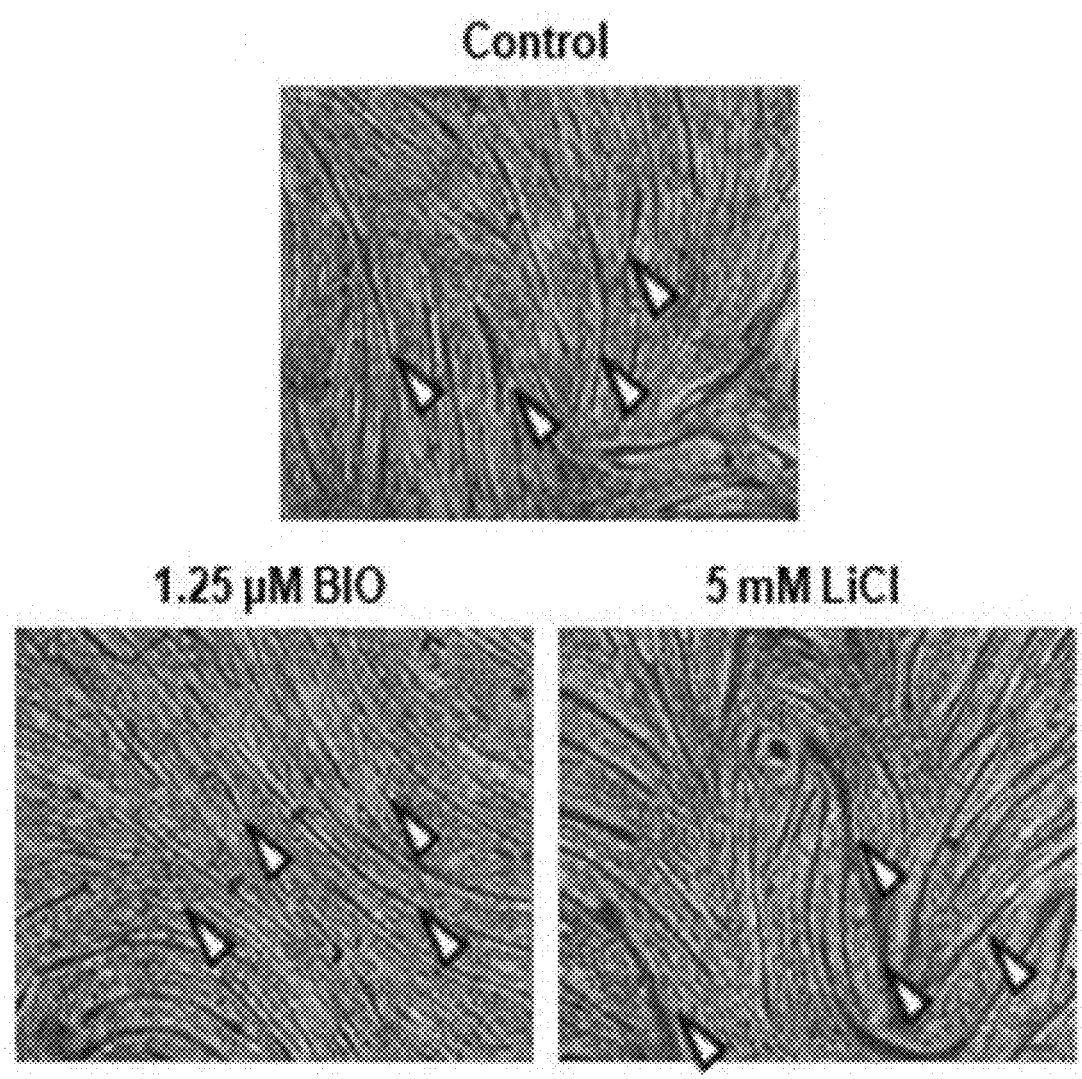
FIG. 4K shows micrographs of H&E-stained C2C12 myoblast cultures treated with 1.25 μM BIO (GSK-3b inhibitor) or 5 mM LiCl for 24 hours after 72 hours of incubation with DM.
Figure 4L:
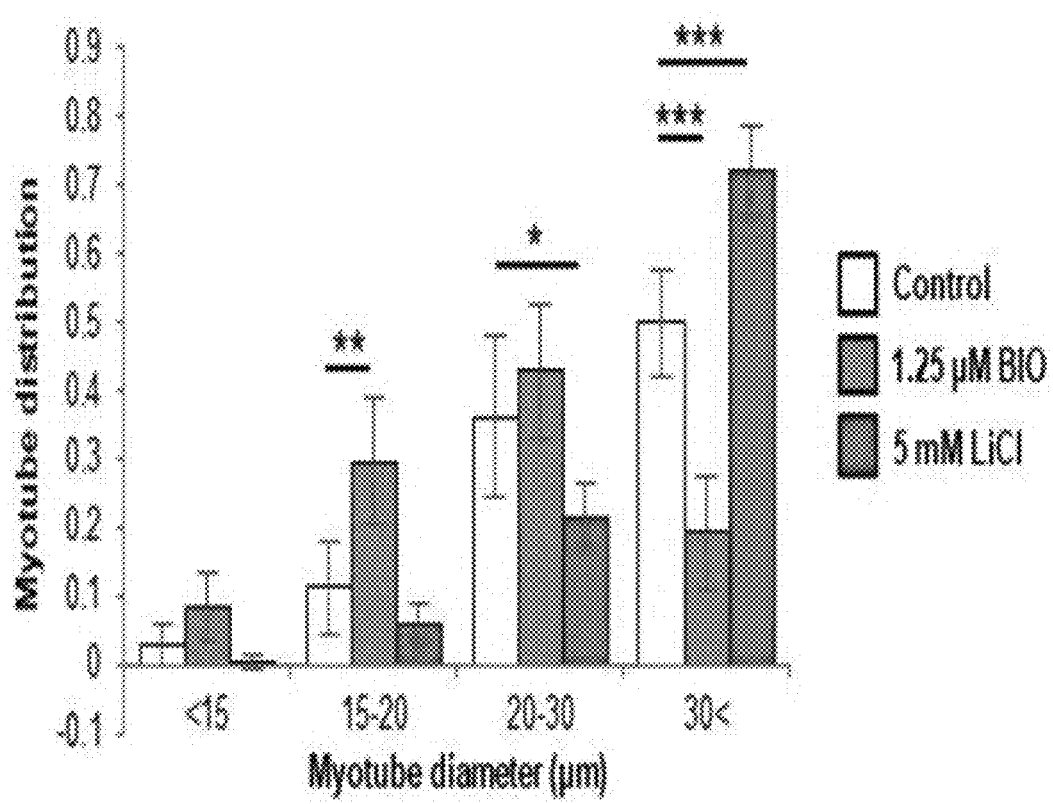
FIG. 4L is a graph showing a distribution of myotube diameters in the BIO- or LiCl-treated cultures (*=p<0.01, =p<0.01, and *=p<0.001)
Figure 4M:
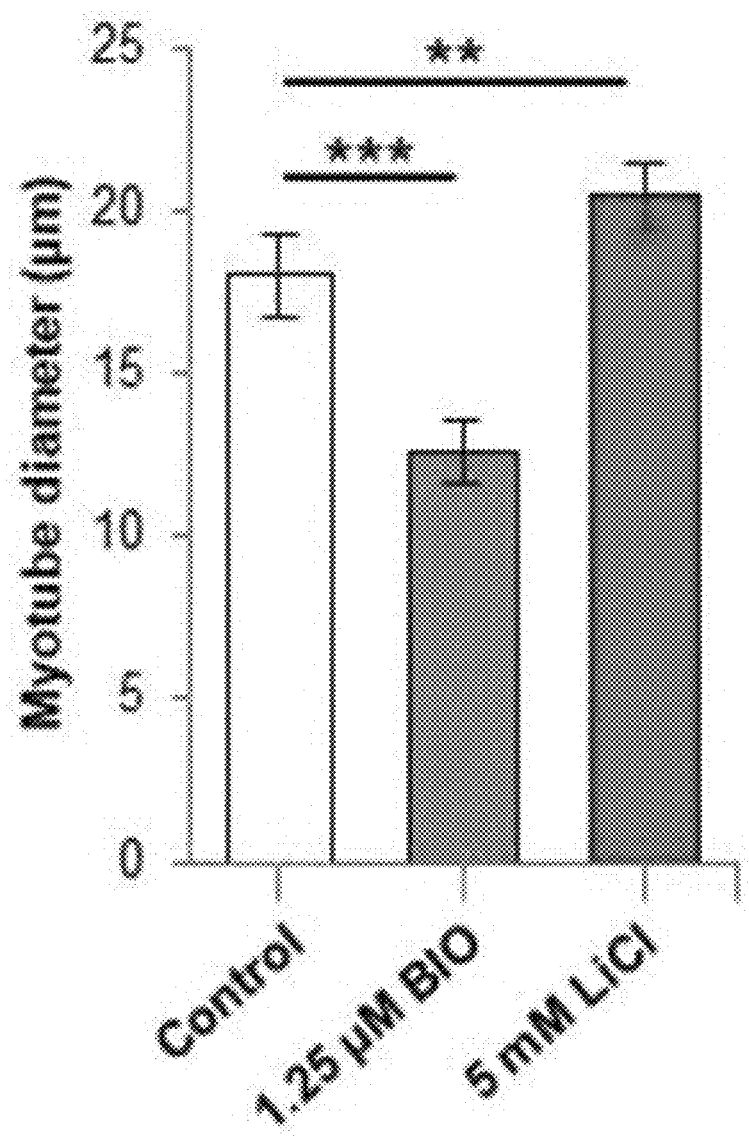
FIG. 4M is a graph showing the average myotube diameter in the BIO- or LiCl-treated cultures (=p<0.01 and *=p<0.001)
Figure 5A:
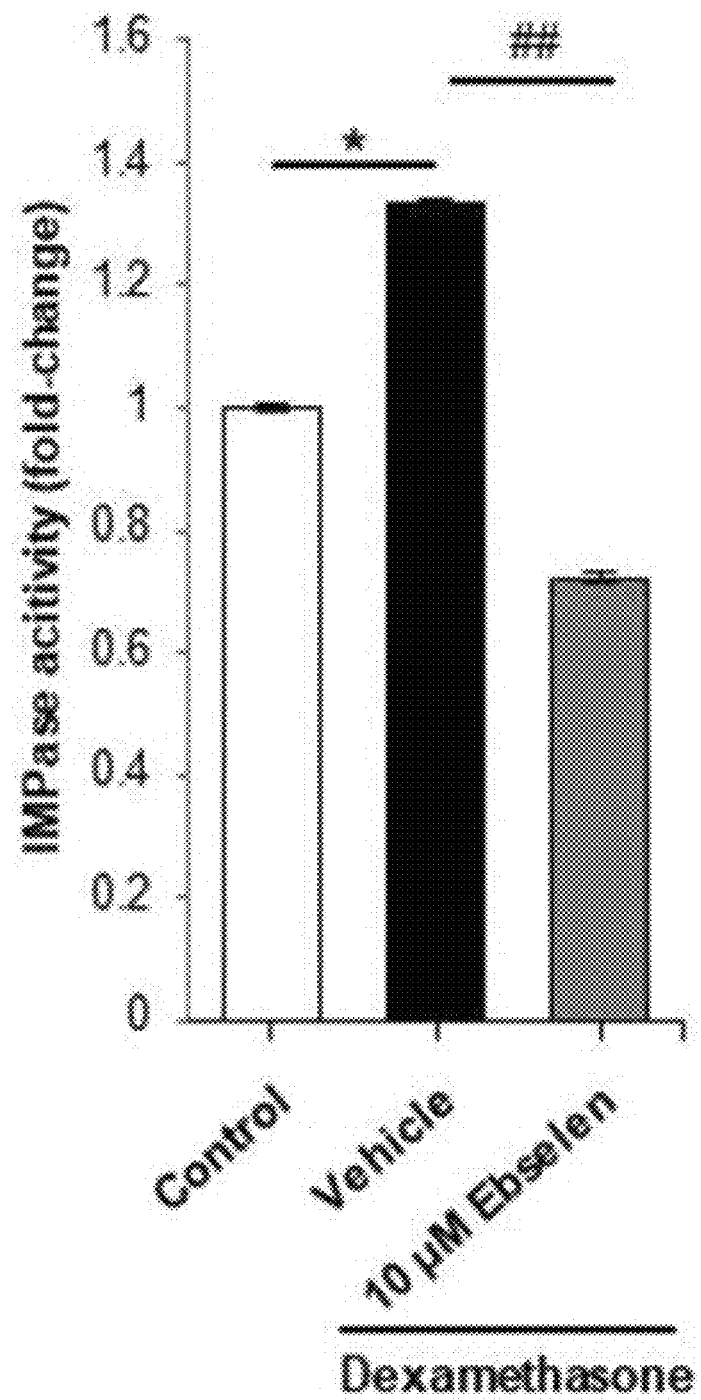
FIG. 5A is a graph showing a result of comparison in IMPase activity in C2C12 myoblasts treated with each of dexamethasone and ebselen under different conditions (*=p<0.05, ##=p<0.01)
Figure 5B:
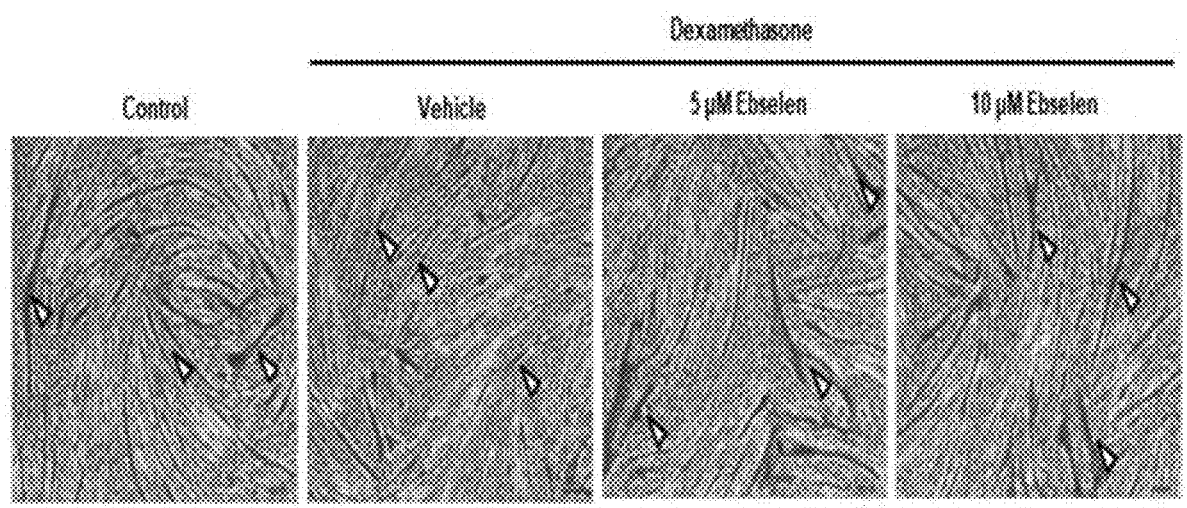
FIG. 5B is the result of observation of H&E-stained C2C12 myotubes treated with each of dexamethasone and ebselen under different conditions.
Figure 5C:
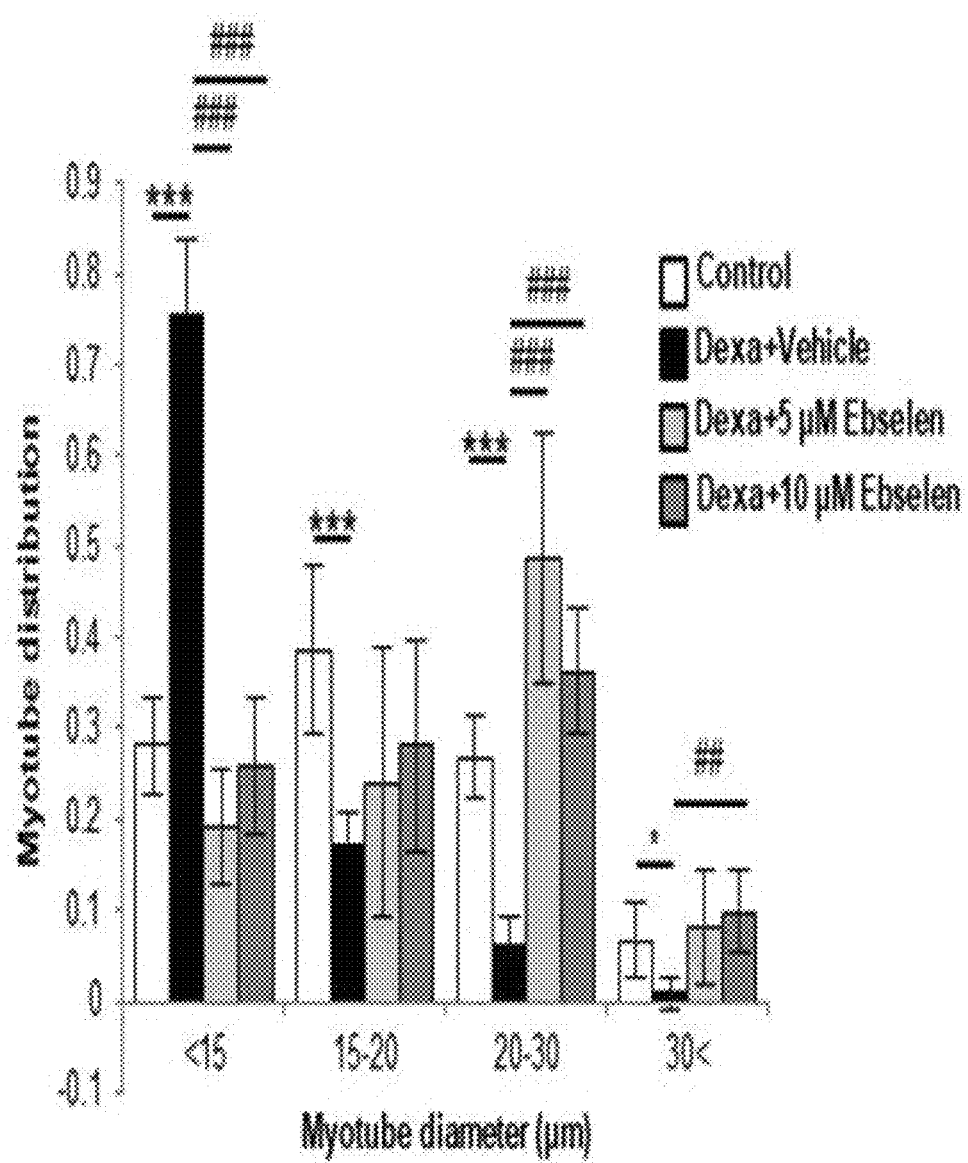
FIGS. 5C and 5D are graphs showing the diameter distributions and average diameters of myotubes treated with each of dexamethasone and ebselen under different conditions (*=p<0.05, ***=p<0.001, ##=p<0.01, ###=p<0.001)
Figure 5D:
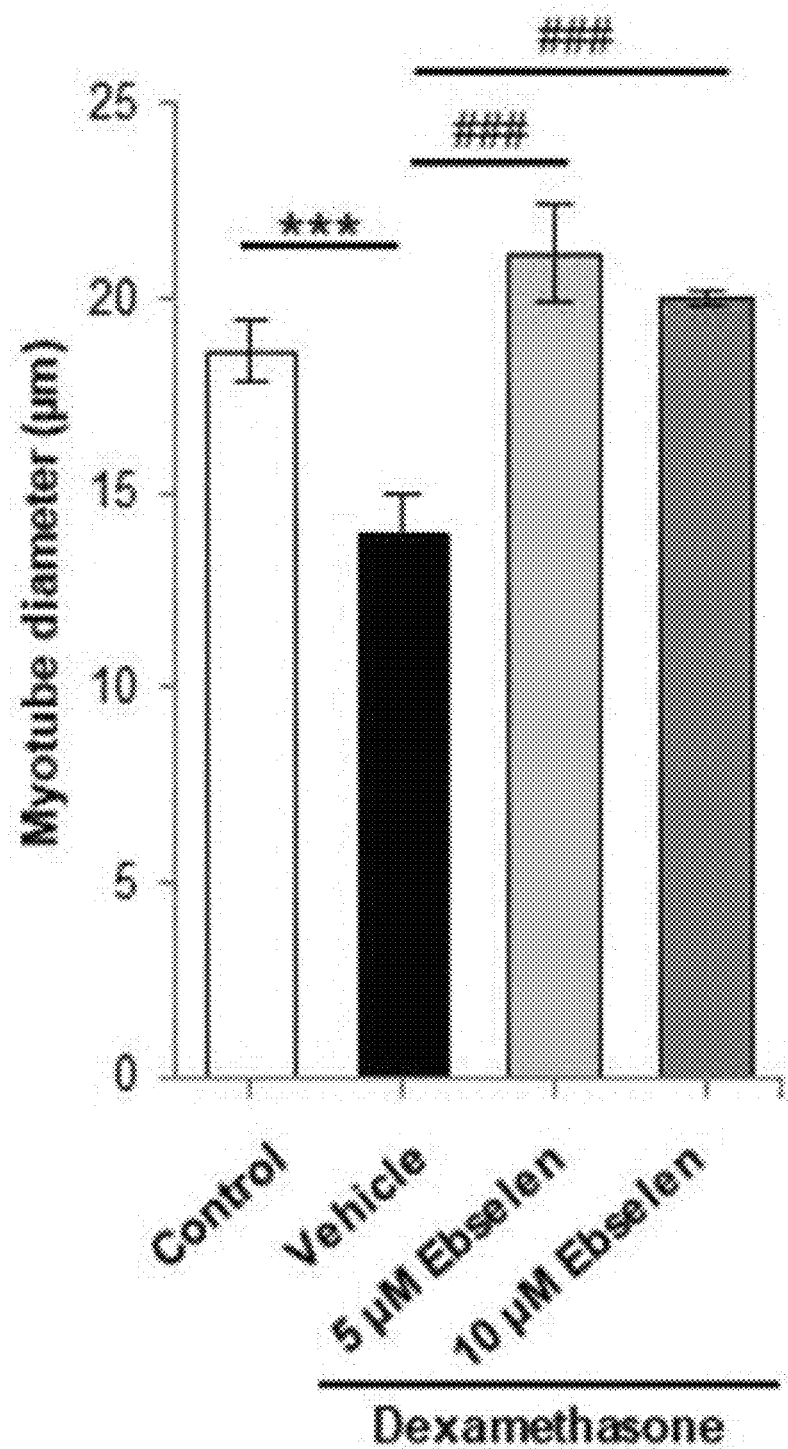
Figure 5E:
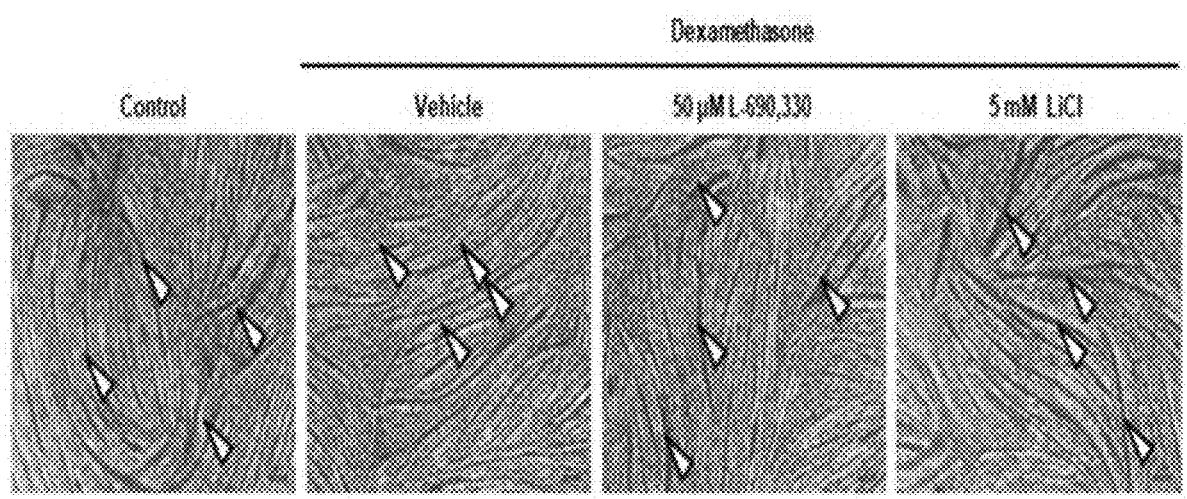
FIG. 5E shows micrographs of H&E-stained C2C12 myotube cultures co-treated with dexamethasone and L-690, 330 or co-treated with dexamethasone and LiCl.
Figure 5F:
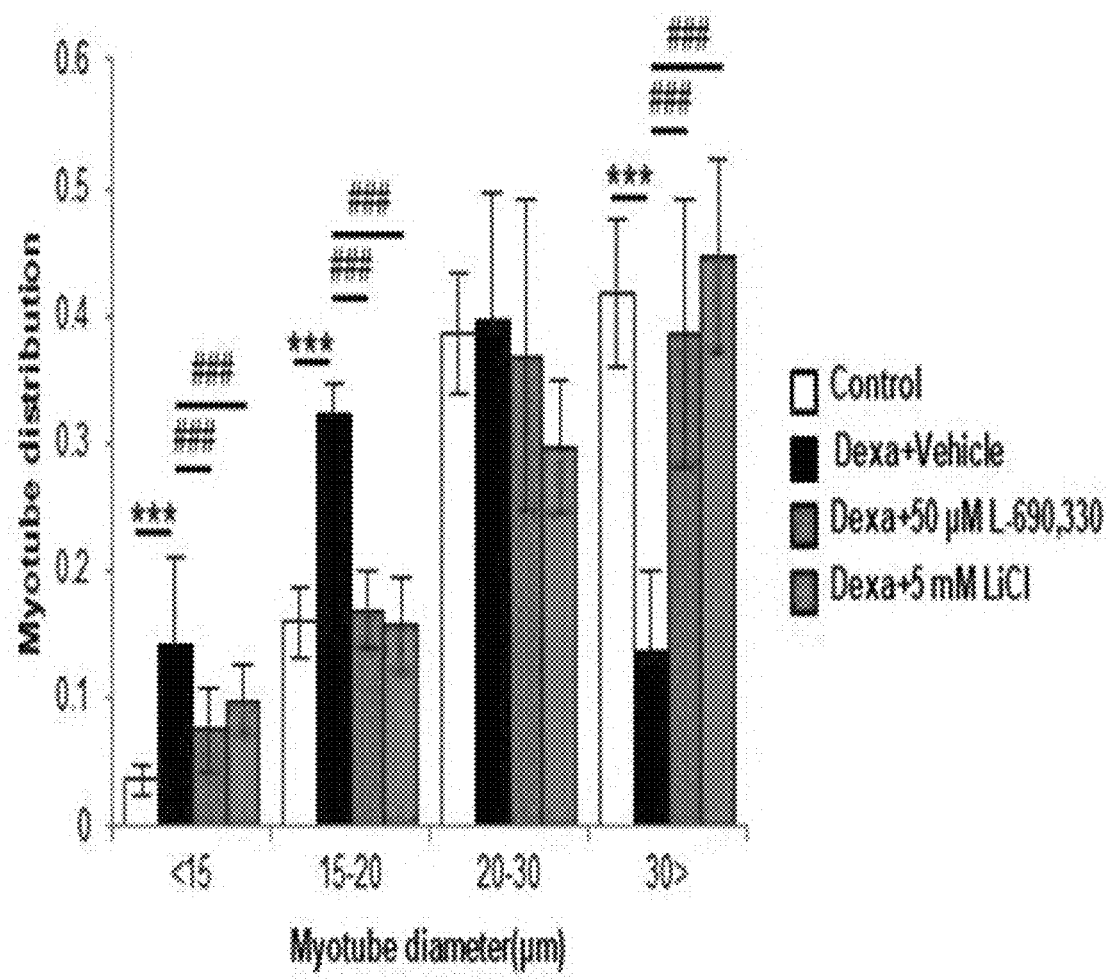
FIGS. 5F and 5G illustrate the results of comparison in both the myotube diameter distribution and the average diameter between the case of co-treatment with dexamethasone and L-690,330 and the case of co-treatment with dexamethasone and LiCl (***=p<0.001, ###=p<0.001)
Figure 5G:
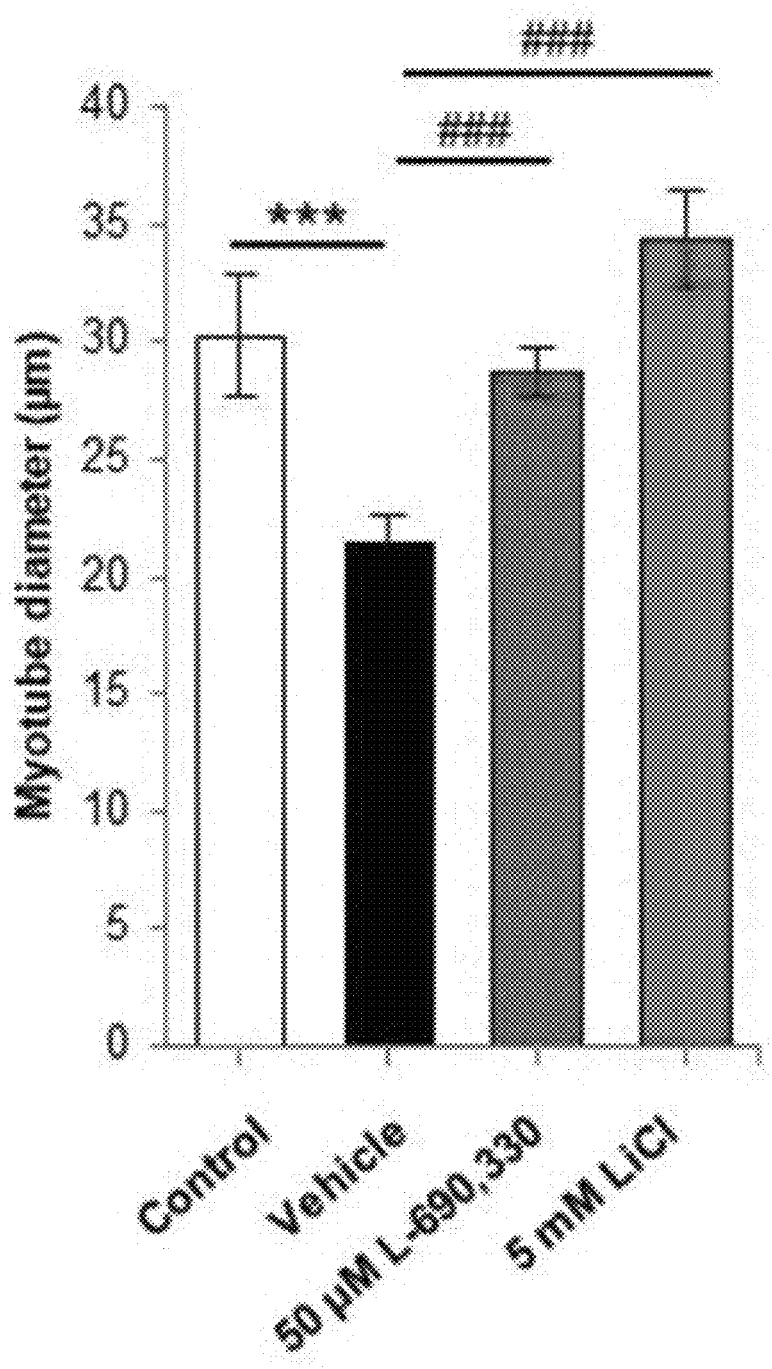

In myoblast differentiation, ebselen and LiCl treatments enhanced myotube formation and increased overall myotube diameters (see FIGS. 4H and 4I). In addition, ebselen treatment significantly increased the proportion of larger diameter myotubes (see FIG. 4J).

Since LiCl is also widely used as a glycogen synthase kinase-3l3 (GSK-3(3) inhibitor, to determine whether the enhancement of myotube formation by LiCl was due to GSK-3l3 inhibition, LiCl was compared with BIO, which is a GSK-3l3 inhibitor. As a result, it was observed that the BIO treatment had the opposite effect to the LiCl treatment and inhibited myotube formation (see FIGS. 4L and 4M).

Ebselen is a drug having a well-known pharmacological profile, being safe for use in humans, and being less toxic than LiCl. Accordingly, IMPase activity analysis was performed, and the result confirmed that ebselen was effective in inhibiting IMPase activity in myotubes treated with dexamethasone (see FIG. Myotubes treated with ebselen and dexamethasone did not show a decrease in average diameter and occurrence of narrower myotubes that were observed in cultures treated with dexamethasone alone (see FIGS. 5B to 5D).

To further confirm that the cause of the compound-induced IMPase inhibition was the anti-atrophic effect, myotubes were treated with dexamethasone alone or were co-treated with LiCl or L-690,330. As a result, the overall average diameter was increased and larger diameter myotubes were observed in cultures treated with LiCl or L-690,330 (see FIGS. 5E to 5G).

Example 6: Confirmation of Effect of Ebselen on Down-regulation of FoxO3a and on Increase of Total Protein Synthesis Considering the up-regulation of FoxO3a by myo-inositol (see FIG. 1E), the effect of ebselen on FoxO3a was investigated (see FIG. 6A). As a result, it was confirmed through PCR analysis that dexamethasone treatment up-regulates the expression of Atrogin-1 and FoxO3a rather than the expression of FoxOla, in C2C12 myotubes (see FIGS. 6A to 6D). In addition, ebselen inhibited the up-regulation of Atrogin-1 and FoxO3a expression caused by dexamethasone, and the effect of ebselen was confirmed using qPCR (see FIGS. 6C to 6D). On the other hand, LiCl and L-690,330 which are IMPase inhibitors also inhibited the up-regulation of FoxO3a expression caused by dexamethasone (see FIG. 6E). In addition, it was also confirmed that NOX inhibitor VII and ebselen oxide, which are organic selenium compound derivatives, inhibited the expression of Atrogin-1 and FoxO3a, which were up-regulated by dexamethasone through qPCR like ebselen (see FIGS. 6F and 6G).

Figure 6A:
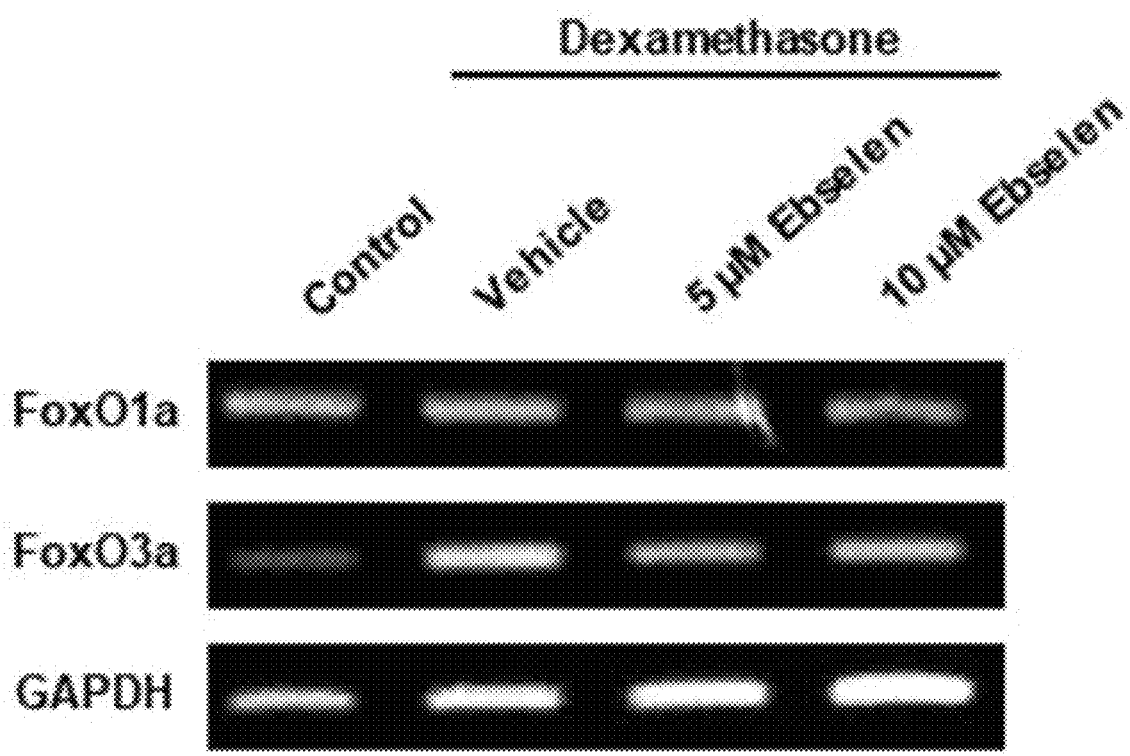
FIG. 6A shows the results of RT-PCR analysis on FoxO1a expression and FoxO3a expression in C2C12 myotubes treated with dexamethasone under different conditions and in C2C12 myotubes treated with ebselen under different conditions.
Figure 6B:
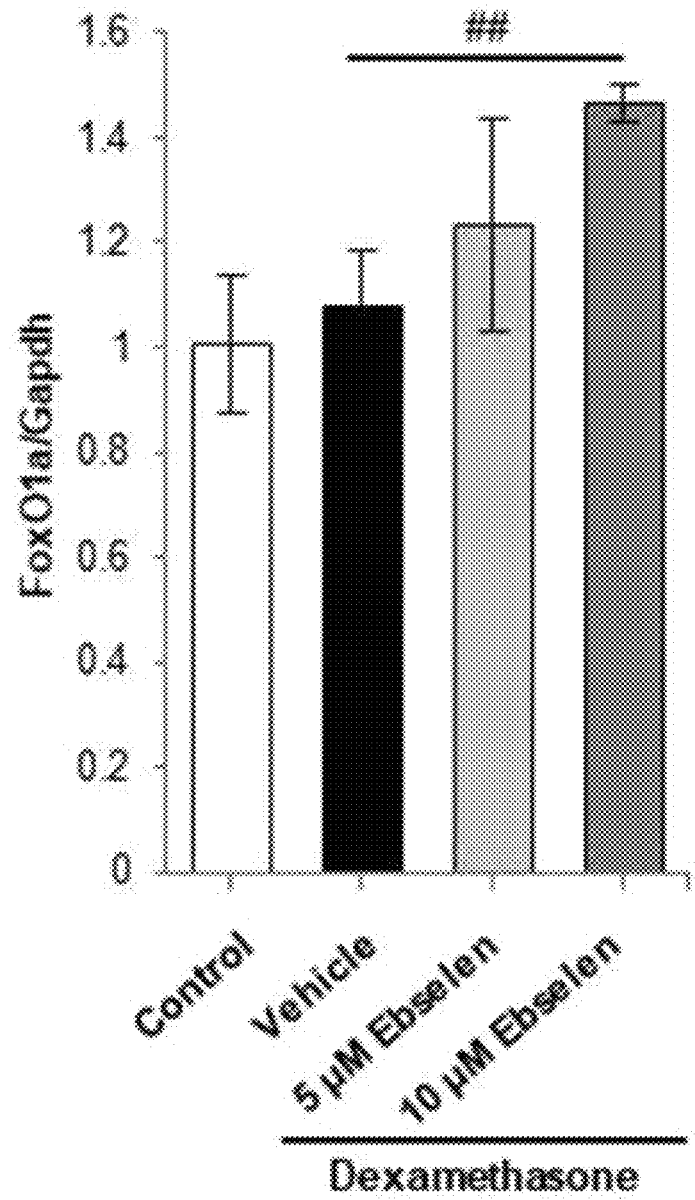
FIGS. 6B and 6C show the results of qPCR analysis on FoxO1a expression and FoxO3a expression in C2C12 myotubes (##=p<0.01, ***=p<0.001)
Figure 6C:
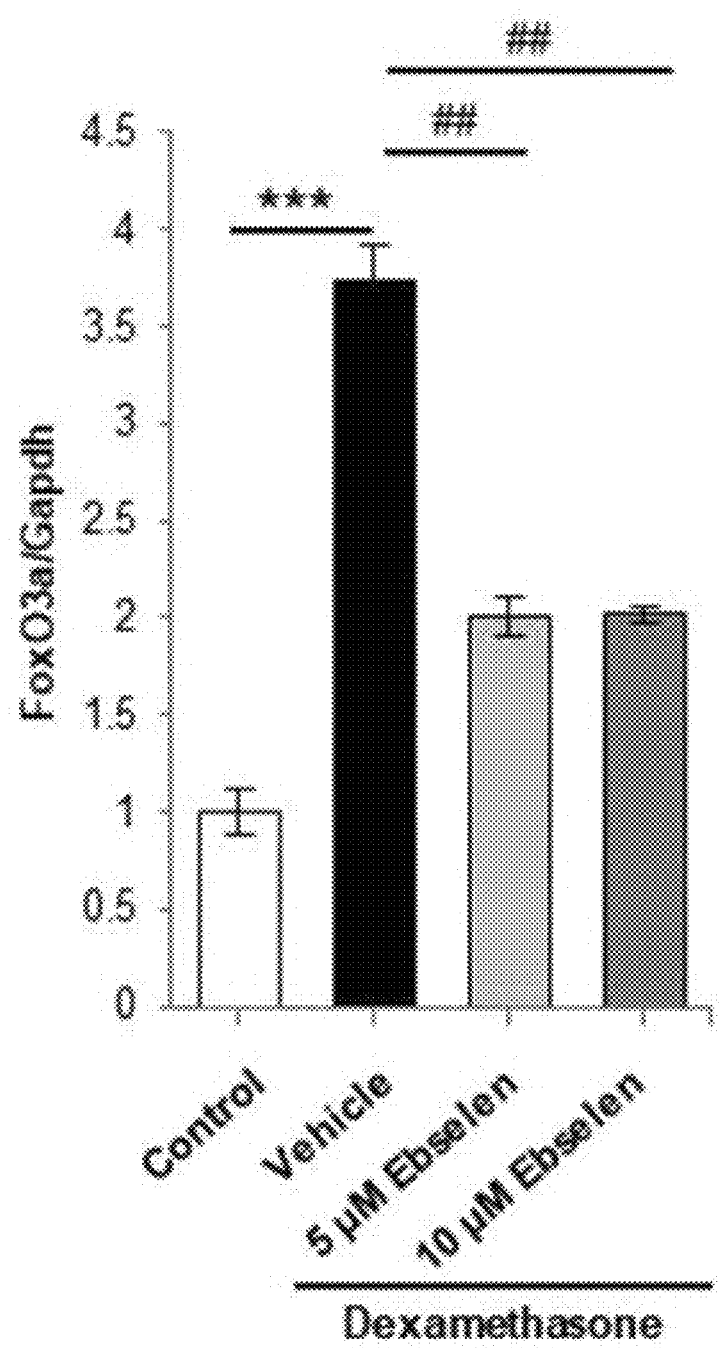
Figure 6D:
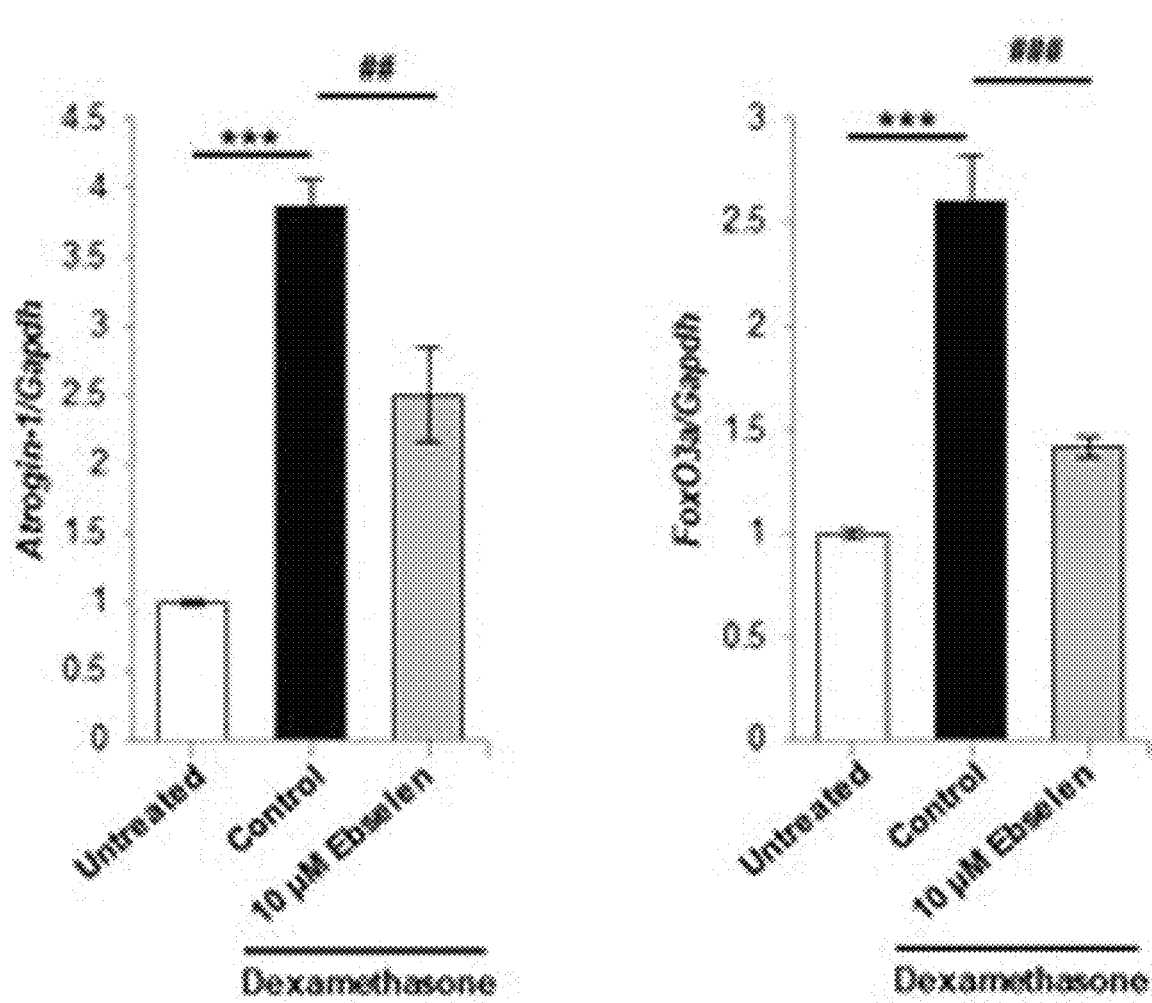
FIG. 6D shows the results of qPCR analysis on Atrogin-1 expression and FoxO3a expression in C2C12 myotubes treated with dexamethasone alone or co-treated with dexamethasone and ebselen p<0.001, ##=p<0.01, ###=p<0.001); (***=
Figure 6E:
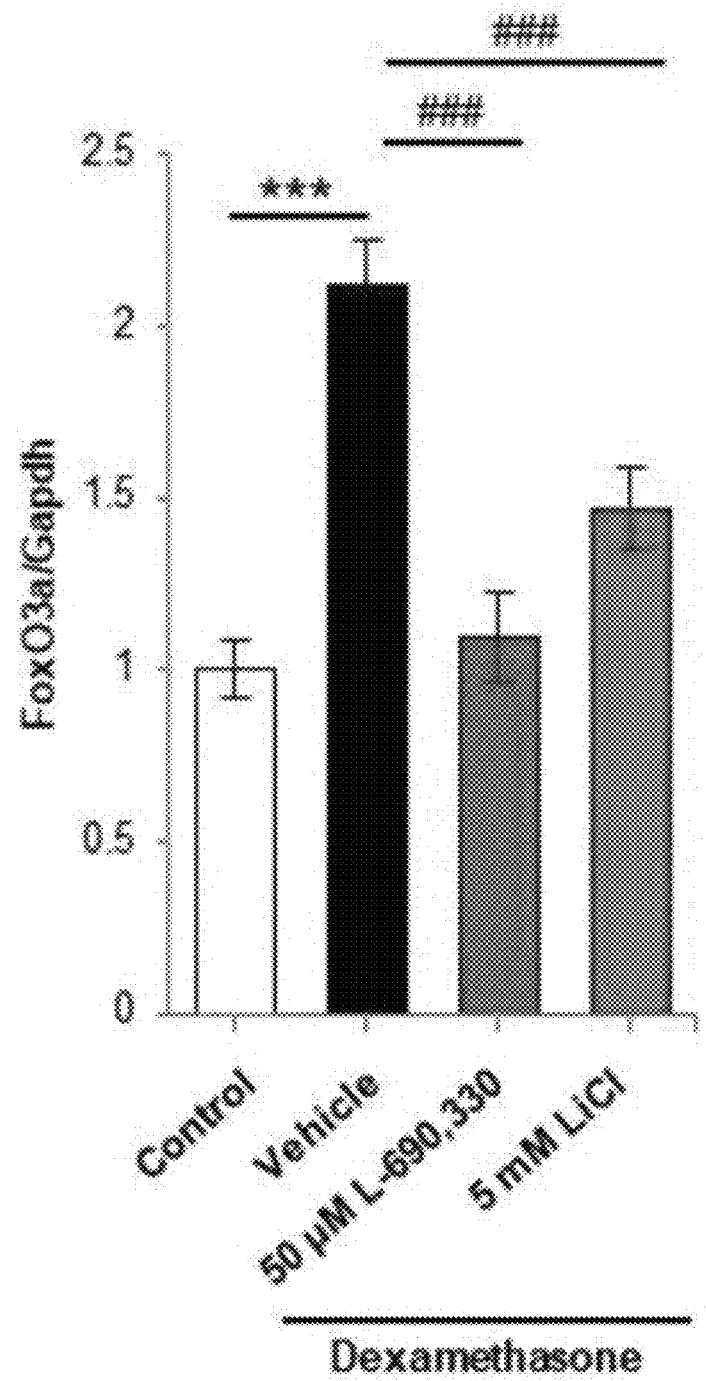
FIG. 6E shows the result of qPCR analysis on FoxO3a expression in C2C12 myotubes treated with dexamethasone alone or treated with a combination of dexamethasone and each of different IMPase inhibitors (***=p<0.001, ###=p<0.001)
Figure 6F:
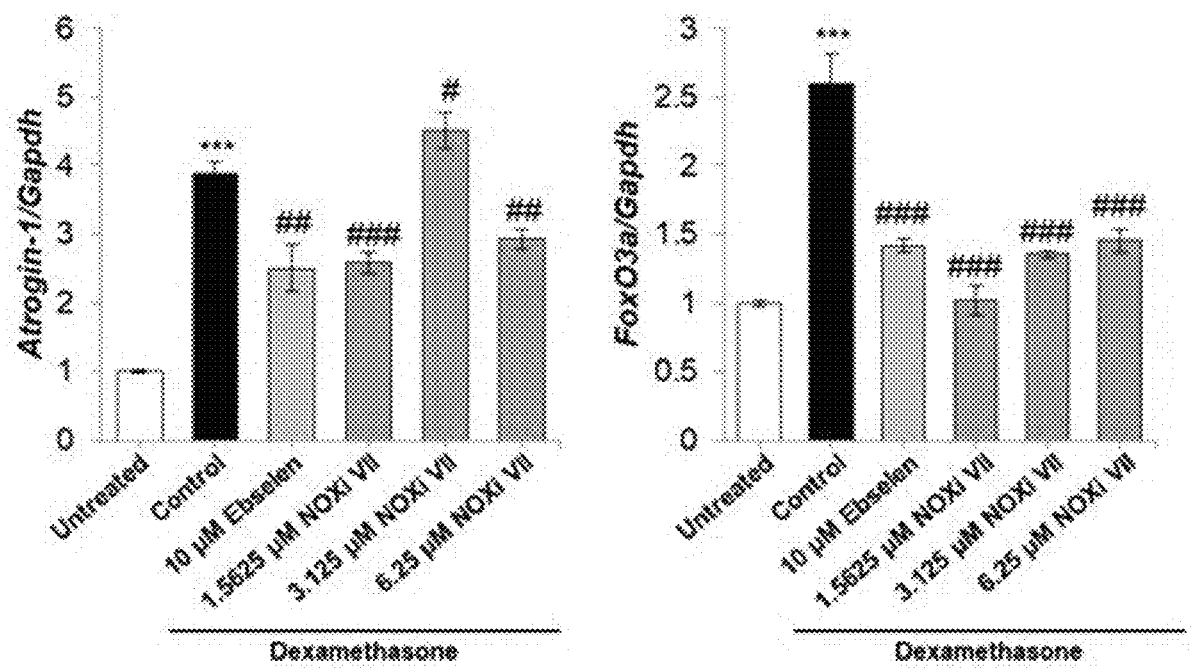
FIG. 6F shows the results of qPCR analysis on Atrogin-1 expression and FoxO3a expression in C2C12 cells after 72 hours of incubation with DM, followed by 24 hours of treatment with 10 μM dexamethasone alone or 24 hours of co-treatment with a combination of 10 μM dexamethasone and 1.5625 μM NOXi VII, a combination of 10 μM dexamethasone and 3.125 μM NOXi VII, a combination of 10 μM dexamethasone and 6.25 μM NOXi VII, or a combination of dexamethasone and 10 μM Ebselen (***=p<0.001, #=p<0.05, ##=p<0.01, and ###=p<0.001)
Figure 6G:
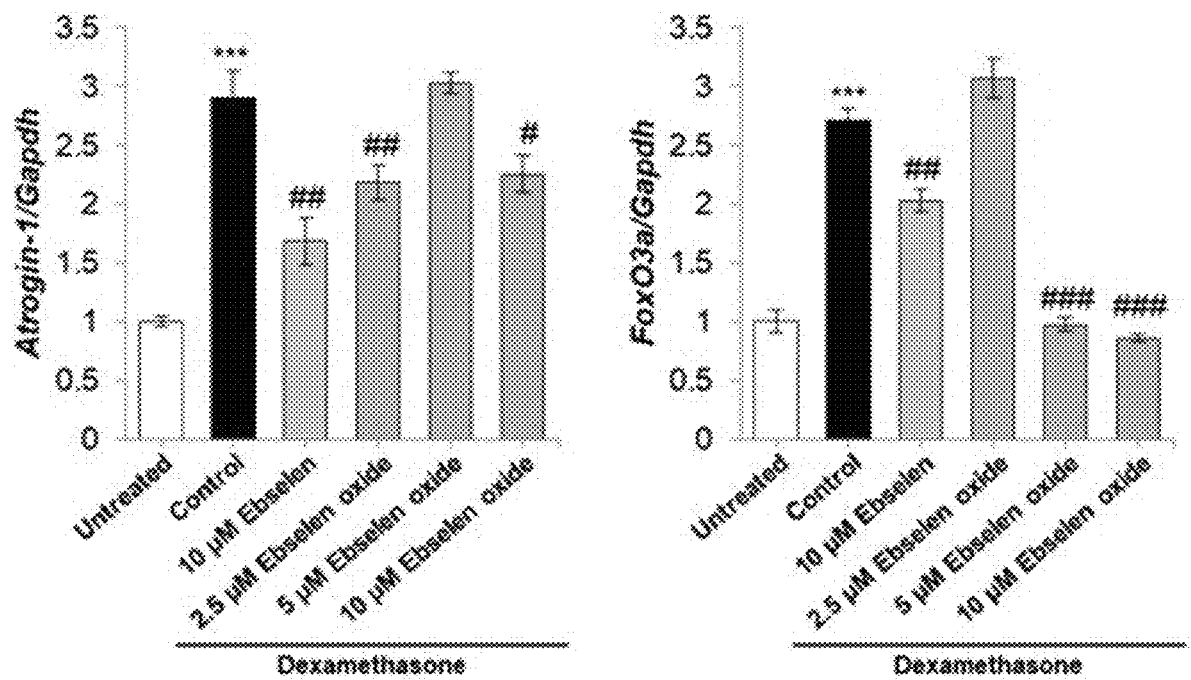
FIG. 6G shows the results of qPCR analysis on Atrogin-1 expression, MuRF-1 expression, and FoxO3a expression in C2C12 cells after 72 hours of incubation with DM, followed by 24 hours of treatment with 10 μM dexamethasone alone or 24 hours of co-treatment with a combination of 10 μM dexamethasone and 2.5 μM ebselen oxide, a combination of 10 μM dexamethasone and 5 μM ebselen oxide, a combination of 10 μM dexamethasone and 10 μM ebselen oxide, or a combination of dexamethasone and 10 μM ebselen p<0.001, #=p<0.05, ##=p<0.01, and ###=p<(***=0.001)
Figure 6H:
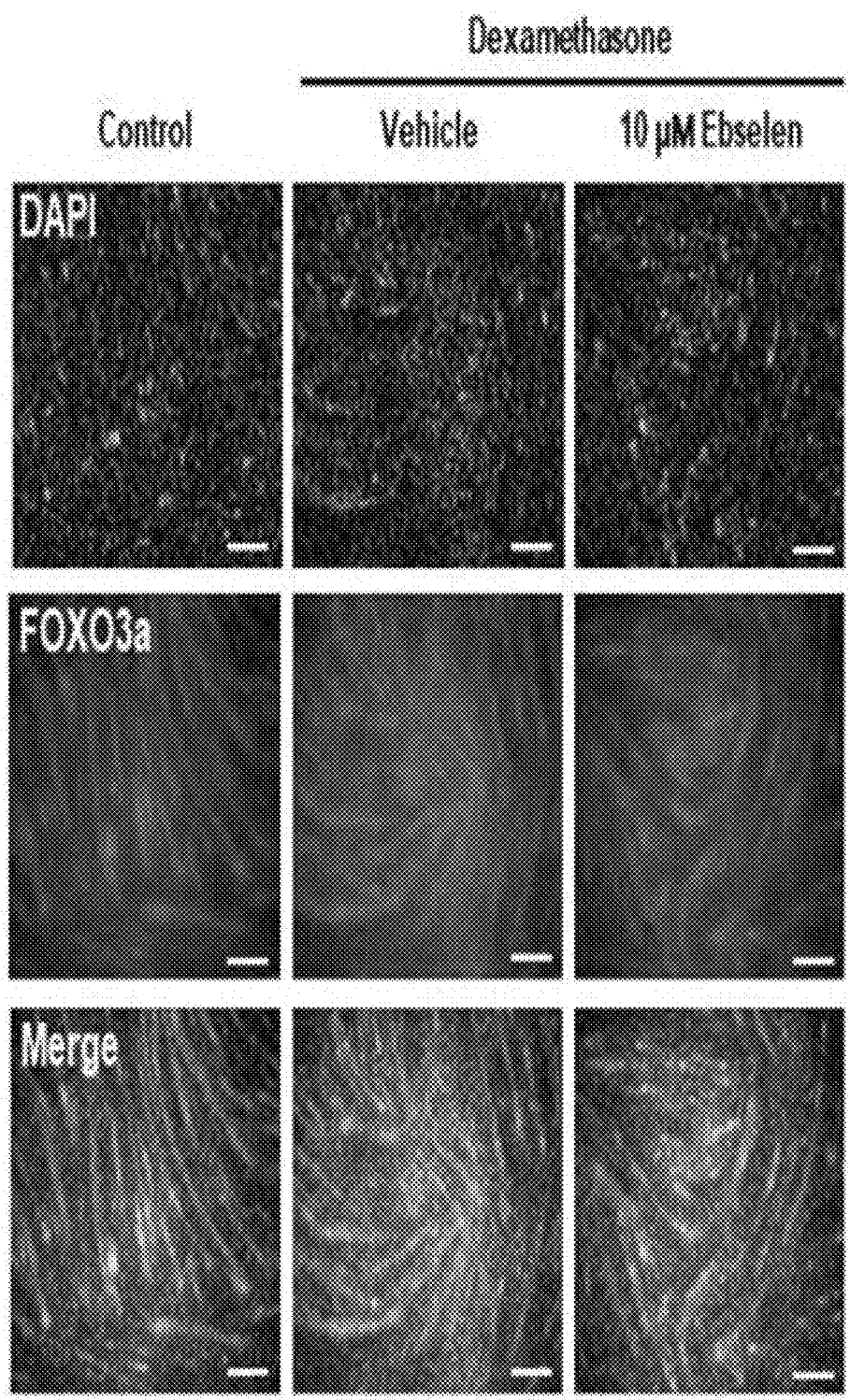
FIG. 6H shows the result of immunocytochemistry analysis of FoxO3a expression in C2C12 myotubes(scale bar=100 μm)
Figure 6I:
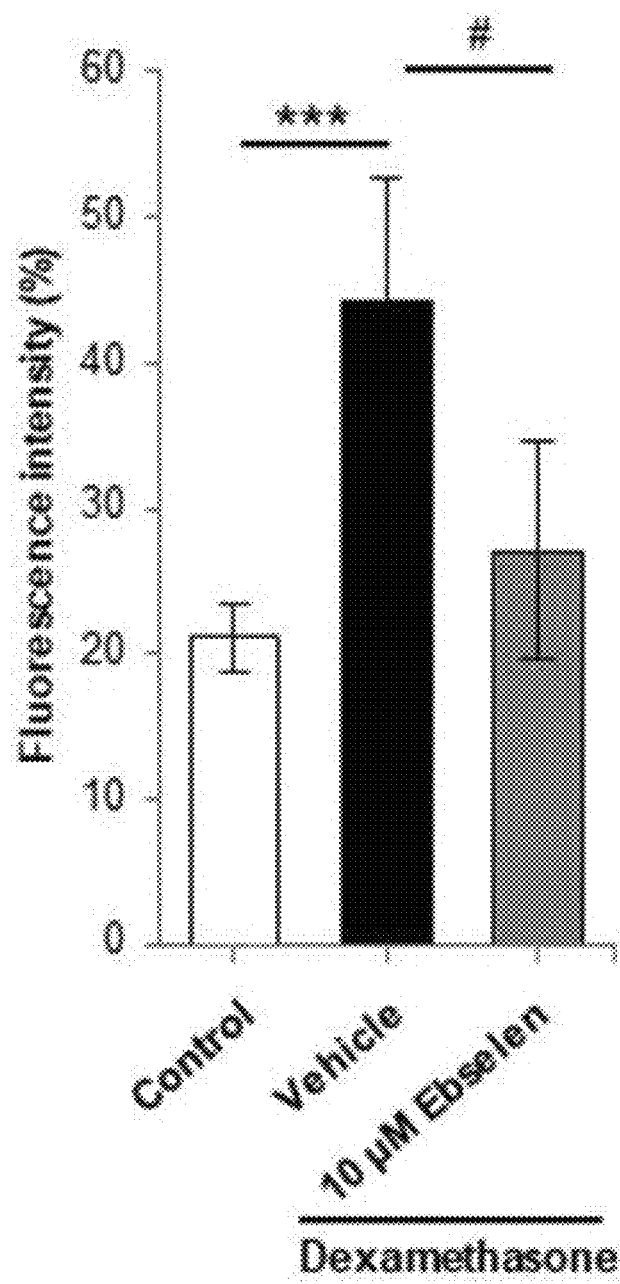
FIG. 6I is a graph of quantification of FoxO3a staining intensity (***=p<0.001, #=p<0.05)
Figure 6J:
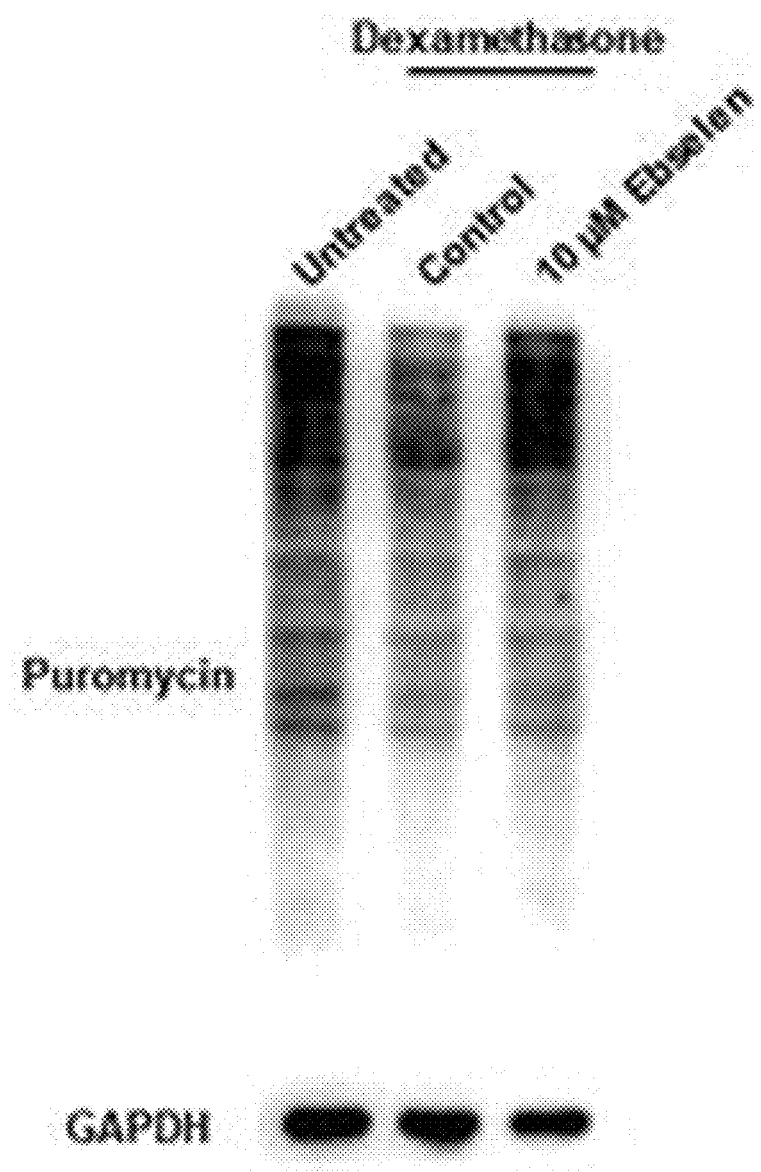
FIGS. 6J and 6K show the results of the SUnSET assay of protein synthesis in C2C12 myotubes treated with dexamethasone alone or treated with dexamethasone and ebselen (***=p<0.001, ##=p<0.01)
Figure 6K:
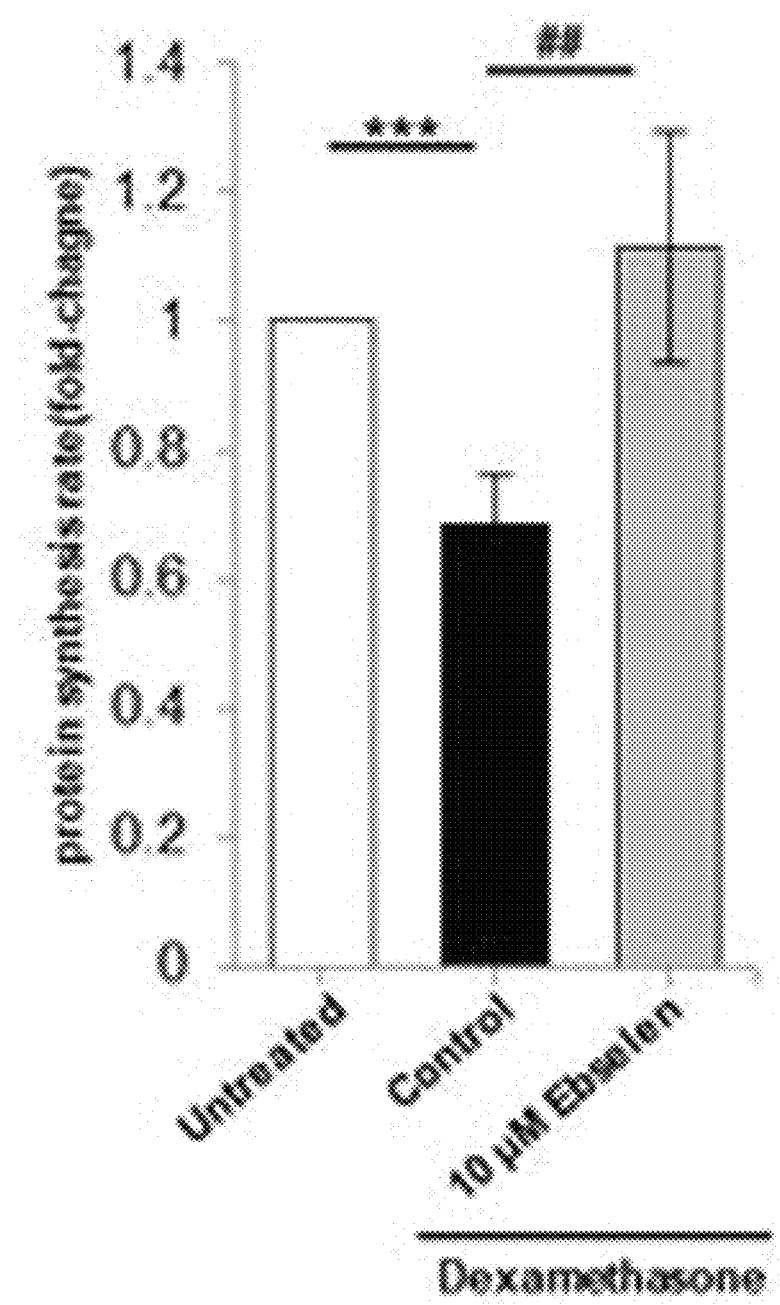

In addition, it was confirmed through immunocytochemistry analysis that FoxO3a up-regulation caused by dexamethasone was inhibited by ebselen (see FIGS. 6H and 6I).

Protein synthesis in myotubes treated with myo-inoistol, dexamethasone, and IMPase inhibitors was measured through the SUnSET assay. As a result, ebselen, which is an IMPase inhibitor, increased protein synthesis in dexamethasone-treated myotubes (see FIGS. 6J and 6K).

Figure 6L:
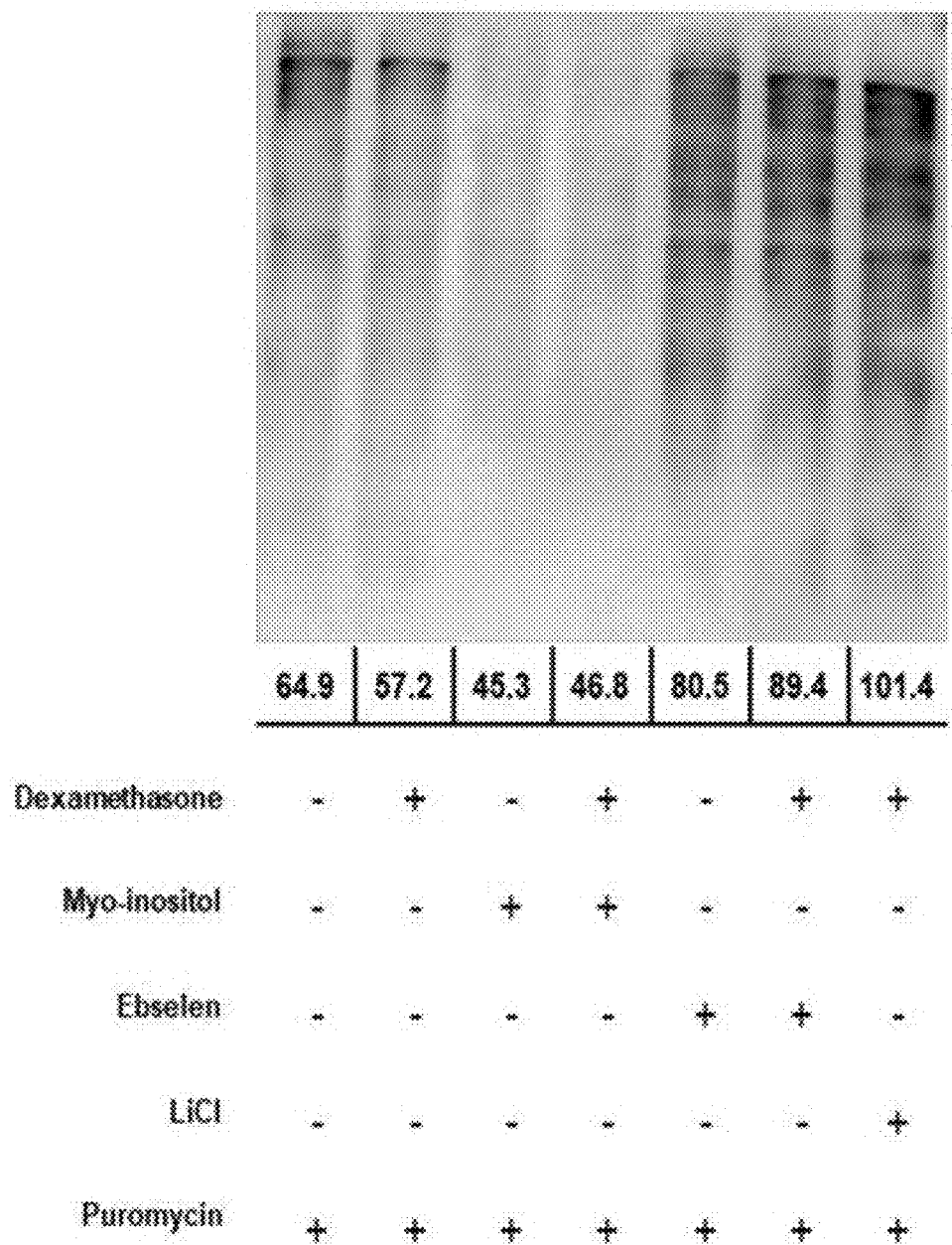
FIG. 6L shows the result of the SUnSET assay of protein synthesis in C2C12 myotubes treated with each drug (a number below each lane indicates the band intensity of puromycin-labeled protein)

Treatment with myo-inositol alone or co-treatment with dexamethasone decreased protein synthesis, and it was confirmed that ebselen was effective in increasing protein synthesis when myotubes were treated alone or in the presence of dexamethasone (see FIG. 6L).

Example 7: Confirmation of Inhibitory Effect of Ebselen on Skeletal Muscle Atrophy—in Vivo The inhibitory effect of ebselen on IMPase activity was confirmed in a dexamethasone-treated mouse model. Co-treatment with dexamethasone and ebselen caused significant weight loss compared to untreated mice (see FIG. 7A).

Figure 7A:
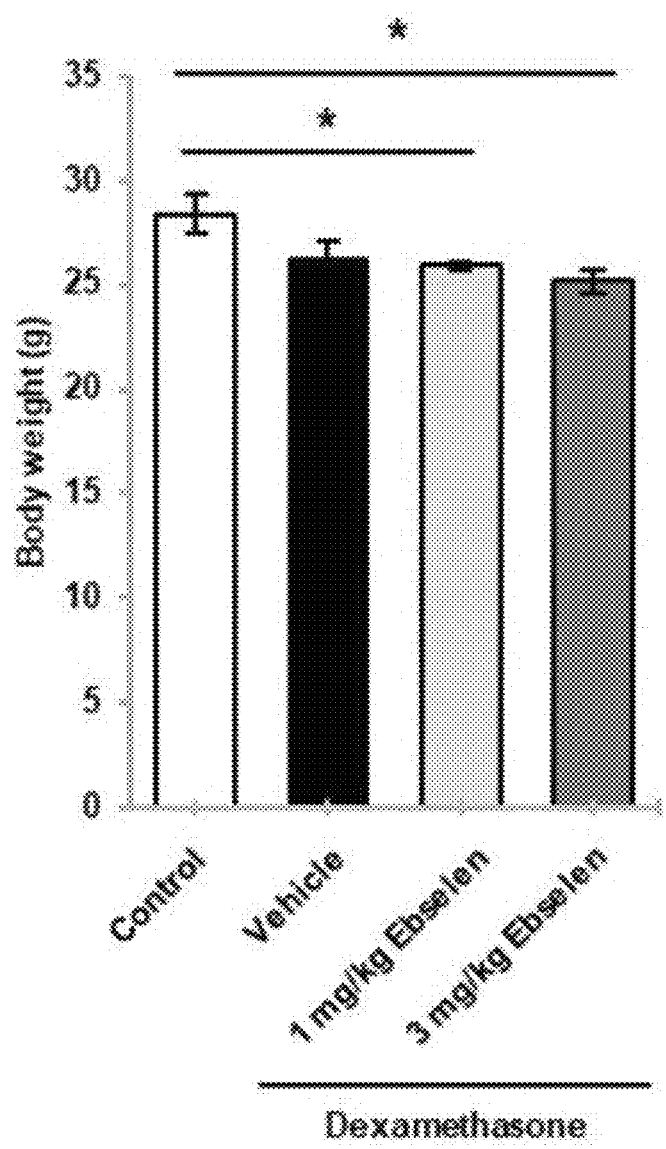
FIG. 7A shows the change in body weight of ebselen-treated mice using the dexamethasone treatment model of skeletal muscle atrophy (*=p<0.05)
Figure 7B:
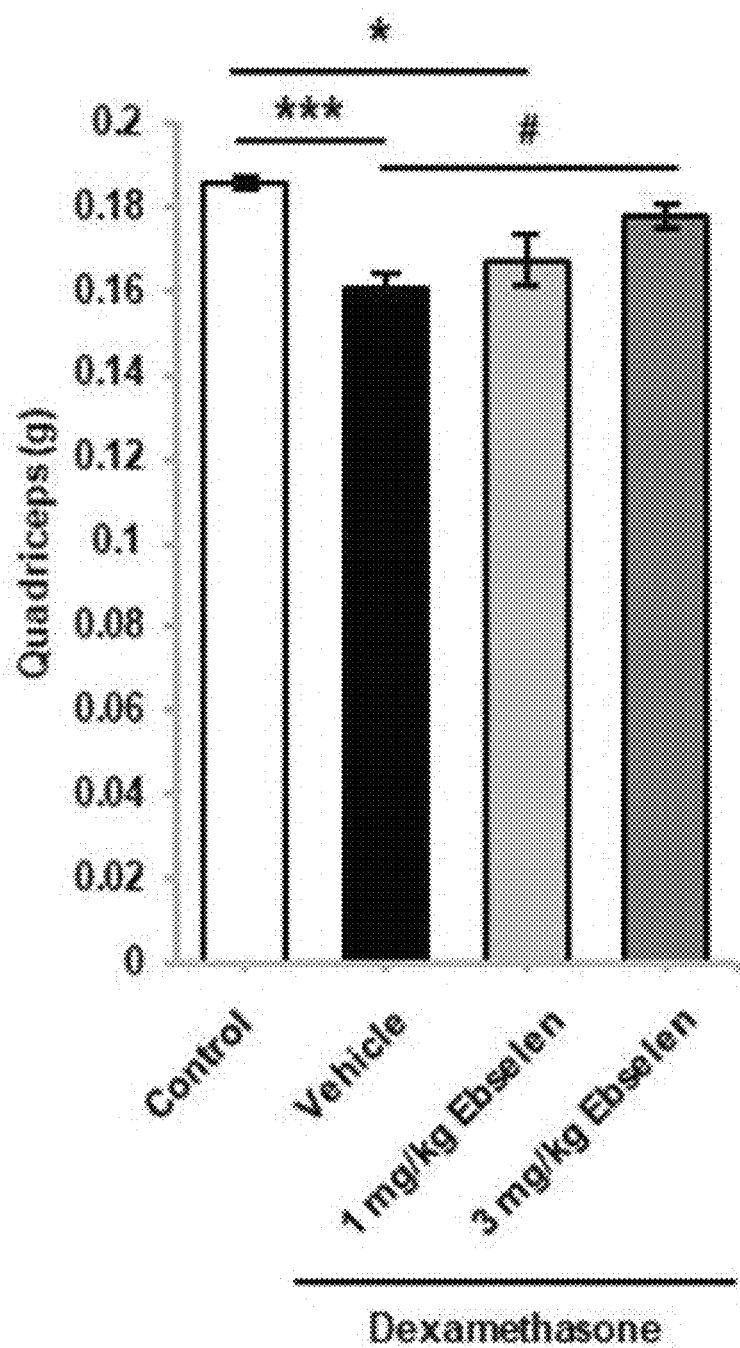
FIG. 7B shows the quadriceps muscle mass of ebselen-treated mice using the dexamethasone treatment model of skeletal muscle atrophy (*=p<0.05, ***=p<0.001, #=p<0.05)
Figure 7C:
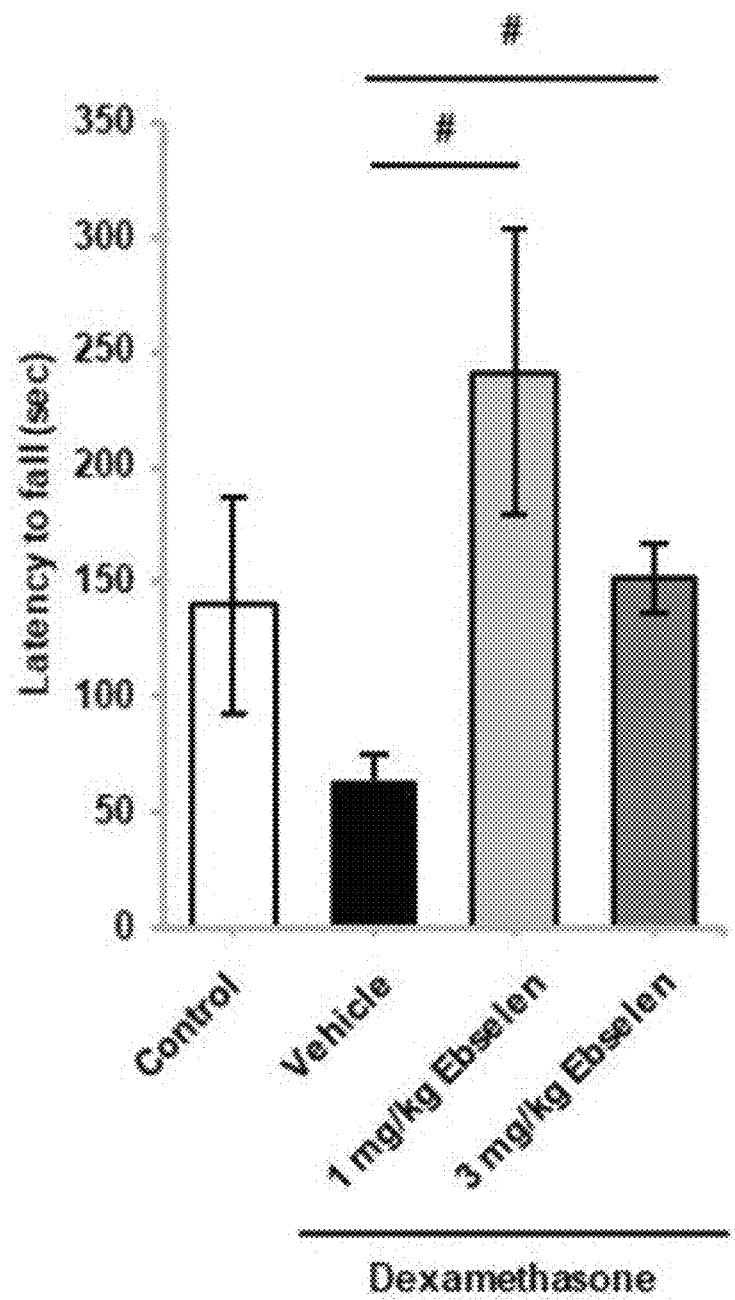
FIG. 7C shows the result of a muscle endurance test with a hanging tolerance test for the ebselen-treated mice, using the dexamethasone treatment model of skeletal muscle atrophy (#=p<*=p<0.05)
Figure 7D:
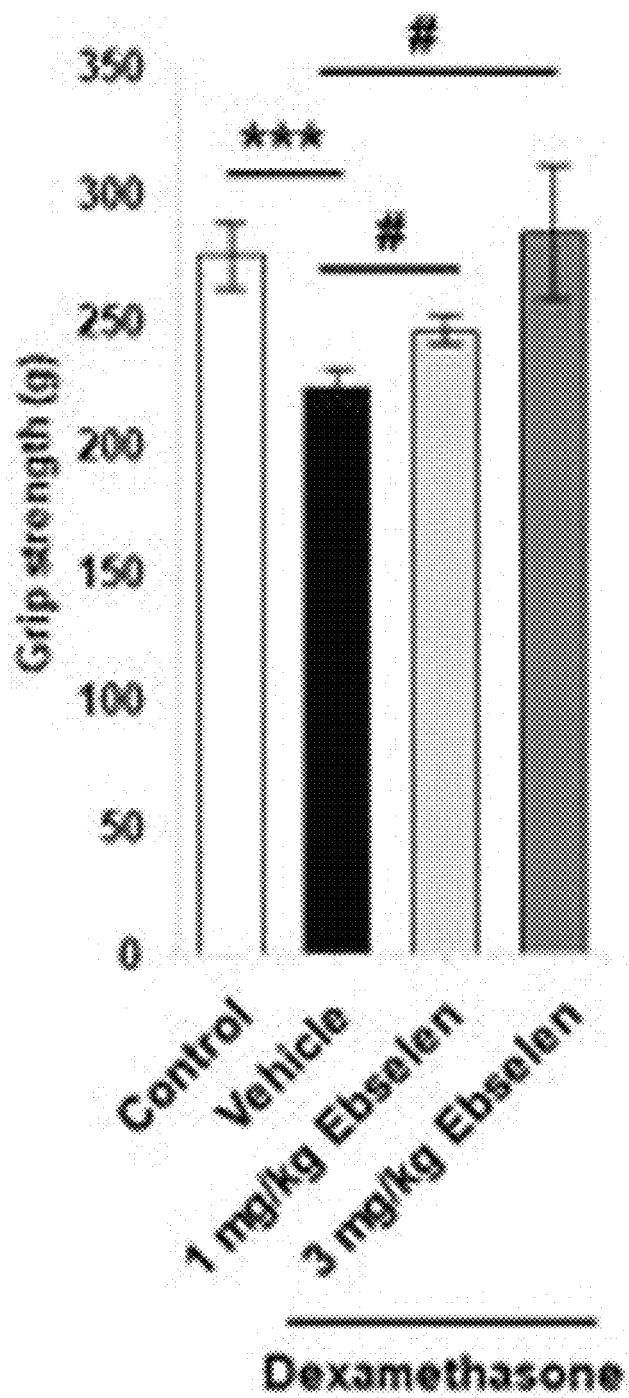
FIG. 7D shows the result of a muscle strength test measuring grip strength for ebselen-treated mice using the dexamethasone treatment model of skeletal muscle atrophy (***=p<0.001, #=p<0.05)
Figure 7E:
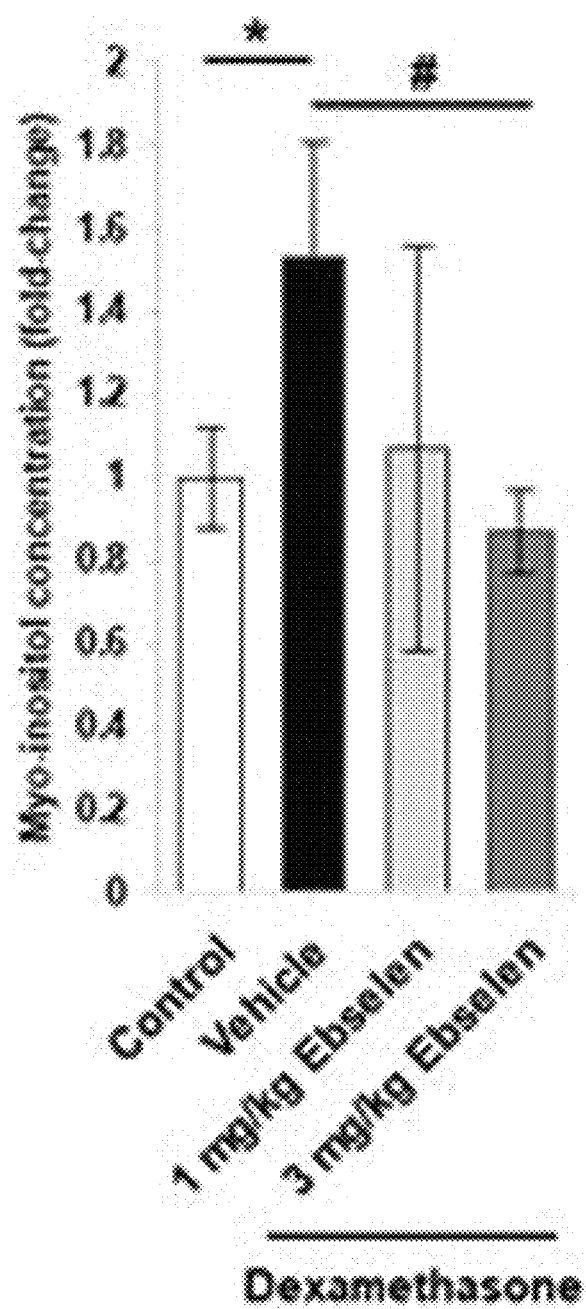
FIG. 7E is a graph showing a result of comparison in IMPase activity in the quadriceps muscle between mice treated with dexamethasone alone and mice treated with dexamethasone and ebselen (*=p<0.05, #=p<0.05)

Mice treated with dexamethasone showed a significant decrease in quadriceps mass, and it was confirmed that the reduced quadriceps mass was recovered by ebselen treatment (see FIG. 7B).

In addition, skeletal muscle performance was assessed using the inverted hanging and grip strength tests. The results of the tests showed that ebselen treatment significantly enhanced hanging time and grip strength compared to dexamethasone-treated mice (see FIGS. 2C and 2D). In the case of the quadriceps of dexamethasone-treated mice, IMPase activity was increased and the concentration of myo-inositol was increased due to the accumulation of myo-inositol in the muscle (See FIG. 7E).

Figure 7F:
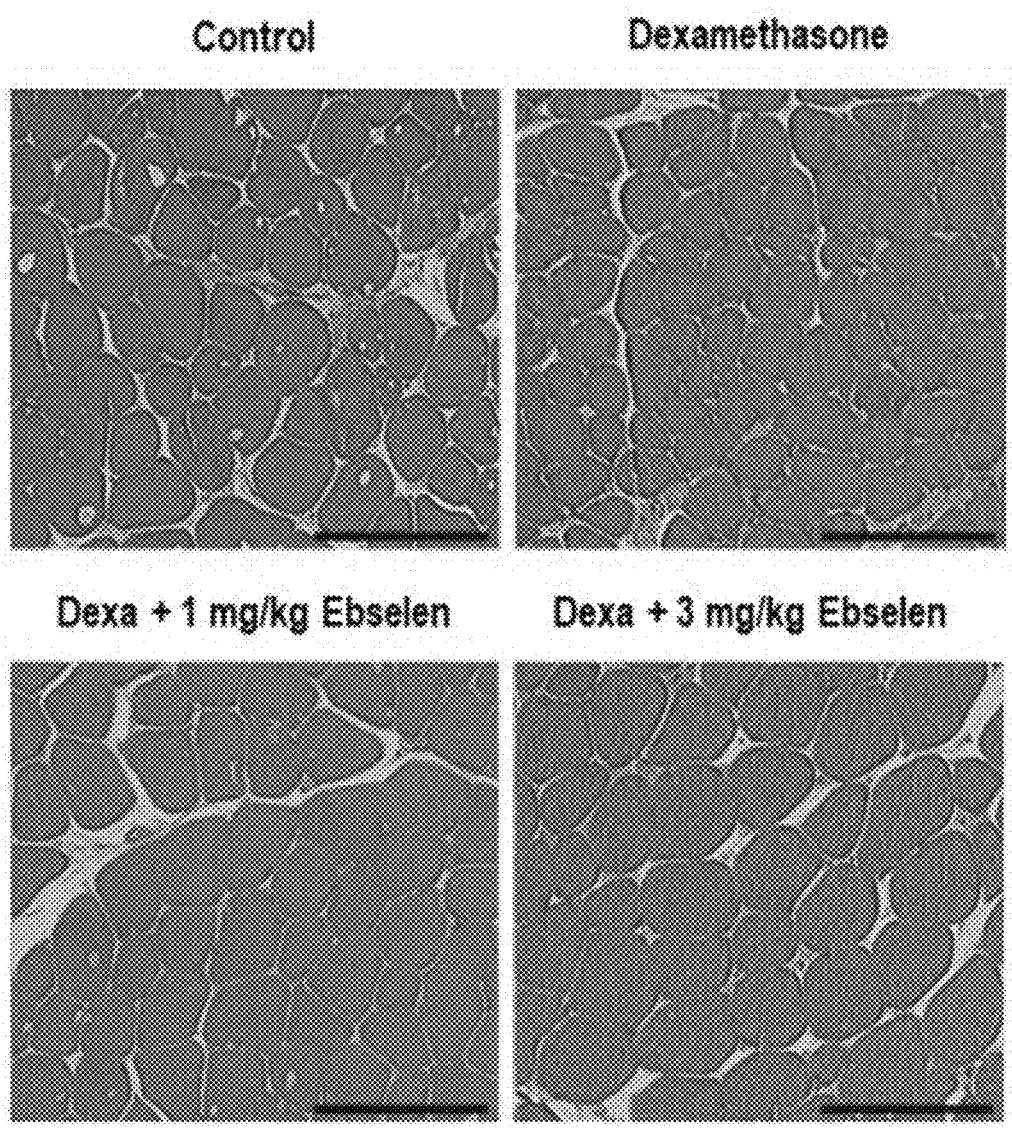
FIG. 7F shows representative images of hematoxylin and eosin (H&E)-stained quadriceps muscle (scale bar=200 μm)
Figure 7G:
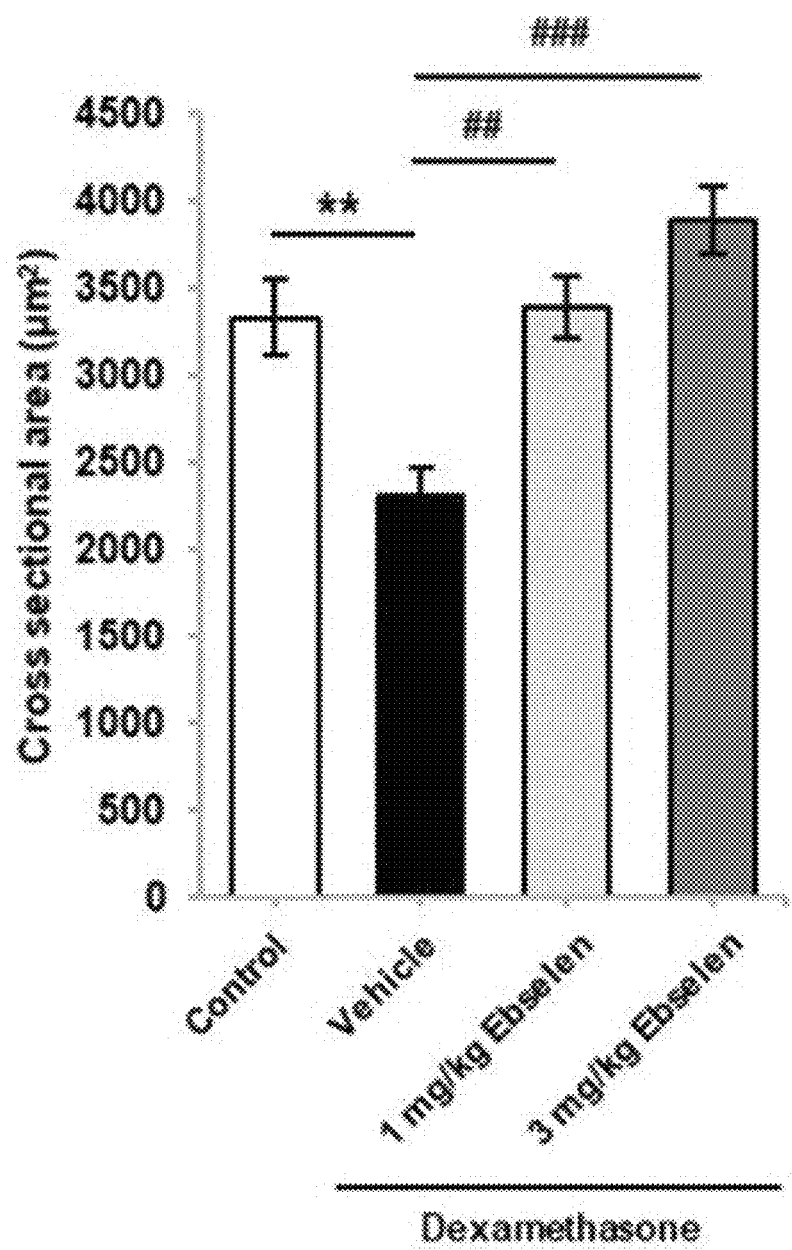
FIG. 7G shows the average cross-sectional area of the quadriceps muscle of the ebselen-treated mice using the dexamethasone treatment model(##=p<0.01, **=p<0.01)
Figure 7H:
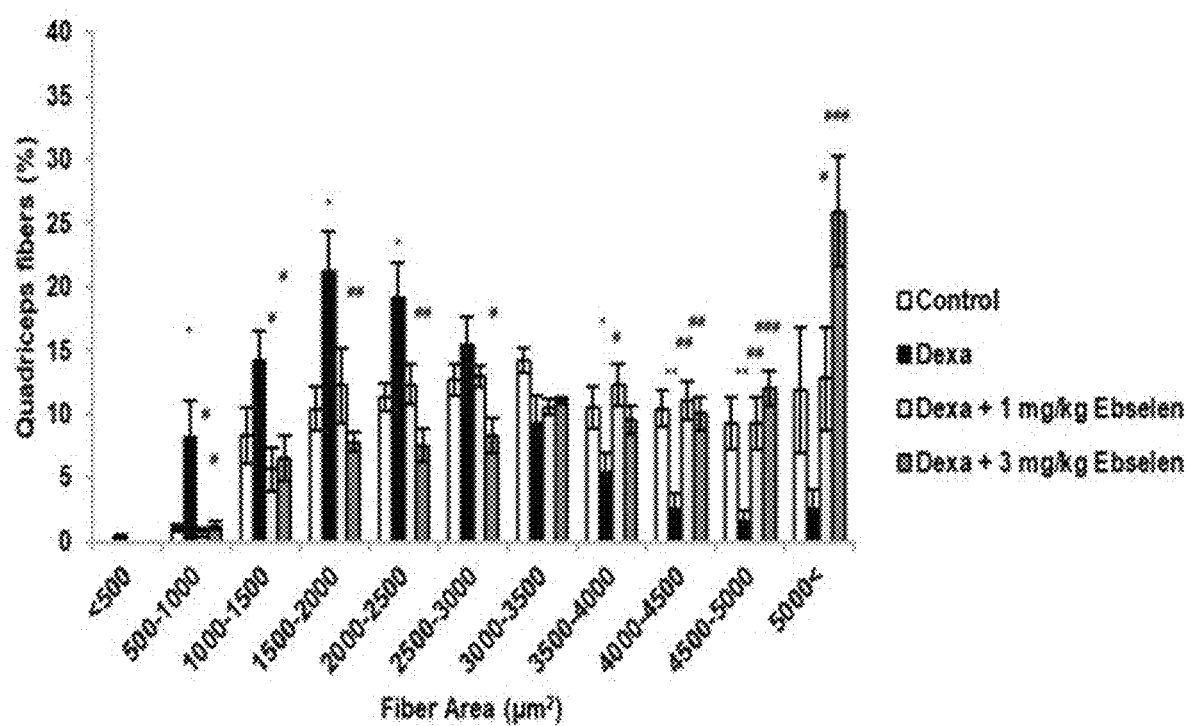
FIG. 7h shows a distribution of fibrous cross-sectional areas of the quadriceps muscle of ebselen-treated mice, using the dexamethasone treatment model of skeletal muscle atrophy (*=p<0.05 and **=p<0.01, #=p<0.05, ##=p<0.01 and ###=p<0.001)
Figure 7I:
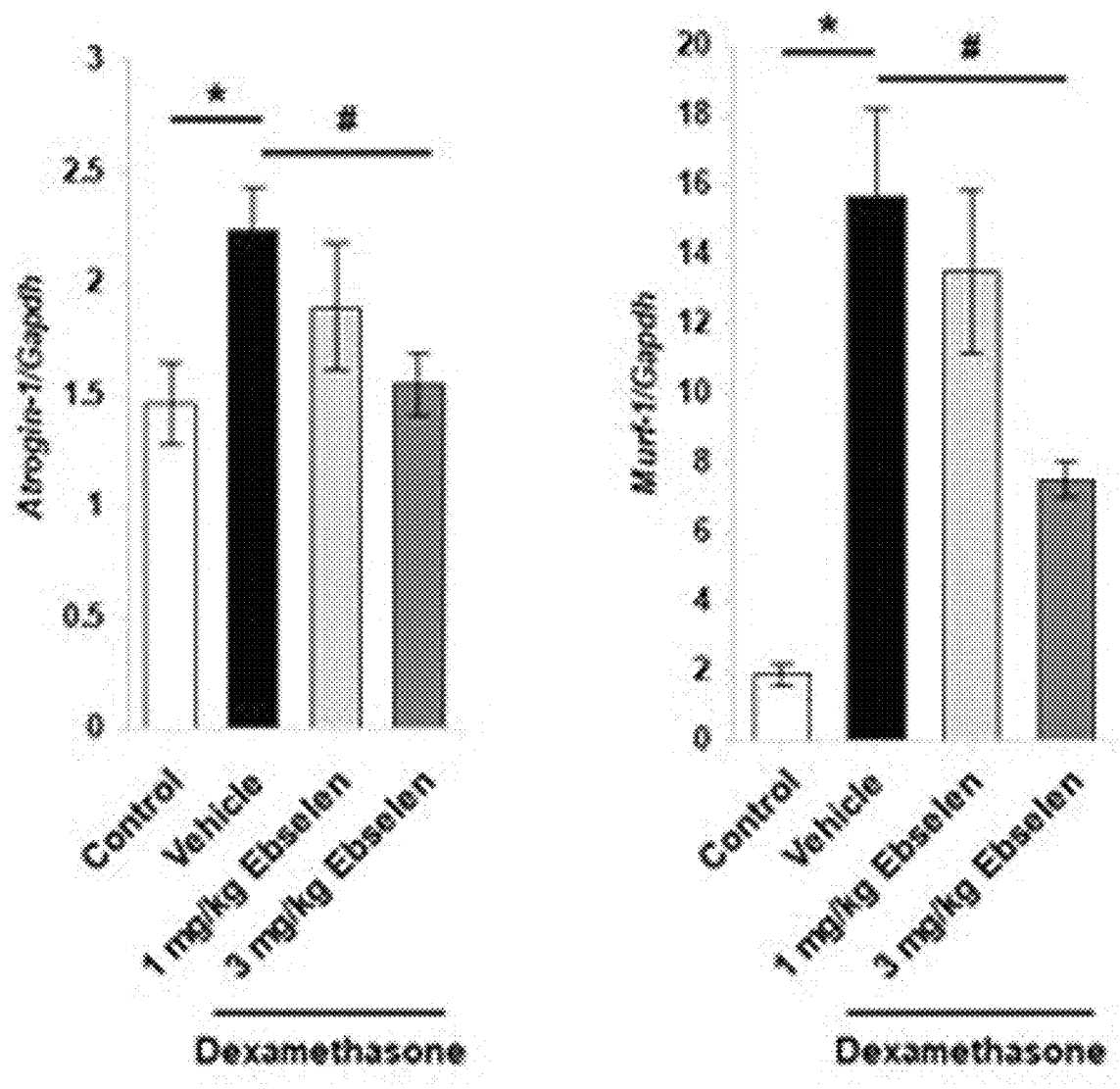
FIG. 7I shows the results of qPCR analysis on Atrogin-1 expression and MuRF-1 expression in the quadriceps muscles of mice treated with dexamethasone alone and of mice co-treated with dexamethasone and ebselen (*=p<0.05, #=p<0.001)

In addition, according to histological analysis of the quadriceps, ebselen increased the muscle fiber cross-sectional area and the ratio of larger fibers (see FIGS. 7F to 7H).

The expression of Atrogin-1 and Murf-1 in the quadriceps was confirmed through qPCR assay. It was confirmed that the expression of Atrogin-1 and Murf-1 increased by dexamethasone treatment was effectively reduced by ebselen treatment (see FIG. 7I).

Example 8: Confirmation of Inhibitory Effect of Ebselen on Glycerol-induced Skeletal Muscle Degeneration—in Vivo The therapeutic effect of ebselen on muscle dystrophy was additionally investigated in a glycerol injury model. This model produces adipocyte deposition and fibrous tissue accumulation which are observed in the case of sarcopenia and are the major causes of muscle weakness. Since ebselen has been approved as an oral drug for humans, mice with glycerol-induced muscle degeneration were orally treated with ebselen.

Figure 8A:
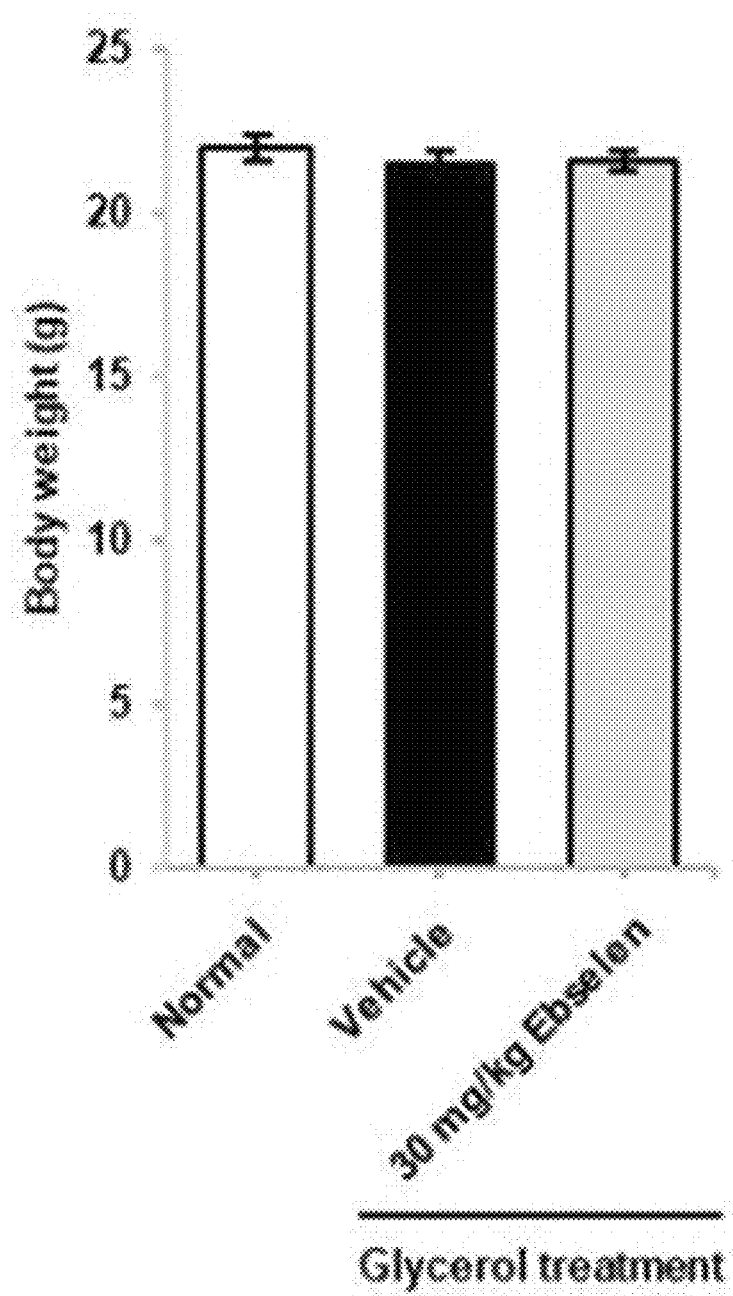
FIG. 8A shows change in the body weight of ebselen-treated mouse with glycerol-induced skeletal muscle damage.
Figure 8B:
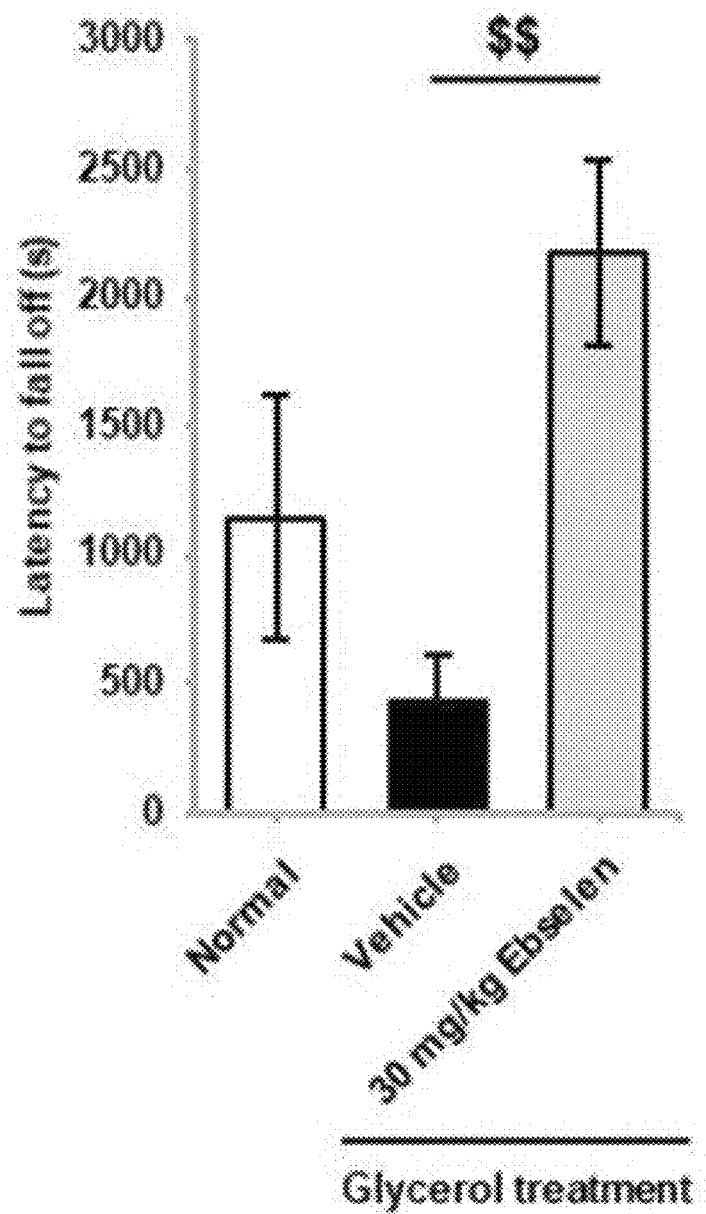
FIG. 8B shows that the duration of exercise in a Rotarod system is reduced when mice with glycerol-induced muscle damage are treated with ebselen ($=p<0.05)
Figure 8C:
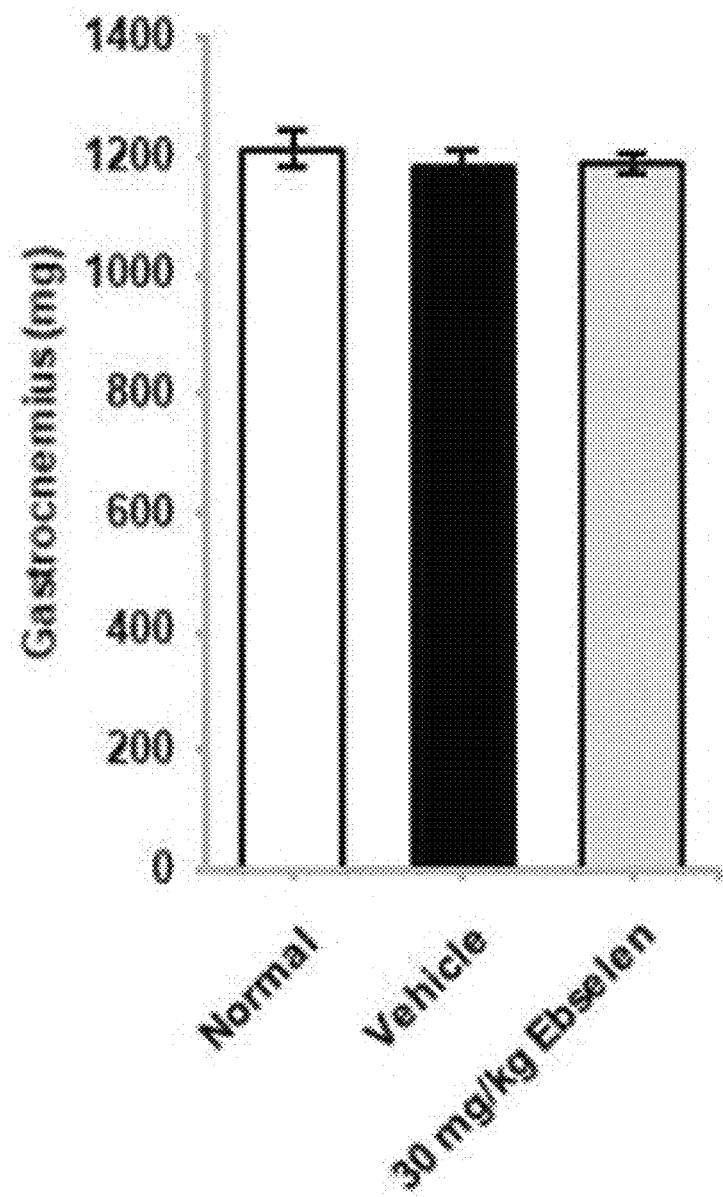
FIG. 8C shows the result of comparison in gastrocnemius mass between mice treated with vehicle and mice treated with ebselen.
Figure 8D:
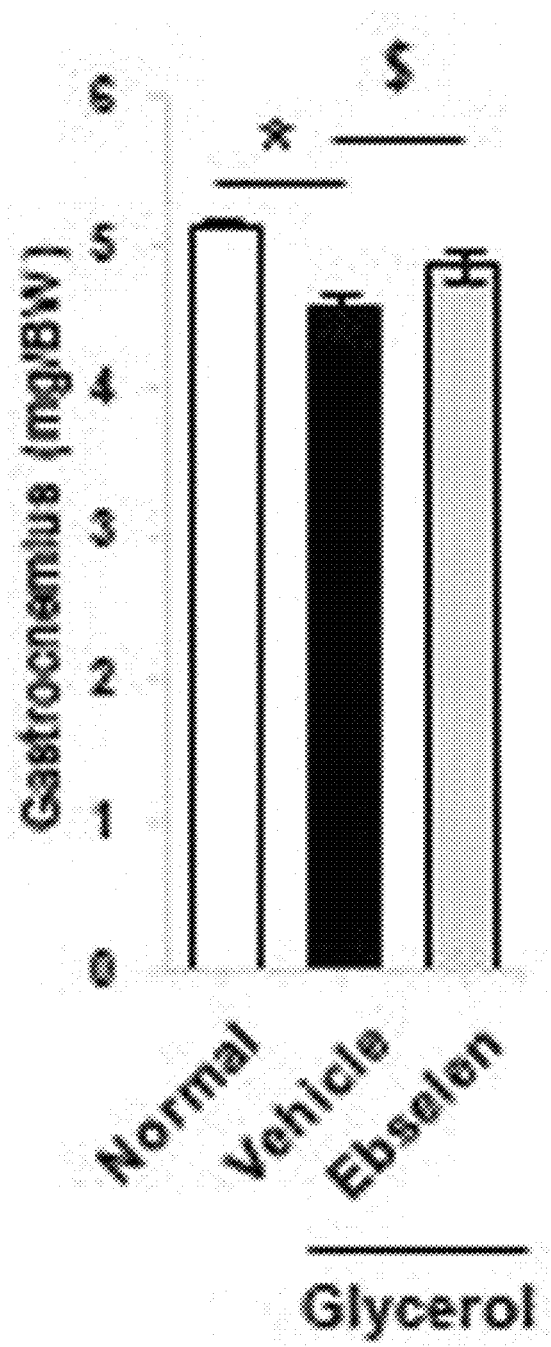
FIG. 8D shows the mass of gastrocnemius muscle damaged by glycerol injection and the recovered mass of the gastrocnemius muscle after ebselen treatment (*=p<0.05, $=p<0.05)
Figure 8E:
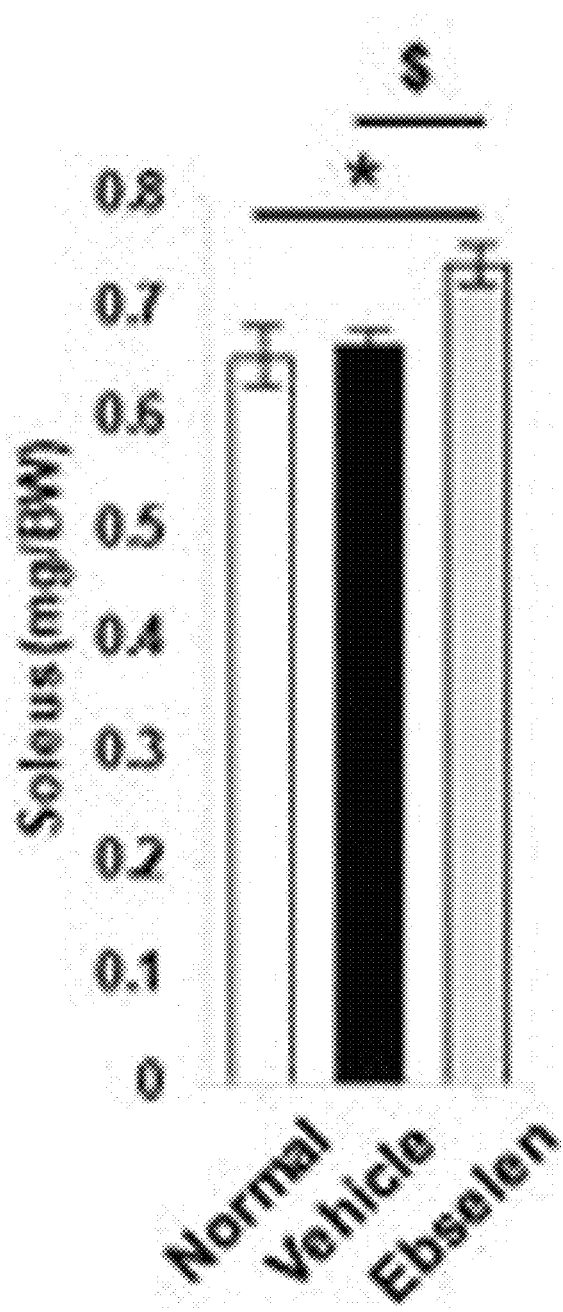
FIG. 8E shows the result of comparison in soleus muscle mass between mice treated with vehicle and mice treated with ebselen (*=p<0.05, $=p<0.05)

As a result of treatment with glycerol in the presence or absence of ebselen, there was no significant difference in mouse body weight (see FIG. 8A). The results of the Rotarod test showed that ebselen treatment improved muscle endurance (see FIG. 8B). In addition, oral treatment with ebselen did not affect gastrocnemius mass in non-injected muscles (FIG. 8C), glycerol injection reduced gastrocnemius muscle mass, and the muscle mass was increased by ebselen treatment (FIG. 8D).

Figure 8F:
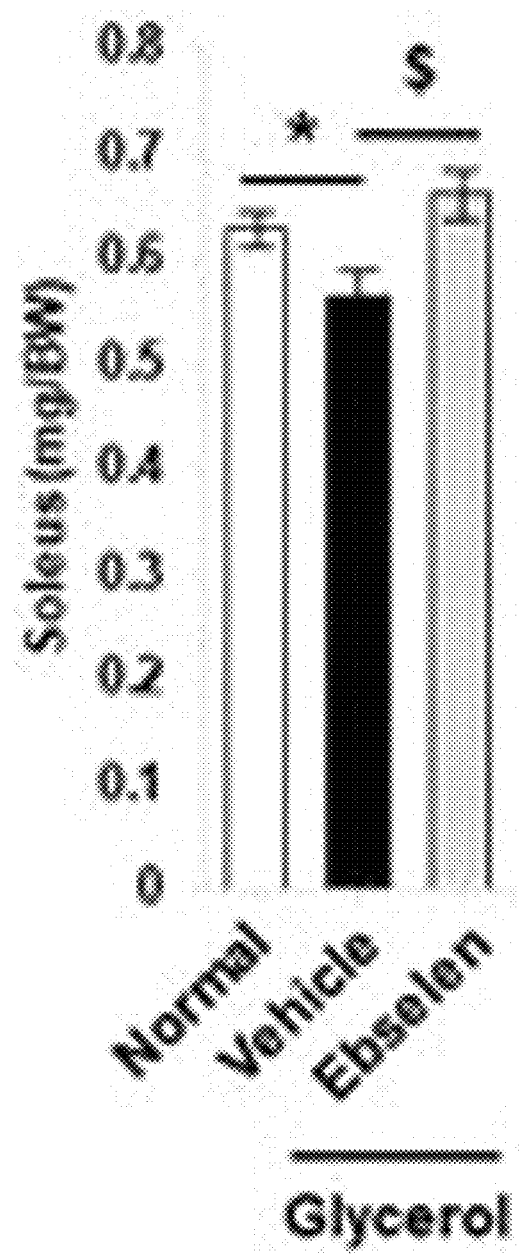
FIG. 8F shows the mass of soleus muscle damaged by glycerol injection and the recovered mass of the soleus muscle after ebselen treatment (*=p<0.05, $=p<0.05)

Interestingly, glycerol injection into the splenic muscle significantly reduced the mass of the non-injected contralateral splenic muscle (FIG. 8E), and the mass loss of the glycerol-injected splenic muscle was significantly inhibited by ebselen treatment (FIG. 8F).

Figure 8G:
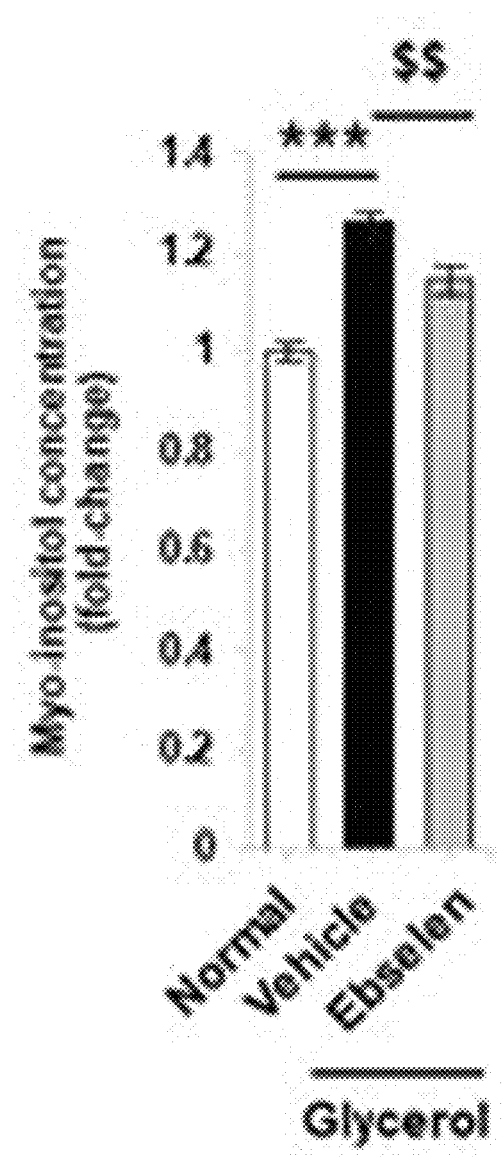
FIG. 8G shows the result of comparison in IMPase activity in the gastrocnemius muscle between mice treated with glycerol and mice treated with glycerol and ebselen (***=p<0.001, $$=p<0.01)
Figure 8H:
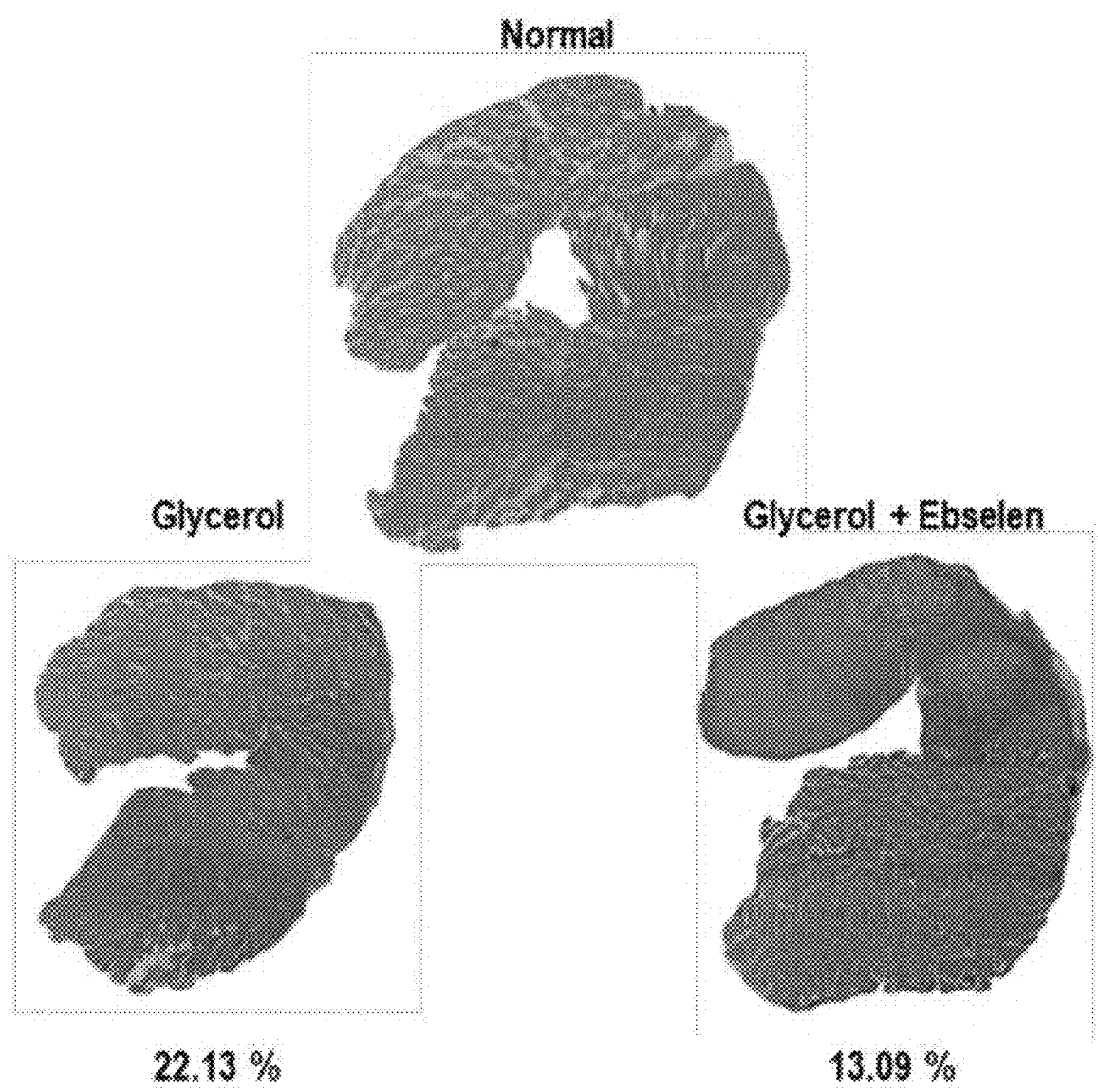
FIG. 8H shows H&E-stained gastrocnemius muscle, in which the number under each section represents the proportion of damaged area (%)
Figure 8I:
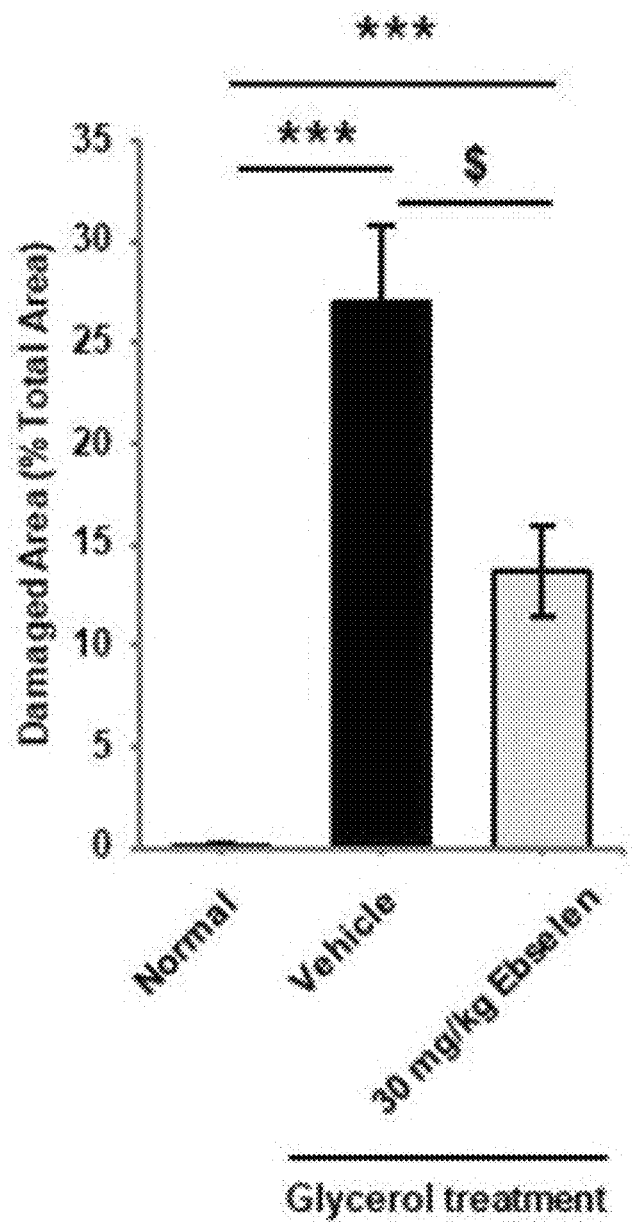
FIG. 8I shows the quantification of gastrocnemius muscle damage by glycerol injection and the reduction in the damage muscle range by ebselen treatment (***=p<0.001, $=p<0.05)

The accumulation of myo-inositol occurred in gastrocnemius muscle damaged by glycerol, and it was confirmed that the concentration of myo-inositol decreased by ebselen treatment (FIG. 8G).

Figure 8J:
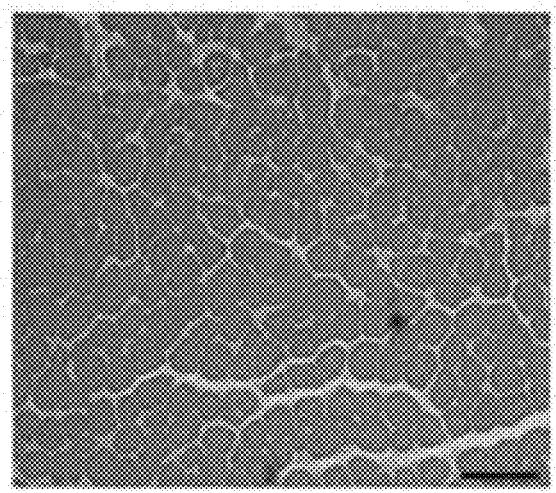
FIG. 8J shows a cross section of H&E-stained gastrocnemius muscle after treatment with glycerol or after cotreatment with glycerol and ebselen (scale bar=200 μm)
Figure 8J:
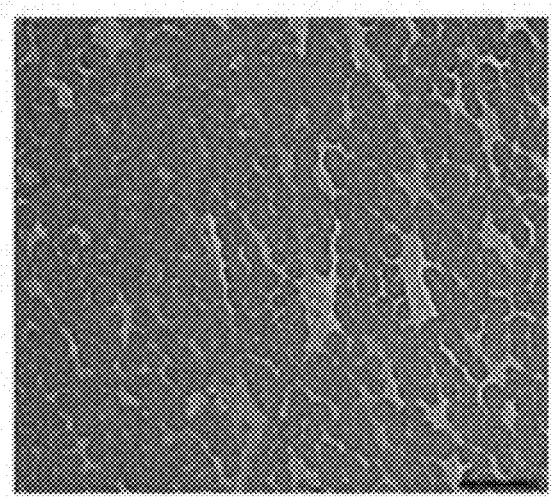
Figure 8J:
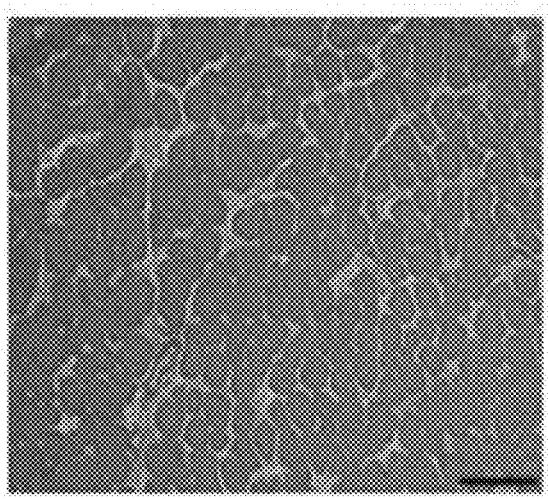
Figure 8K:
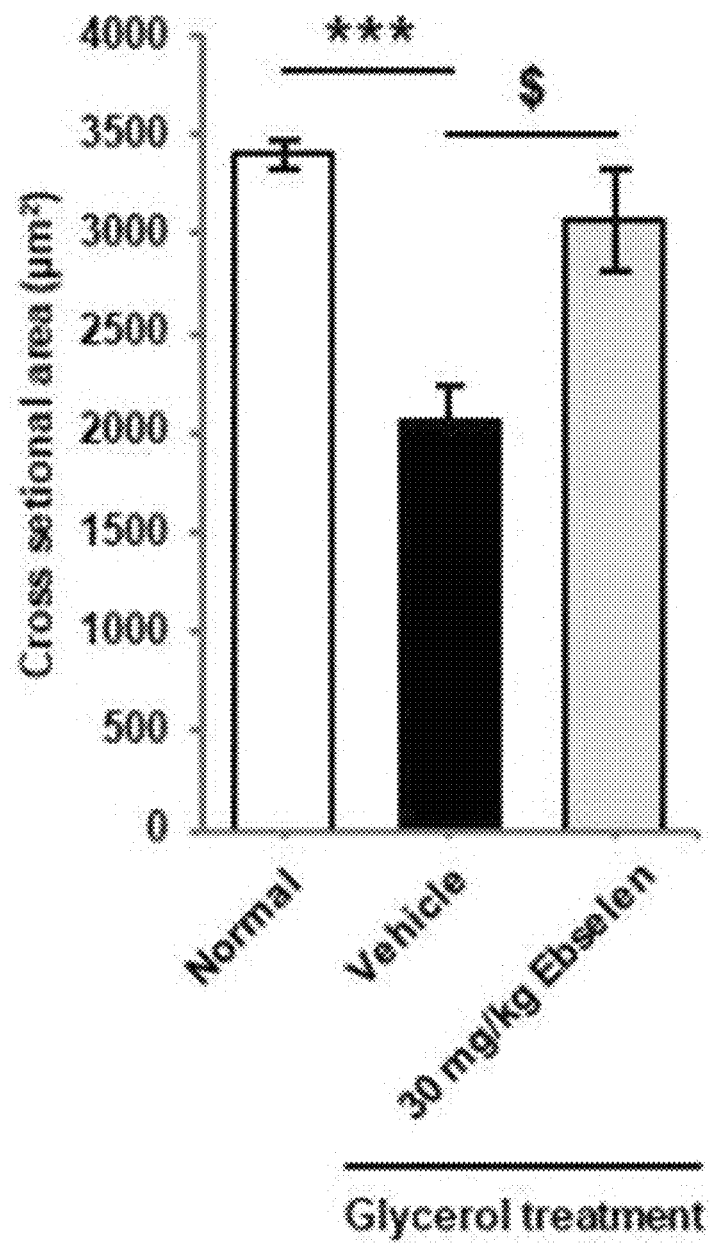
FIG. 8K shows the average cross-sectional area of gastrocnemius muscle when treated with glycerol or when co-treated with glycerol and ebselen (***=p<0.001, $=p<0.05)
Figure 8L:
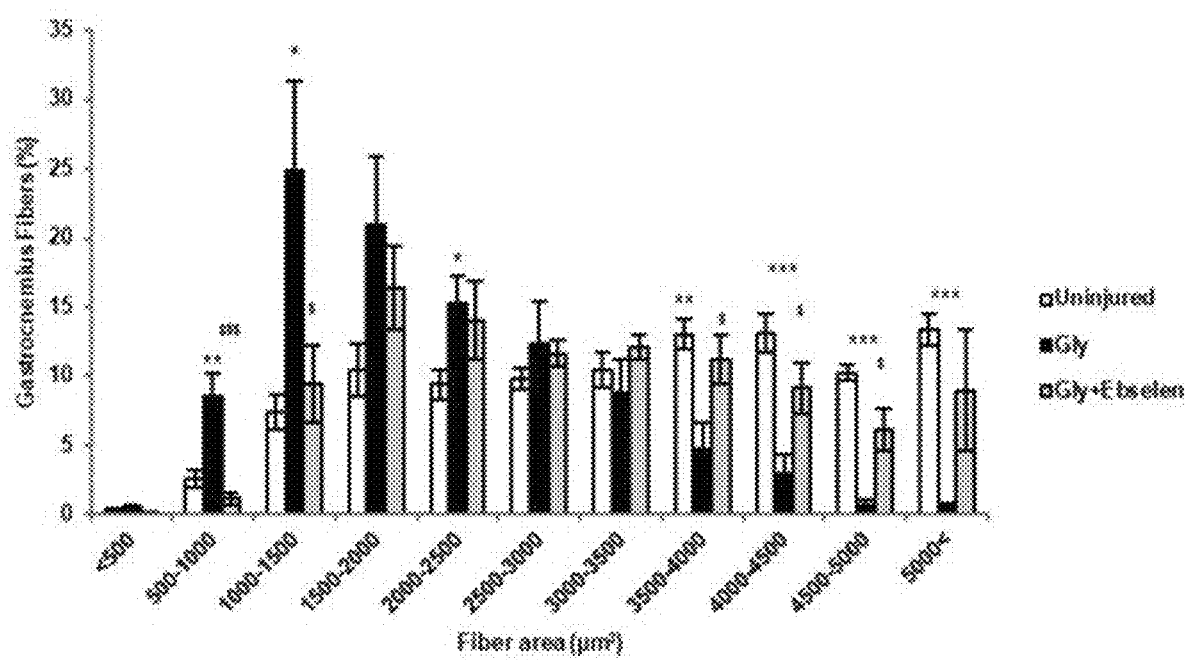
FIG. 8L shows a distribution of gastrocnemius fiber cross-sectional areas when treated with glycerol or when co-treated with glycerol and ebselen (*=p<0.05, =p<0.01, *=p<0.01, $=p<0.05, $$$=p<0.001)

On the other hand, the result of histological evaluation of the dissected abdominal muscles indicated that the ebselen treatment reduced a damaged area (FIGS. 8H and 8I) and induced a larger fiber cross-sectional area (FIGS. 8J to 8L).

Figure 8M:
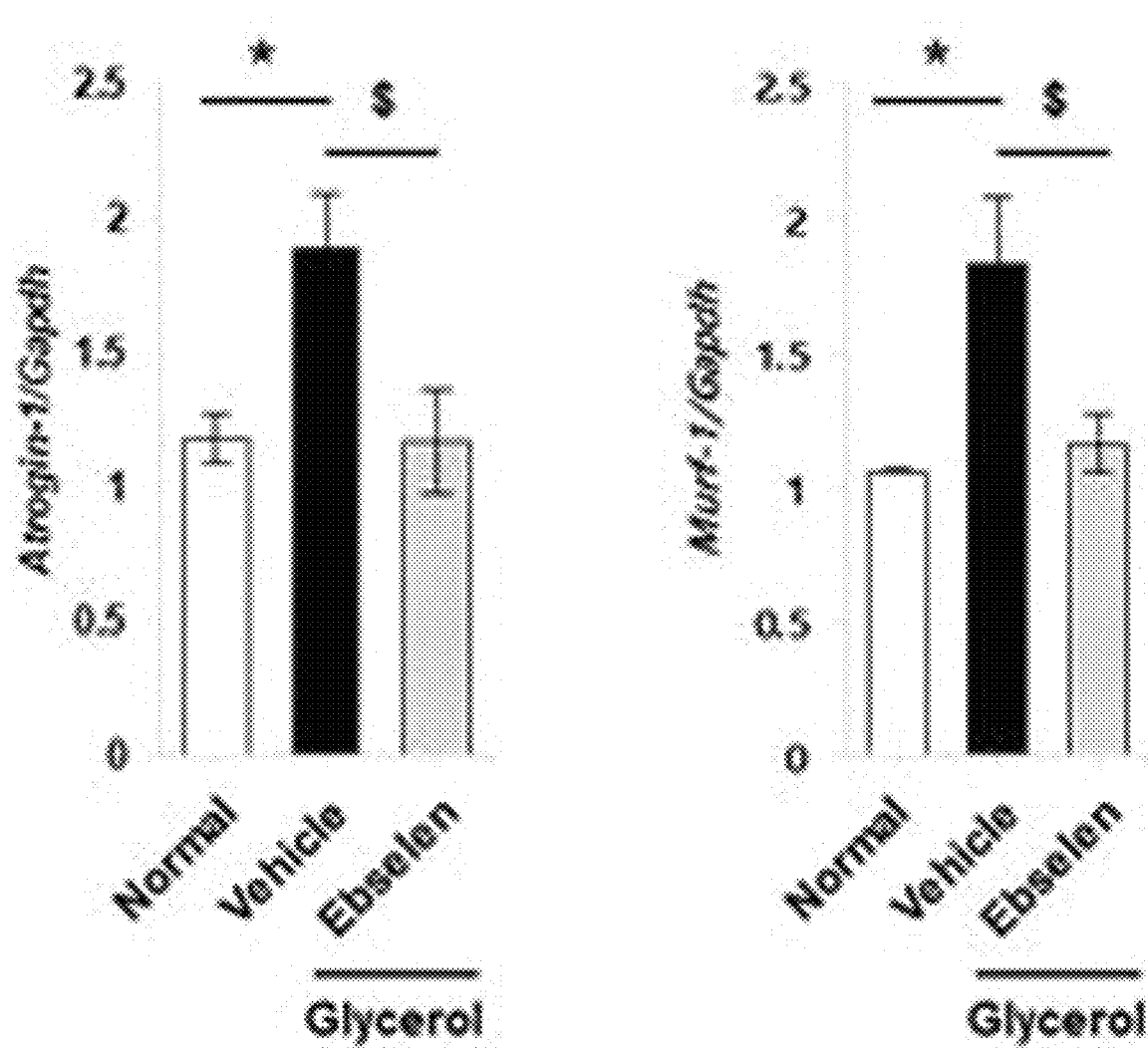
FIG. 8M shows the results of qPCR analysis on the expression of Atrogin-1 and the expression of MuRF-1 in gastrocnemius muscle of mice treated with glycerol alone or co-treated with glycerol and ebselen (*=p<0.05, $=p<0.05)

The gastrocnemius muscle damaged by glycerol injection increased the expression of Atrogin-1 and Murf-1, and it was confirmed through qPCR assay that the expression of Atrogin-1 and Murf-1 was effectively reduced by ebselen treatment (FIG. 8M).

Example 9: Confirmation of Effect of Ebselen on Atrophy in Human Myotube

Figure 9A:
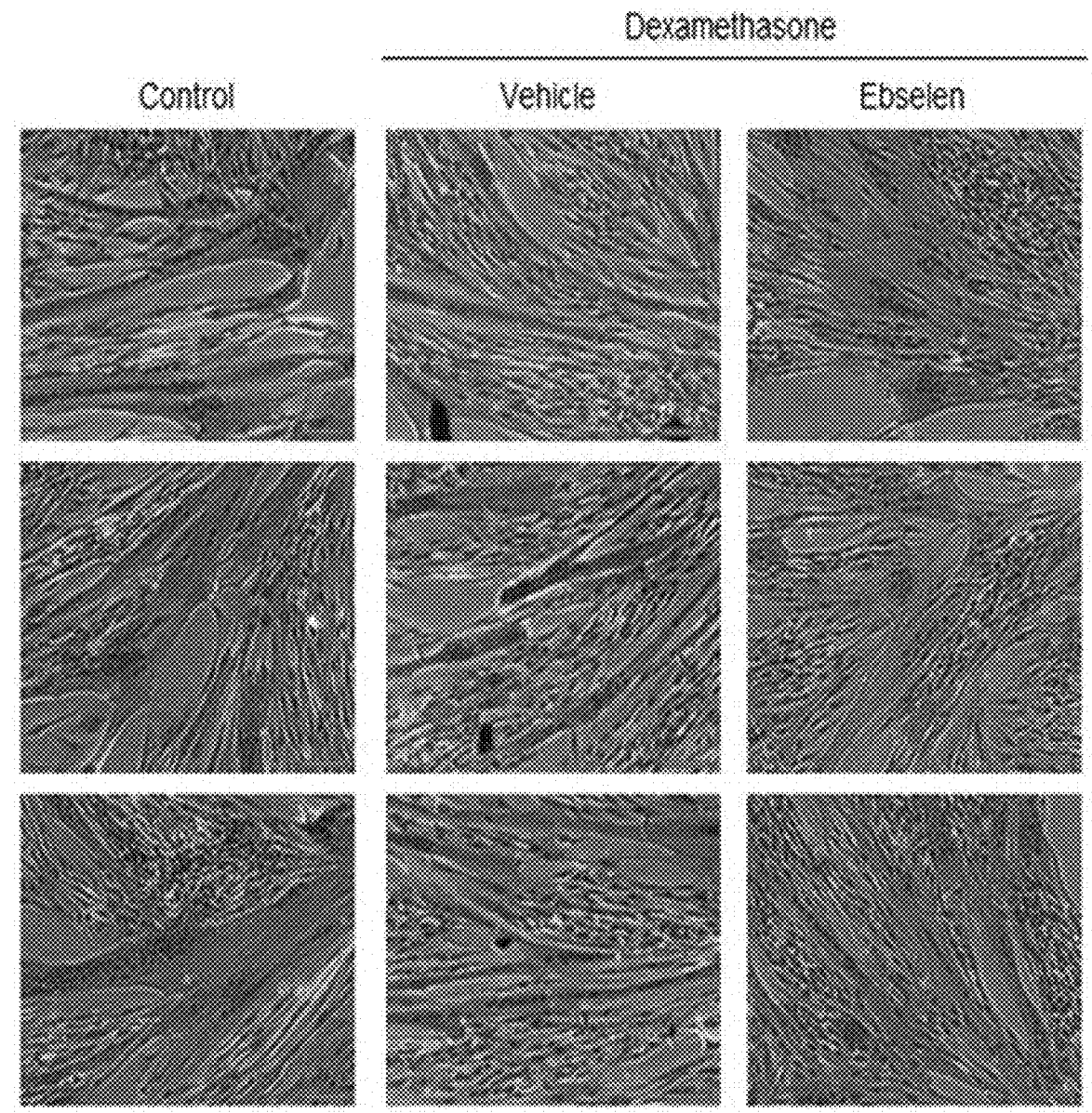
FIG. 9A shows DIC images of human skeletal myoblasts into which dexamethasone is treated alone or dexamethasone and ebselen are treated in combination (scale bar=100 μm)
Figure 9B:
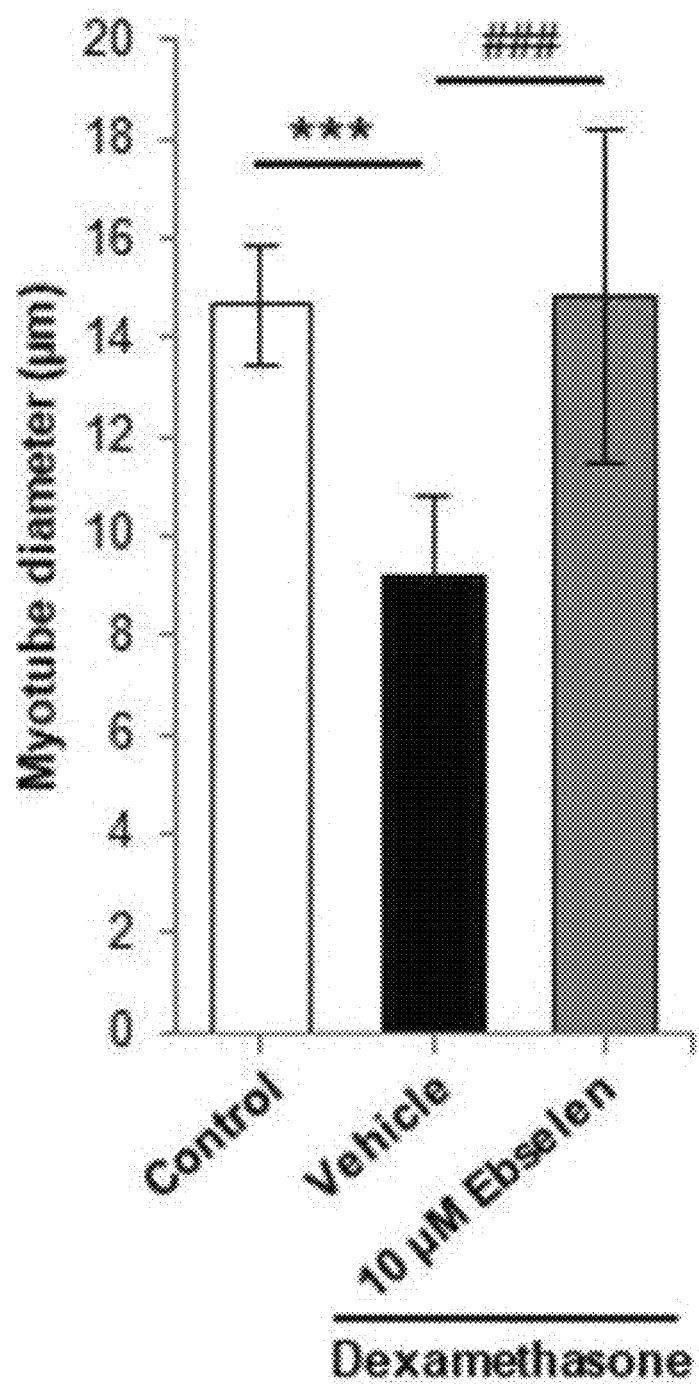
FIGS. 9B and 9C show the average diameter of myotubes and a diameter distribution of myotubes when dexamethasone is administered alone or when dexamethasone and ebselen are administered in combination.
Figure 9C:
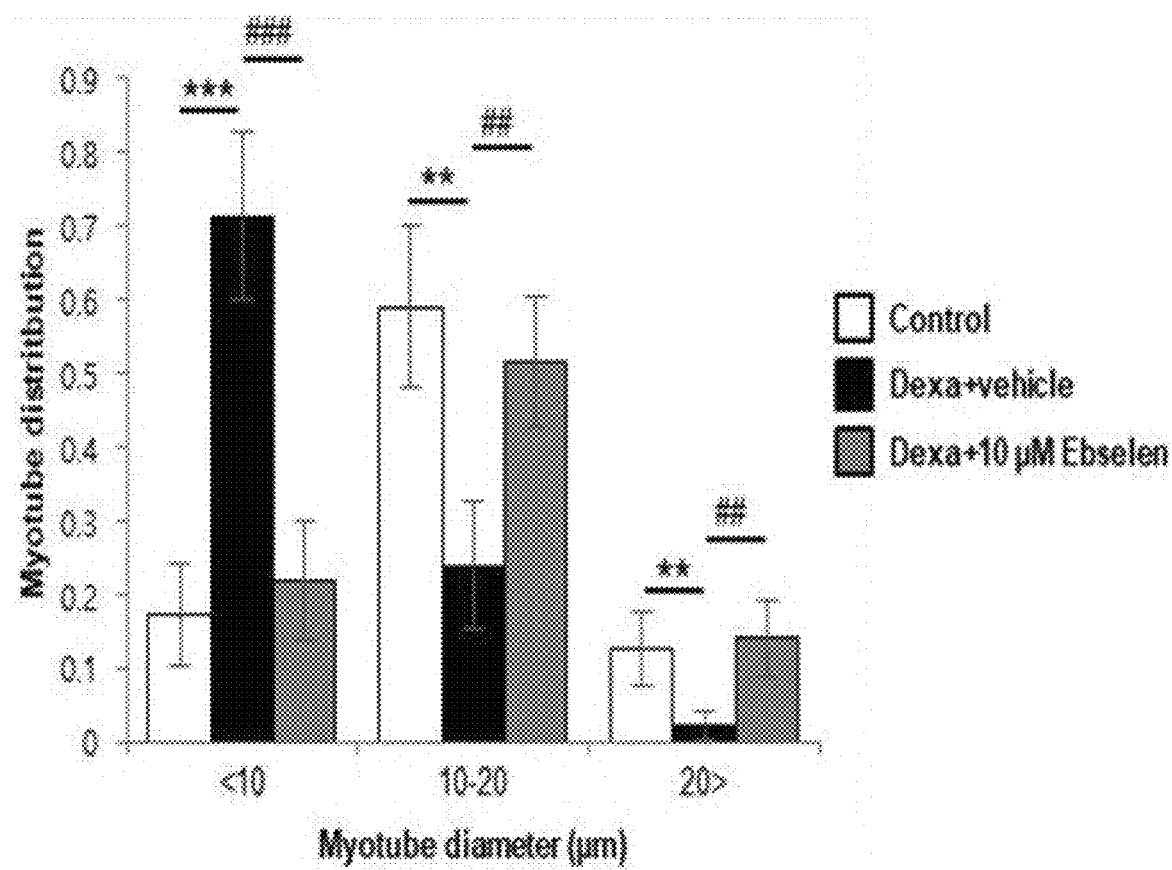

To evaluate whether ebselen has potential as an anti-muscle-wasting compound in human skeletal myotubes, differentiating human primary myoblasts were treated with dexamethasone in the presence and absence of ebselen. As a result, it was confirmed that treatment with dexamethasone reduced both the myotube diameter and the proportion of large diameter myotubes but cotreatment with ebselen inhibited the effect of dexamethasone (FIGS. 9A to 9C).

What is claimed is:

1. A pharmaceutical composition for treating skeletal muscle atrophy, the composition comprising a compound represented by Formula 1, a stereoisomer thereof, or a pharmaceutically approved salt thereof, as an active ingredient:

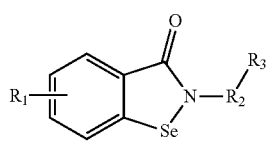

[Formula 1]

In Formula 1, $R_1$ is selected from the group consisting of hydrogen, halogen, $C_1$-$C_4$ alkyl, $C_1$-$C_4$ alkoxy, $C_1$-$C_4$ hydroxyalkyl, $C_1$-$C_4$ cyanoalkyl, $C_1$-$C_4$ haloalkyl, hydroxy, cyano, and halogen, $R_2$ is $C_1$-$C_4$ alkyl or a single bond, and $R_3$ is $C_5$-$C_7$ aryl or heteroaryl, wherein at least one hydrogen atom (H) of the aryl or heteroaryl may be substituted with $C_1$-$C_4$ alkyl, $C_1$-$C_4$ alkoxy, $C_1$-$C_4$ haloalkyl, $C_1$-$C_4$ hydroxyalkyl, $C_1$-$C_4$ cyanoalkyl, hydroxy, cyano, or halogen.

2. The pharmaceutical composition of claim 1, wherein $R_1$ is hydrogen or $C_1$-$C_4$ alkyl, $R_2$ is a single bond, and $R_3$ is $C_6$ aryl or heteroaryl, and wherein at least one hydrogen atom (H) of the aryl or heteroaryl is substitutable with $C_1$-$C_4$ alkyl.

3. The pharmaceutical composition of claim 1, wherein $R_1$ is hydrogen or $C_1$-$C_4$ alkyl, $R_2$ is a single bond, and $R_3$ is phenyl, and wherein at least one hydrogen atom (H) of the phenyl is substitutable with $C_1$-$C_4$ alkyl.

4. The pharmaceutical composition of claim 1, wherein the compound of Formula 1 is represented by Formula 2:

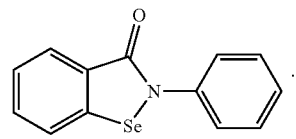

[Formula 2]

5. A food composition for improving skeletal muscle atrophy, the composition including a compound represented by Formula 1, a stereoisomer, or a salt thereof, as an active ingredient:

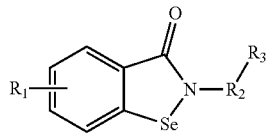

[Formula 1]

In Formula 1, $R_1$ is selected from the group consisting of hydrogen, halogen, $C_1$-$C_4$ alkyl, $C_1$-$C_4$ alkoxy, $C_1$-$C_4$ hydroxyalkyl, $C_1$-$C_4$ cyanoalkyl, $C_1$-$C_4$ haloalkyl, hydroxy, cyano, and halogen, $R_2$ is $C_1$-$C_4$ alkyl or a single bond, and $R_3$ is $C_5$-$C_7$ aryl or heteroaryl, wherein at least one hydrogen atom (H) of the aryl or heteroaryl may be substituted with $C_1$-$C_4$ alkyl, $C_1$-$C_4$ alkoxy, $C_1$-$C_4$ haloalkyl, $C_1$-$C_4$ hydroxyalkyl, $C_1$-$C_4$ cyanoalkyl, hydroxy, cyano, or halogen.

6. The food composition of claim 5, wherein $R_1$ is hydrogen or $C_1$-$C_4$ alkyl, $R_2$ is a single bond, and $R_3$ is $C_6$ aryl or heteroaryl, and wherein at least one hydrogen atom (H) of the aryl or heteroaryl is substitutable with $C_1$-$C_4$ alkyl.

7. The food composition of claim 5, wherein $R_1$ is hydrogen or $C_1$-$C_4$ alkyl, $R_2$ is a single bond, and $R_3$ is phenyl, and wherein at least one hydrogen atom (H) of the phenyl is substitutable with $C_1$-$C_4$ alkyl.

8. The food composition of claim 5, wherein the compound of Formula 1 is represented by Formula 2:

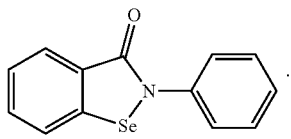

[Formula 2]

* * * * *

UNITED STATES PATENT AND TRADEMARK OFFICE
CERTIFICATE OF CORRECTION

PATENT NO. : 11,878,003 B2
APPLICATION NO. : 17/448755
DATED : January 23, 2024
INVENTOR(S) : Darren Reece Williams et al.

Page 1 of 1

It is certified that error appears in the above-identified patent and that said Letters Patent is hereby corrected as shown below:

On the Title Page

Item [73], Please correct the name and residence of assignee from "Gwangju Institute of Science and Technology, Gwangu, Republic of Korea" to "PLUTO INC., Seongnam-si, Republic of Korea".

Signed and Sealed this
Twenty-seventh Day of August, 2024

Katherine Kelly Vidal
*Director of the United States Patent and Trademark Office*